(12) United States Patent
Kishimoto et al.

(10) Patent No.: US 11,779,641 B2
(45) Date of Patent: *Oct. 10, 2023

(54) TOLEROGENIC SYNTHETIC NANOCARRIERS FOR ALLERGY THERAPY

(71) Applicant: Selecta Biosciences, Inc., Watertown, MA (US)

(72) Inventors: Takashi Kei Kishimoto, Lexington, MA (US); Christopher Fraser, Arlington, MA (US); Roberto A. Maldonado, Jamaica Plain, MA (US)

(73) Assignee: Selecta Biosciences, Inc., Watertown, MA (US)

(*) Notice: Subject to any disclaimer, the term of this patent is extended or adjusted under 35 U.S.C. 154(b) by 36 days.

This patent is subject to a terminal disclaimer.

(21) Appl. No.: 15/061,204

(22) Filed: Mar. 4, 2016

(65) Prior Publication Data

US 2016/0279234 A1 Sep. 29, 2016

Related U.S. Application Data

(62) Division of application No. 13/457,977, filed on Apr. 27, 2012, now Pat. No. 9,289,476.

(60) Provisional application No. 61/531,147, filed on Sep. 6, 2011, provisional application No. 61/531,153, filed on Sep. 6, 2011, provisional application No. 61/531,164, filed on Sep. 6, 2011, provisional application No. 61/531,168, filed on Sep. 6, 2011, provisional application No. 61/531,175, filed on Sep. 6, 2011, provisional application No. 61/531,180, filed on Sep. 6, 2011, provisional application No. 61/531,194, filed on Sep. 6, 2011, provisional application No. 61/531,204, filed on Sep. 6, 2011, provisional application No. 61/531,209, filed on Sep.

(Continued)

(51) Int. Cl.

| | | |
|---|---|---|
| A61K 39/385 | (2006.01) |
| A61K 39/35 | (2006.01) |
| G01N 33/50 | (2006.01) |
| G01N 33/569 | (2006.01) |
| A61K 39/00 | (2006.01) |
| A61K 9/127 | (2006.01) |
| A61K 9/51 | (2006.01) |
| A61K 38/38 | (2006.01) |
| A61K 47/50 | (2017.01) |
| A61K 47/52 | (2017.01) |
| A61K 47/54 | (2017.01) |
| A61K 47/59 | (2017.01) |
| A61K 47/64 | (2017.01) |
| A61K 47/69 | (2017.01) |
| B82Y 5/00 | (2011.01) |
| A61K 39/36 | (2006.01) |
| A61K 31/192 | (2006.01) |
| A61K 9/14 | (2006.01) |
| A61K 38/13 | (2006.01) |
| A61K 38/18 | (2006.01) |
| B82Y 40/00 | (2011.01) |

(52) U.S. Cl.
CPC ............ *A61K 39/385* (2013.01); *A61K 9/127* (2013.01); *A61K 9/14* (2013.01); *A61K 9/51* (2013.01); *A61K 9/5115* (2013.01); *A61K 9/5146* (2013.01); *A61K 9/5153* (2013.01); *A61K 31/192* (2013.01); *A61K 38/13* (2013.01); *A61K 38/1816* (2013.01); *A61K 38/38* (2013.01); *A61K 39/00* (2013.01); *A61K 39/001* (2013.01); *A61K 39/0008* (2013.01); *A61K 39/35* (2013.01); *A61K 39/36* (2013.01); *A61K 47/50* (2017.08); *A61K 47/52* (2017.08); *A61K 47/544* (2017.08); *A61K 47/593* (2017.08); *A61K 47/643* (2017.08); *A61K 47/69* (2017.08); *A61K 47/6923* (2017.08); *A61K 47/6929* (2017.08); *A61K 47/6937* (2017.08); *B82Y 5/00* (2013.01); *G01N 33/505* (2013.01); *G01N 33/56972* (2013.01); *A61K 2039/5154* (2013.01); *A61K 2039/55511* (2013.01); *A61K 2039/55555* (2013.01); *A61K 2039/577* (2013.01); *B82Y 40/00* (2013.01); *G01N 2333/7051* (2013.01); *G01N 2333/70514* (2013.01); *G01N 2333/70517* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,100,669 A | 3/1992 | Hyon et al. |
| 5,543,158 A | 8/1996 | Gref et al. |

(Continued)

FOREIGN PATENT DOCUMENTS

| | | |
|---|---|---|
| BR | PI0808635 A2 | 8/2014 |
| BR | 112013027500 A2 | 1/2017 |

(Continued)

OTHER PUBLICATIONS

International Preliminary Report on Patentability for PCT/US2012/035383 dated Nov. 7, 2013.

(Continued)

*Primary Examiner* — Phuong Huynh

(74) *Attorney, Agent, or Firm* — Wolf, Greenfield & Sacks, P.C.

(57) ABSTRACT

Disclosed are synthetic nanocarrier compositions, and related methods, comprising immunosuppressants and MHC Class II-restricted epitopes of an allergen that provide tolerogenic immune responses specific to the allergen.

18 Claims, 5 Drawing Sheets

Specification includes a Sequence Listing.

Related U.S. Application Data 6, 2011, provisional application No. 61/531,215, filed on Sep. 6, 2011, provisional application No. 61/513,514, filed on Jul. 29, 2011, provisional application No. 61/480,946, filed on Apr. 29, 2011.

(56) References Cited

U.S. PATENT DOCUMENTS

| | | | |
|---|---|---|---|
| 5,578,325 A | 11/1996 | Domb et al. | |
| 5,679,347 A | 10/1997 | Porcelli et al. | |
| 5,700,674 A | 12/1997 | Koyama et al. | |
| 5,762,904 A | 6/1998 | Okada et al. | |
| 5,912,017 A | 6/1999 | Mathiowitz et al. | |
| 5,928,647 A | 7/1999 | Rock | |
| 6,007,845 A | 12/1999 | Domb et al. | |
| 6,009,548 A | 12/1999 | Chen et al. | |
| 6,060,082 A | 5/2000 | Chen et al. | |
| 6,197,229 B1 | 3/2001 | Ando et al. | |
| 6,251,957 B1 | 6/2001 | Wilson | |
| 6,254,890 B1 | 7/2001 | Hirosue et al. | |
| 6,306,640 B1 | 10/2001 | Nicolette | |
| 6,387,397 B1 | 5/2002 | Chen et al. | |
| 6,468,771 B1 | 10/2002 | Einerhand et al. | |
| 6,800,296 B1 | 10/2004 | Langer et al. | |
| 6,838,089 B1 | 1/2005 | Carlsson et al. | |
| 6,881,421 B1 | 4/2005 | da Silveira et al. | |
| 6,913,915 B2 | 7/2005 | Ensor et al. | |
| 7,045,508 B2 | 5/2006 | Scaria | |
| 7,186,699 B2 | 3/2007 | Harding et al. | |
| 7,465,583 B2 | 12/2008 | Samulski et al. | |
| 7,550,441 B2 | 6/2009 | Farokhzad et al. | |
| 7,727,969 B2 | 6/2010 | Farokhzad | |
| 7,790,449 B2 | 9/2010 | Gao et al. | |
| 7,803,622 B2 | 9/2010 | Engelhardt et al. | |
| 7,884,109 B2 | 2/2011 | Ohlmeyer et al. | |
| 8,343,497 B2 | 1/2013 | Shi et al. | |
| 8,367,113 B2 | 2/2013 | Gu et al. | |
| 8,409,842 B2 | 4/2013 | Clark et al. | |
| 8,455,510 B2 | 6/2013 | Nan et al. | |
| 8,568,487 B2 | 10/2013 | Witt et al. | |
| 8,629,151 B2 | 1/2014 | Zepp et al. | |
| 8,637,255 B2 | 1/2014 | Wilson et al. | |
| 8,652,487 B2 | 2/2014 | Maldonado et al. | |
| 8,654,487 B2 | 2/2014 | Mikani et al. | |
| 8,679,837 B2 | 3/2014 | Zolotukhin et al. | |
| 8,865,487 B2 | 10/2014 | Kostka et al. | |
| 9,005,665 B2 | 4/2015 | Gourapura | |
| 9,006,254 B2 | 4/2015 | Zepp et al. | |
| 9,017,697 B2 | 4/2015 | Thomas | |
| 9,066,978 B2 | 6/2015 | Ilyinskii et al. | |
| 9,265,815 B2 | 2/2016 | Fraser et al. | |
| 9,289,476 B2 | 3/2016 | Fraser et al. | |
| 9,289,477 B2 | 3/2016 | Fraser et al. | |
| 9,295,718 B2 | 3/2016 | Fraser et al. | |
| 9,377,454 B2 | 6/2016 | Rosario-Jansen et al. | |
| 9,636,309 B2 | 5/2017 | Carlyle et al. | |
| 9,764,031 B2 | 9/2017 | Ilyinskii et al. | |
| 9,884,112 B2 | 2/2018 | Zepp et al. | |
| 9,987,354 B2 | 6/2018 | Fraser et al. | |
| 9,993,548 B2 | 6/2018 | Maldonado et al. | |
| 9,994,443 B2 | 6/2018 | Zepp et al. | |
| 10,004,802 B2 | 6/2018 | Kishimoto et al. | |
| 10,039,822 B2 | 8/2018 | Altreuter et al. | |
| 10,046,064 B2 | 8/2018 | Kishimoto | |
| 10,071,114 B2 | 9/2018 | Kishimoto | |
| 10,335,395 B2 | 7/2019 | Kishimoto | |
| 10,357,482 B2 | 7/2019 | Maldonado | |
| 10,357,483 B2 | 7/2019 | Maldonado et al. | |
| 10,420,835 B2 | 9/2019 | Fraser et al. | |
| 10,434,088 B2 | 10/2019 | Maldonado et al. | |
| 10,441,651 B2 | 10/2019 | Kishimoto et al. | |
| 10,668,053 B2 | 6/2020 | Maldonado | |
| 11,235,057 B2 | 2/2022 | Altreuter et al. | |
| 11,298,342 B2 | 4/2022 | Maldonado | |
| 11,426,451 B2 | 8/2022 | Johnston | |
| 2002/0014242 A1 | 2/2002 | Scaria et al. | |
| 2002/0019361 A1 | 2/2002 | Scaria | |
| 2002/0086049 A1 | 7/2002 | Bolton et al. | |
| 2002/0095135 A1 | 7/2002 | Meeker | |
| 2004/0005315 A1 | 1/2004 | Siemionow | |
| 2004/0204379 A1 | 1/2004 | Cheng et al. | |
| 2004/0029106 A1 | 2/2004 | Samulski et al. | |
| 2004/0038406 A1 | 2/2004 | Unger et al. | |
| 2004/0043483 A1 | 3/2004 | Qian et al. | |
| 2004/0141958 A1 | 7/2004 | Steinaa et al. | |
| 2004/0247680 A1 | 12/2004 | Farokhzad et al. | |
| 2005/0037075 A1 | 2/2005 | Farokhzad et al. | |
| 2006/0002852 A1 | 1/2006 | Saltzman et al. | |
| 2006/0002971 A1 | 1/2006 | Saltzman et al. | |
| 2006/0147432 A1 | 7/2006 | Moore et al. | |
| 2006/0159766 A1 | 7/2006 | Jenkins et al. | |
| 2006/0210638 A1 | 9/2006 | Liversidge et al. | |
| 2006/0222652 A1 | 10/2006 | Sebbel et al. | |
| 2006/0251677 A1 | 11/2006 | Bachmann et al. | |
| 2006/0251710 A1 | 11/2006 | Kwon et al. | |
| 2006/0251711 A1 | 11/2006 | Konduri et al. | |
| 2006/0269540 A1 | 11/2006 | Robert et al. | |
| 2007/0014804 A1 | 1/2007 | Burkhard | |
| 2007/0036757 A1 | 2/2007 | Kleinschmidt et al. | |
| 2007/0110685 A1 | 5/2007 | Auspitz et al. | |
| 2007/0110724 A1 | 5/2007 | Samulski et al. | |
| 2007/0190032 A1 | 8/2007 | Coffey et al. | |
| 2007/0254897 A1 | 11/2007 | Gjorstrup | |
| 2008/0031899 A1* | 2/2008 | Reddy | A61K 39/385 424/277.1 |
| 2008/0044484 A1 | 2/2008 | Minev | |
| 2008/0064859 A1 | 3/2008 | Vandenbark et al. | |
| 2008/0081074 A1 | 4/2008 | Gu et al. | |
| 2008/0145441 A1 | 6/2008 | Penades et al. | |
| 2008/0160089 A1 | 7/2008 | Vitiello et al. | |
| 2008/0254045 A1 | 10/2008 | Donda et al. | |
| 2008/0268063 A1 | 10/2008 | Jon et al. | |
| 2008/0311140 A1 | 12/2008 | Lee et al. | |
| 2009/0004259 A1 | 1/2009 | Rabinovich et al. | |
| 2009/0028910 A1 | 1/2009 | DeSimone et al. | |
| 2009/0028948 A1 | 1/2009 | Cammarano et al. | |
| 2009/0074828 A1 | 3/2009 | Frank et al. | |
| 2009/0082260 A1 | 3/2009 | Lamb et al. | |
| 2009/0142318 A1 | 6/2009 | Eck et al. | |
| 2009/0155292 A1 | 6/2009 | Santamaria et al. | |
| 2009/0226525 A1 | 9/2009 | de los Rios et al. | |
| 2009/0298710 A1 | 12/2009 | Farokhzad et al. | |
| 2010/0008932 A1 | 1/2010 | Bensussan et al. | |
| 2010/0028450 A1 | 2/2010 | Vasu et al. | |
| 2010/0055076 A1 | 3/2010 | Lim et al. | |
| 2010/0055189 A1 | 3/2010 | Hubbell et al. | |
| 2010/0062968 A1 | 3/2010 | Pulendran et al. | |
| 2010/0068261 A1 | 3/2010 | Tamarkin et al. | |
| 2010/0068286 A1 | 3/2010 | Troiano et al. | |
| 2010/0069426 A1 | 3/2010 | Zale et al. | |
| 2010/0080816 A1 | 4/2010 | Hadeiba et al. | |
| 2010/0099613 A1 | 4/2010 | Buyse et al. | |
| 2010/0111993 A1 | 5/2010 | Tureci et al. | |
| 2010/0112077 A1 | 5/2010 | Desai et al. | |
| 2010/0129392 A1 | 5/2010 | Shi et al. | |
| 2010/0129439 A1 | 5/2010 | Alexis et al. | |
| 2010/0151000 A1 | 6/2010 | Thomas et al. | |
| 2010/0172994 A1 | 7/2010 | Sigmund et al. | |
| 2010/0183602 A1 | 7/2010 | Carballido Herrera et al. | |
| 2010/0183727 A1 | 7/2010 | Iannacone et al. | |
| 2010/0189742 A1 | 7/2010 | Van Der Burg et al. | |
| 2010/0196401 A1 | 8/2010 | Scaria | |
| 2010/0203142 A1 | 8/2010 | Zhang et al. | |
| 2010/0233197 A1 | 9/2010 | Wakatsuki Pedersen et al. | |
| 2010/0233251 A1 | 9/2010 | Von Andrian et al. | |
| 2010/0273220 A1 | 10/2010 | Yanik et al. | |
| 2010/0303850 A1 | 12/2010 | Lipford et al. | |
| 2010/0323019 A1 | 12/2010 | Lim et al. | |
| 2010/0323199 A1 | 12/2010 | Gu et al. | |
| 2011/0004148 A1 | 1/2011 | Ishii et al. | |
| 2011/0020388 A1 | 1/2011 | Zepp et al. | |
| 2011/0027217 A1 | 2/2011 | Zepp et al. | |
| 2011/0052697 A1 | 3/2011 | Farokhzad et al. | |
| 2011/0070153 A1 | 3/2011 | Hyde et al. | |

(56) References Cited

U.S. PATENT DOCUMENTS

| | | |
|---|---|---|
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0166172 A1 | 7/2011 | Nan et al. |
| 2011/0171248 A1 | 7/2011 | Pittet et al. |
| 2011/0223201 A1 | 9/2011 | Lipford et al. |
| 2011/0243976 A1 | 10/2011 | Bagnoli et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0039989 A1 | 2/2012 | Hubbell et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0076831 A1 | 3/2012 | Miller et al. |
| 2012/0077860 A1 | 3/2012 | Garcia |
| 2012/0100606 A1 | 4/2012 | Zolotukhin et al. |
| 2012/0114677 A1 | 5/2012 | Zepp et al. |
| 2012/0148612 A1 | 6/2012 | Hafner et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308563 A1 | 12/2012 | Arya et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2013/0096182 A1 | 4/2013 | Chatterjee et al. |
| 2014/0030344 A1 | 1/2014 | Zepp et al. |
| 2014/0031418 A1 | 1/2014 | Wilson et al. |
| 2014/0037585 A1 | 2/2014 | Wright et al. |
| 2014/0155469 A1 | 6/2014 | Bahou et al. |
| 2014/0193453 A1 | 7/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0336245 A1 | 11/2014 | Mingozzi et al. |
| 2014/0356361 A1 | 12/2014 | Maldonado et al. |
| 2015/0024007 A1 | 1/2015 | Hessel et al. |
| 2015/0065562 A1 | 3/2015 | Yazicioglu et al. |
| 2015/0099707 A1 | 4/2015 | Pastan et al. |
| 2015/0111955 A1 | 4/2015 | High et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto et al. |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2017/0021037 A1 | 1/2017 | Wang et al. |
| 2017/0224620 A1 | 8/2017 | Zale et al. |
| 2017/0258927 A1 | 9/2017 | Johnston |
| 2017/0349433 A1 | 12/2017 | Lipford et al. |
| 2018/0043023 A1 | 2/2018 | Ilyinski et al. |
| 2018/0071394 A1 | 3/2018 | O'Neil et al. |
| 2018/0085319 A1 | 3/2018 | Kishimoto |
| 2018/0193482 A1 | 7/2018 | Ilyinskii et al. |
| 2018/0256709 A1 | 9/2018 | Zepp et al. |
| 2018/0289776 A1 | 10/2018 | Johnston et al. |
| 2019/0076458 A1 | 3/2019 | Kishimoto et al. |
| 2019/0076522 A1 | 3/2019 | Altreuter et al. |
| 2019/0142974 A1 | 5/2019 | Ilyinskii et al. |
| 2020/0038462 A1 | 2/2020 | Keller et al. |
| 2020/0038463 A1 | 2/2020 | Keller et al. |
| 2020/0069659 A1 | 3/2020 | Kishimoto |
| 2020/0069660 A1 | 3/2020 | Maldonado et al. |
| 2020/0078341 A1 | 3/2020 | Maldonado |
| 2020/0101154 A1 | 4/2020 | Fraser et al. |
| 2020/0101155 A1 | 4/2020 | Kishimoto et al. |
| 2020/0113874 A1 | 4/2020 | Maldonado et al. |
| 2020/0360350 A1 | 11/2020 | Maldonado |
| 2020/0360453 A1 | 11/2020 | Kishimoto et al. |
| 2020/0390718 A1 | 12/2020 | Kishimoto et al. |
| 2020/0399628 A1 | 12/2020 | Johnston et al. |
| 2021/0154324 A1 | 5/2021 | Ilyinskii et al. |
| 2021/0187081 A1 | 6/2021 | Johnston et al. |
| 2021/0290601 A1 | 9/2021 | Ilyinskii et al. |
| 2021/0308058 A1 | 10/2021 | Johnston |
| 2022/0071968 A1 | 3/2022 | Kishimoto |
| 2022/0133864 A1 | 5/2022 | Kishimoto |
| 2022/0323607 A1 | 10/2022 | Kishimoto et al. |
| 2023/0032226 A1 | 2/2023 | Maldonado |
| 2023/0107561 A1 | 4/2023 | Johnston |

FOREIGN PATENT DOCUMENTS

| | | |
|---|---|---|
| BR | 112013027514 A2 | 2/2017 |
| BR | 112015023793 A2 | 7/2017 |
| BR | 112015027279 A2 | 9/2017 |
| CA | 2834514 A1 | 11/2012 |
| CN | 1335398 | 2/2002 |
| CN | 1391479 | 1/2003 |
| CN | 1678188 A | 10/2005 |
| CN | 1979166 A | 6/2007 |
| CN | 101175481 A | 5/2008 |
| CN | 101437491 A | 5/2009 |
| CN | 101484461 A | 7/2009 |
| CN | 101646418 A | 2/2010 |
| CN | 101703781 A | 5/2010 |
| CN | 101861165 A | 10/2010 |
| CN | 101990429 A | 3/2011 |
| CN | 102016814 A | 4/2011 |
| CN | 103079589 A | 5/2013 |
| CN | 103282380 A | 9/2013 |

(56) References Cited

FOREIGN PATENT DOCUMENTS

| | | |
|---|---|---|
| CN | 102871966 B | 11/2013 |
| CN | 103491957 A | 1/2014 |
| CN | 103501793 | 1/2014 |
| CN | 103501820 A | 1/2014 |
| CN | 105283175 | 1/2016 |
| CN | 105307641 A | 2/2016 |
| CN | 105339012 A | 2/2016 |
| CN | 106714826 A | 5/2017 |
| CN | 106715699 A | 5/2017 |
| CN | 107073091 A | 8/2017 |
| CN | 107075499 A | 8/2017 |
| EP | 0759941 B1 | 9/2000 |
| EP | 1 153 122 B1 | 11/2001 |
| EP | 1795185 A2 | 6/2007 |
| EP | 1 932 538 A1 | 6/2008 |
| EP | 2073848 A2 | 7/2009 |
| EP | 2217269 A2 | 8/2010 |
| EP | 2345412 A1 | 7/2011 |
| EP | 2522338 A2 | 11/2012 |
| EP | 3426285 A1 | 1/2019 |
| JP | H01-502909 A | 10/1989 |
| JP | H10-507758 A | 7/1998 |
| JP | 2005-516893 A | 6/2005 |
| JP | 2006-257095 | 9/2006 |
| JP | 2007-532517 A | 11/2007 |
| JP | 2008-515806 | 5/2008 |
| JP | 2008-532953 A | 8/2008 |
| JP | 2009-531068 | 9/2009 |
| JP | 2010-100578 A | 5/2010 |
| JP | 2010-514805 | 5/2010 |
| JP | 2010-533160 A | 10/2010 |
| JP | 2010-535025 | 11/2010 |
| JP | 2011-512326 A | 4/2011 |
| JP | 2012-502930 A | 2/2012 |
| JP | 2012-512175 | 5/2012 |
| JP | 2012-515722 A | 7/2012 |
| JP | 2012-516691 A | 7/2012 |
| JP | 2013-541504 A | 11/2013 |
| JP | 2014-513092 A | 5/2014 |
| JP | 2014-513102 A | 5/2014 |
| JP | 2014-513722 A | 6/2014 |
| JP | 2014-514331 A | 6/2014 |
| JP | 2014-514332 A | 6/2014 |
| JP | 2014-514333 A | 6/2014 |
| JP | 2017-513048 | 5/2017 |
| JP | 2017-122113 A | 7/2017 |
| JP | 2017-527565 A | 9/2017 |
| JP | 2017-527571 A | 9/2017 |
| JP | 2017-529342 A | 10/2017 |
| KR | 10-2010-0099849 A | 9/2010 |
| WO | WO 88/06451 A1 | 9/1988 |
| WO | WO 95/11696 A1 | 5/1995 |
| WO | WO 95/22963 A1 | 8/1995 |
| WO | WO 96/012406 A1 | 2/1996 |
| WO | WO 96/20698 A2 | 7/1996 |
| WO | WO 1998/002441 A2 | 1/1998 |
| WO | WO 98/010056 A1 | 12/1998 |
| WO | WO 99/22762 A1 | 5/1999 |
| WO | WO 99/34826 A1 | 7/1999 |
| WO | WO 00/32626 A1 | 6/2000 |
| WO | WO 2000/42989 A2 | 7/2000 |
| WO | WO 2001/068133 A1 | 9/2001 |
| WO | WO 2001/091802 A1 | 12/2001 |
| WO | WO 02/09770 A1 | 2/2002 |
| WO | WO 02/32404 A2 | 4/2002 |
| WO | WO 02/088304 A2 | 11/2002 |
| WO | WO 2003/033526 A2 | 4/2003 |
| WO | WO 03/094840 A2 | 11/2003 |
| WO | WO 2004/050090 A1 | 6/2004 |
| WO | WO 2004/098509 A2 | 11/2004 |
| WO | WO 2005/097116 A1 | 10/2005 |
| WO | WO 2006/041890 A2 | 4/2006 |
| WO | WO 2006/094507 A1 | 9/2006 |
| WO | WO 2007/001448 A2 | 1/2007 |
| WO | WO 2007/067683 A2 | 6/2007 |
| WO | WO 2007/068747 A1 | 6/2007 |
| WO | WO 2007/070682 A2 | 6/2007 |
| WO | WO 2007/087341 A2 | 8/2007 |
| WO | WO 2007/098254 A2 | 8/2007 |
| WO | WO 2007/133807 A2 | 11/2007 |
| WO | WO 2007/133835 A2 | 11/2007 |
| WO | WO 2007/137117 A2 | 11/2007 |
| WO | WO 2007/144150 A1 | 12/2007 |
| WO | WO 2007/150030 A2 | 12/2007 |
| WO | WO 2008/019142 A2 | 2/2008 |
| WO | WO 2008/036374 A2 | 3/2008 |
| WO | WO 2008/043157 A1 | 4/2008 |
| WO | WO 2008/069942 A2 | 6/2008 |
| WO | WO 2008/071774 A1 | 6/2008 |
| WO | WO 2008/073558 A2 | 6/2008 |
| WO | WO 2008/083331 A2 | 7/2008 |
| WO | WO 2008/105773 A2 | 9/2008 |
| WO | WO 2008/109163 A1 | 9/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/129020 A1 | 10/2008 |
| WO | WO 2008/147456 A2 | 12/2008 |
| WO | WO 2008/150868 A1 | 12/2008 |
| WO | WO 2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/025324 A2 | 3/2010 |
| WO | WO 2010/027471 A2 | 3/2010 |
| WO | WO 2010/037402 A1 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/056143 A1 | 5/2010 |
| WO | WO 2010/075072 A2 | 7/2010 |
| WO | WO 2010/085509 A1 | 7/2010 |
| WO | WO 2010/089122 A2 | 8/2010 |
| WO | WO 2010/116141 A2 | 10/2010 |
| WO | WO 2010/123569 A2 | 10/2010 |
| WO | WO 2010/125565 A2 | 11/2010 |
| WO | WO 2010/138192 A2 | 12/2010 |
| WO | WO 2010/138193 A2 | 12/2010 |
| WO | WO 2010/138194 A2 | 12/2010 |
| WO | WO 2011/005850 A1 | 1/2011 |
| WO | WO 2011/033090 A1 | 3/2011 |
| WO | WO 2011/109833 A2 | 9/2011 |
| WO | WO 2011/150240 A1 | 12/2011 |
| WO | WO 2011/156119 A1 | 12/2011 |
| WO | WO 2012/019041 A2 | 2/2012 |
| WO | WO 2012/021512 A2 | 2/2012 |
| WO | WO 2012/054920 A2 | 4/2012 |
| WO | WO 2012/149247 A2 | 11/2012 |
| WO | WO 2012/149252 A2 | 11/2012 |
| WO | WO 2012/149255 A2 | 11/2012 |
| WO | WO 2012/149259 A1 | 11/2012 |
| WO | WO 2012/149265 A2 | 11/2012 |
| WO | WO 2012/149268 A1 | 11/2012 |
| WO | WO 2012/149282 A2 | 11/2012 |
| WO | WO 2012/149393 A2 | 11/2012 |
| WO | WO 2012/149405 A2 | 11/2012 |
| WO | WO 2012/149411 A1 | 11/2012 |
| WO | WO 2012/158362 A1 | 11/2012 |
| WO | WO 2013/036914 A1 | 3/2013 |
| WO | WO 2013/058812 A1 | 4/2013 |
| WO | WO 2013/123503 A1 | 8/2013 |
| WO | WO 2014/145524 A2 | 9/2014 |
| WO | WO 2014/168953 A1 | 10/2014 |
| WO | WO 2014/179771 A1 | 11/2014 |
| WO | WO 2014/179772 A2 | 11/2014 |
| WO | WO 2015/138357 A2 | 9/2015 |
| WO | WO 2015/162594 A2 | 10/2015 |
| WO | WO 2016/037161 A2 | 3/2016 |

(56) References Cited

FOREIGN PATENT DOCUMENTS

| | | |
|---|---|---|
| WO | WO 2016/037163 A1 | 3/2016 |
| WO | WO 2016/037164 A1 | 3/2016 |
| WO | WO 2016/055437 A1 | 4/2016 |
| WO | WO 2016/073798 A1 | 5/2016 |
| WO | WO 2017/139212 A1 | 8/2017 |
| WO | WO 2017/156513 A1 | 9/2017 |
| WO | WO 2018/089540 A1 | 5/2018 |
| WO | WO 2018/127382 A1 | 7/2018 |
| WO | WO 2018/129268 A1 | 7/2018 |
| WO | WO 2018/169811 A1 | 9/2018 |
| WO | WO 2019/075360 A1 | 4/2019 |
| WO | WO 2019/162951 A1 | 8/2019 |
| WO | WO 2019/217552 A1 | 11/2019 |
| WO | WO 2020/018583 A1 | 1/2020 |
| WO | WO 2020/018587 A1 | 1/2020 |
| WO | WO 2020/223205 A1 | 11/2020 |
| WO | WO 2020/243261 A1 | 12/2020 |
| WO | WO 2020/247625 A1 | 12/2020 |

OTHER PUBLICATIONS

International Search Report and Written Opinion dated Sep. 27, 2012 for Application No. PCT/US2012/035383.

Extended European Search Report for Application No. EP 12777486.7 dated Dec. 18, 2014.

[No Author Listed] Anaphylaxis. Manuals for Management of Individual Serious Adverse Drug Reactions. Ministry of Health, Labor and Welfare. Mar. 2008:1-34. Accessed online via http://www.info.pmda.go.jp/juutoku/file/jfm0803003.pdf.

[No Author Listed] Autologous Dendritic Cell Therapy for Type 1 Diabetes Suppression: A Safety Study. Clinical Trials. Mar. 2007. Last accessed Jan. 5, 2012 available at http://www.clinicaltrials.gov/ct2/show/NCT00445913?term=dendritic&cond=%22Autoimmune+Diseases%22&rank=4. 5 pages.

[No Author Listed] Autologous Tolerogenic Dendritic Cells for Rheumatoid Arthritis (AutoDECRA). Clinical Trials. May 2011. Last accessed Jan. 5, 2012 available at http://www.clinicaltrials.gov/ct2/show/NCT01352858?term=tolerogenic&rank=1. 4 pages.

[No Author Listed] Drug delivery system. Nankodo Co., Ltd. Apr. 15, 1986:70-1.

[No Author Listed] Innovative rheumatoid arthritis therapy receives backing from Janssen. Available at http://www.di.uq.edu.au/innovative-rheumatoid-arthritis-therapy-backed. Jan. 18, 2012. 3 pages.

[No Author Listed] New pharmacology. Nankodo Co. Ltd. 3rd Revised Ed. 1996:p. 468.

[No Author Listed] New Research Shows Transplanting Stem Cells from the Brain to The Pancreas Could Cure Diabetes, as Reported by DiabeticLive.com. Oct. 18, 2011. Last accessed Jan. 5, 2012 at http://www.fiercebiotech.com/press-releases/new-research-shows-transplanting-stem-cells-brain-pancreas-could-cure-diabe. 2 pages.

[No Author Listed] Novel nanoparticle vaccine cures type 1 diabetes in mice. Apr. 8, 2010. Last accessed Dec. 6, 2011 at http://www.sciencedaily.com/releases/2010/04/100408121054.htm. 2 pages.

[No Author Listed] Scientists Use Rat's Own Stem Cells to Cure Their Diabetes. Oct. 16, 2011. Last accessed Jan. 5, 2012 at http://www.diabeteshealth.com/read/2011/10/16/7321/scientists-use-rats-own-stem-cells-to-cure-their-diabetes. 4 pages.

[No Author Listed] Selecta Biosciences Announces Dosing of First Patent in Phase 1b Clinical Trial of SEL-212, Designed to be The First Non-Immunogenic Biologic Treatment for Gout. Press Release. Dec. 23, 2015. Retrieved from the Internet via http://selectabio.com/2015/12/23/selecta-biosciences-announces-dosing-of-first-patient-in-phase-1b-clinical-trial-of-sel-212-designed-to-be-the-first-non-immunogenic-biologic-treatment-for-gout. Last access on May 10, 2017.

"Pluronic." Oxford Dictionary entry accessed via www.oxforddictionary.com on May 6, 2016. 8 pages.

Aalbers et al., Preclinical Potency and Biodistribution Studies of an AAV 5 Vector Expressing Human Interferon-β (ART-I02) for Local Treatment of Patients with Rheumatoid Arthritis. PLoS One. Jun. 24, 2015;10(6):e0130612. doi:10.1371/journal.pone.0130612. 17 pages.

Ackerman et al., Cellular mechanisms governing cross-presentation of exogenous antigens. Nat Immunol. 2004;5(7):678-84.

Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.

Alewine et al., Efficacy of RG7787, a next-generation mesothelin-targeted immunotoxin, against triple-negative breast and gastric cancers. Mol Cancer Ther. Nov. 2014;13(11):2653-61. doi: 10.1158/1535-7163.MCT-14-0132. Epub Sep. 19, 2014.

Alexander et al., Universal influenza DNA vaccine encoding conserved CD4+ T cell epitopes protects against lethal viral challenge in HLA-DR transgenic mice. Vaccine. Jan. 8, 2010;28(3):664-72. Epub Nov. 4, 2009.

Amu et al., Regulatory B cells prevent and reverse allergic airway inflammation via FoxP3-positive T regulatory cells in a murine model. J Allergy Clin Immunol. 2010;125:1114-24.

Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.

Aronovich et al., Quantitative analysis of α-L-iduronidase expression in immunocompetent mice treated with the Sleeping Beauty transposon system. PLoS One. Oct. 21, 2013;8(10):e78161. doi: 10.1371/journal.pone.0078161. eCollection 2013.

Arruda et al., Strategies to modulate immune responses: a new frontier for gene therapy. Mol Ther. Sep. 2009;17(9):1492-503. doi: 10.1038/mt.2009.150. Epub Jul. 7, 2009. Review.

Asano et al., Targeting activated lymphocytes with lipid microsphere containing a cytotoxic agent; efficacy of immunosuppression with a new drug delivery system. J Urology. 2001;165(5)384.

Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05.001. Epub May 5, 2010.

Azzi et al., Polylactide-cyclosporin A nanoparticles for targeted immunosuppression. FASEB J. Oct. 2010;24(10):3927-38. doi: 10.1096/fj.10-154690. Epub Jun. 14, 2010.

Bachem et al., Superior antigen cross-presentation and XCR1 expression define human CD11c+CD141+ cells as homologues of mouse CD8+ dendritic cells. J Exp Med. Jun. 7, 2010;207(6):1273-81. Epub May 17, 2010.

Bachmann et al., T helper cell-independent neutralizing B cell response against vesicular stomatitis virus: role of antigen patterns in B cell induction?. Eur J Immunol. 1995;25(12):3445-51.

Bae et al., Vinyl sulfone-terminated PEG-PLLA diblock copolymer for thiol-reactive polymeric micelle. Apr. 9, 2009;42(10):3437-42.

Baker et al., Immunogenicity of protein therapeutics: The key causes, consequences and challenges. Self Nonself—Immune Recognition and Signaling. Dec. 1, 2010;1(4):314-22.

Barchet et al., Virus-induced interferon alpha production by a dendritic cell subset in the absence of feedback signaling in vivo. J Exp Med. 2002;195(4):507-16.

Barzel et al., Promoterless gene targeting without nucleases ameliorates haemophilia B in mice. Nature. Jan. 15, 2015;517(7534):360-4. doi: 10.1038/nature13864. Epub Jul. 15, 2015. 21 pages.

Batista et al., The who, how and where of antigen presentation to B cells. Nat Rev Immunol. Jan. 2009;9(1):15-27.

Battaglia et al., Rapamycin promotes expansion of functional CD4+ CD25+FOXP3+ regulatory T cells of both healthy subjects and type 1 diabetic patients. J Immunol. Dec. 15, 2006;177(12):8338-47.

Bawarski et al., Emerging nanopharmaceuticals. Nanomedicine. Dec. 2008;4(4):273-82. doi: 10.1016/j.nano.2008.06.002. Epub Jul. 18, 2008.

(56) References Cited

OTHER PUBLICATIONS

Bayard et al., Hepatitis B virus (HBV)-derived DRB1*0101-restricted CD4 T-cell epitopes help in the development of HBV-specific CD8+ T cells in vivo. Vaccine. May 14, 2010;28(22):3818-26. Epub Mar. 31, 2010.
Bayle et al., Rapamycin analogs with differential binding specificity permit orthogonal control of protein activity. Chem Biol. Jan. 2006;13(1):99-107.
Beevers et al., Curcumin inhibits the mammalian target of rapamycin-mediated signaling pathways in cancer cells. Int J Cancer. Aug. 15, 2006;119(4):757-64.
Berhanu et al., Pegloticase failure and a possible solution: Immunosuppression to prevent intolerance and inefficacy in patients with gout. Semin Arthritis Rheum. Jun. 2017;46(6):754-758. doi: 10.1016/j.semarthrit.2016.09.007. Epub Sep. 20, 2016.
Bi et al., High-efficiency targeted editing of large viral genomes by RNA-guided nucleases. PLoS Pathog. May 1, 2014;10(5):e1004090. doi: 10.1371/journal.ppat.1004090. eCollection May 2014.
Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.
Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.
Blander, Phagocytosis and antigen presentation: a partnership initiated by Toll-like receptors. Ann Rheum Dis. Dec. 2008;67 Suppl 3:iii44-9.
Bocian et al., Rapamycin, unlike cyclosporine A, enhances suppressive functions of in vitro-induced CD4+CD25+ Tregs. Nephrol Dial Transplant. Mar. 2010;25(3):710-7. doi: 10.1093/ndt/gfp586. Epub Nov. 9, 2009.
Boden et al., Regulatory T cells in inflammatory bowel disease. Curr Opin Gastroenterol. Nov. 2008;24(6):733-41.
Boes et al., T-cell engagement of dendritic cells rapidly rearranges MHC class II transport. Nature. 418(6901):983-988 (2002).
Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. 2002;196(12):1627-38.
Bouaziz et al., Regulatory B cells as inhibitors of immune responses and inflammation. Immunol Rev. Aug. 2008;224:201-14. doi: 10.1111/j.1600-065X.2008.00661.x. Review.
Bozzacco et al., DEC-205 receptor on dendritic cells mediates presentation of HIV gag protein to CD8+ T cells in a spectrum of human MHC I haplotypes. Proc Natl Acad Sci USA. 2007;104(4):1289-94.
Brennan et al., Invariant natural killer T cells recognize lipid self antigen induced by microbial danger signals. Nat Immunol. Oct. 30, 2011;12(12):1202-11. doi: 10.1038/ni.2143.
Brown et al., Endogenous microRNA regulation suppresses transgene expression in hematopoietic lineages and enables stable gene transfer. Nat Med. May 2006;12(5):585-91. Epub Apr. 23, 2006.
Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.
Busson et al., Prediction of CD4(+) T cell epitopes restricted to HLA-DP4 molecules. J Immunol Methods. Dec. 20, 2006;317(1-2):144-51. Epub Oct. 26, 2006.
Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3, 2009.
Capini et al., Antigen-specific suppression of inflammatory arthritis using liposomes. J Immunol. Mar. 15, 2009; 182(6):3556-65.
Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: S0264-410X(14)01129-3. doi: 10.1016/j.vaccine.2014.08.016. 9 pages.
Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.
Carrasco et al., B cells acquire particulate antigen in a macrophage-rich area at the boundary between the follicle and the subcapsular sinus of the lymph node.Immunity. Jul. 2007;27(1):160-71. Epub Jul. 19, 2007.
Carroll, Stem cell therapy used to cure types 1&2 diabetes in rat models. Oct. 18, 2011. Last accessed Jan. 5, 2012 available at http://www.fiercebiotechresearch.com/story/stem-cell-therapy-used-cure-type-12-diabetes-rat-models/2011-10-18. 2 pages.
Casola et al., B cell receptor signal strength determines B cell fate. Nat Immunol. 2004;5(3):317-27.
Castelli et al., HLA-DP4, the most frequent HLA II molecule, defines a new supertype of peptide-binding specificity. J Immunol. Dec. 15, 2002;169(12):6928-34.
Chao et al., Induction of tolerance to human factor VIII in mice. Blood. May 15, 2001;97(10):3311-2.
Chapoval et al., HLA-DQ6 and HLA-DQ8 transgenic mice respond to ragweed allergens and recognize a distinct set of epitopes on short and giant ragweed group 5 antigens. J Immunol. Aug. 15, 1998;161(4):2032-7.
Chayen et al., Lysosomal enzymes and inflammation with particular reference to rheumatoid diseases. Ann Rheum Dis. Sep. 1971;30(5):522-36.
Chen et al., Targeting transgene to the heart and liver with AAV9 by different promoters. Clin Exp Pharmacol Physiol. Oct. 2015;42(10):1108-17. doi: 10.1111/1440-1681.12453. Original Article. 24 pages.
Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.
Chengalvala et al., Enhanced immunogenicity of hepatitis B surface antigen by insertion of a helper T cell epitope from tetanus toxoid. Vaccine. Mar. 5, 1999; 17(9-10):1035-41.
Chinen et al., Basic and clinical immunology. J Allergy Clin Immunol. Aug. 2005;116(2):411-8.
Chinnery et al., The chemokine receptor CX3CR1 mediates homing of MHC class II-positive cells to the normal mouse corneal epithelium. Invest Ophthalmol Vis Sci. Apr. 2007;48(4):1568-74.
Clark, The reticulum of lymph nodes in mice studied with the electron microscope. Am J Anat. 1962;110:217-57.
Colman, Effects of amino acid sequence changes on antibody-antigen interactions. Res Immunol. Jan. 1994;145(1):33-6.
Comas et al., New nanoformulation of rapamycin Rapatar extends lifespan in homozygous p53−/− mice by delaying carcinogenesis. Aging (Albany NY). Oct. 2012;4(10):715-22.
Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.
Corti et al., B-Cell Depletion is Protective Against Anti-AAV Capsid Immune Response: A Human Subject Case Study. Mol Ther Methods Clin Dev. 2014;1. pii: 14033. 7 pages.
Crittenden et al., New therapies for gout. Annu Rev Med. 2013;64:325-37. doi: 10.1146/annurev-med-080911-105830.
Crozat et al. The XC chemokine receptor 1 is a conserved selective marker of mammalian cells homologous to mouse CD8alpha+ dendritic cells. J Exp Med. Jun. 7, 2010;207(6):1283-92. Epub May 17, 2010.
Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.

(56) References Cited

OTHER PUBLICATIONS

Cvetanovich et al., Human regulatory T cells in autoimmune diseases. Curr Opin Immunol. Dec. 2010;22(6):753-60. Epub Sep. 24, 2010.

Dai et al., Cellular and humoral immune responses to adenoviral vectors containing factor IX gene: tolerization of factor IX and vector antigens allows for long-term expression. Proc Natl Acad Sci U S A. Feb. 28, 1995;92(5):1401-5.

Dane et al., Nano-sized drug-loaded micelles deliver payload to lymph node immune cells and prolong allograft survival. J Control Release. Dec. 10, 2011;156(2):154-60. Epub Aug. 12, 2011.

Dang et al., Stimulation of B lymphocytes through surface lg receptors induces LFA-1 and ICAM-1-dependent adhesion. J Immunol. 1991;146(10):3273-9.

Dao et al., Pharmacokinetics and pharmacodynamics evaluation of therapeutic protein drugs. China Pharm. Dec. 31, 2007;18(32):2546-7.

Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008;85(4):983-92.

Davila et al., Cell-based immunotherapy with suppressor CD8+ T cells in rheumatoid arthritis. J Immunol. Jun. 1, 2005;174(11):7292-301.

Del Rio et al., Development and functional specialization of CD103+ dendritic cells. Immunol Rev. Mar. 2010;234(1):268-81.

Delemarre et al., Repopulation of macrophages in popliteal lymph nodes of mice after liposome-mediated depletion. J Leukoc Biol. 1990;47(3):251-7.

Delgoffe et al., The mTOR kinase differentially regulates effector and regulatory T cell lineage commitment. Immunity. Jun. 19, 2009;30(6):832-44. doi:10.1016/j.immuni.2009.04.014.

Demangel et al., Single chain antibody fragments for the selective targeting of antigens to dendritic cells. Mol Immunol. May 2005;42(8):979-85. Epub Dec. 10, 2004.

Denti et al., Body-wide gene therapy of Duchenne muscular dystrophy in the mdx mouse model. Proc Natl Acad Sci U S A. Mar. 7, 2006;103(10):3758-63. Epub Feb. 24, 2006.

Diethelm-Okita et al., Universal epitopes for human CD4+ cells on tetanus and diphtheria toxins. J Infect Dis. Mar. 2000;181(3):1001-9.

DiLillo et al., B10 cells and regulatory B cells balance immune responses during inflammation, autoimmunity, and cancer. Ann N Y Acad Sci. Jan. 2010;1183:38-57.

Dinarvand et al., Polylactide-co-glycolide nanoparticles for controlled delivery of anticancer agents. Int J Nanomedicine. 2011;6:877-95. doi: 10.2147/IJN.S18905. Epub May 27, 2011.

Dinesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.

Dobrovoskaia et al., Immunological properties of engineered nanomaterials. Nat Nanotechnol. Aug. 2007;2(8):469-78. doi: 10.1038/nnano.2007.223. Epub Jul. 29, 2007. Abstract only.

Dorner et al., Selective expression of the chemokine receptor XCR1 on cross-presenting dendritic cells determines cooperation with CD8+ T cells. Immunity. Nov. 20, 2009;31(5):823-33. Epub Nov. 12, 2009.

Düchs, Dissertation entitled: Effects of Toll-like receptor agonists on the pathogenesis of atopic asthma in mice, University of Würzburg, Sep. 2011. 149 pages.

Eghtesad et al., Effect of rapamycin on immunity induced by vector-mediated dystrophin expression in mdx skeletal muscle. Sci Rep. 2012;2:399. doi: 10.1038/srep00399. Epub May 8, 2012.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.

Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.

Falk et al., Induction and suppression of an autoimmune disease by oligomerized T cell epitopes: enhanced in vivo potency of encephalitogenic peptides. J Exp Med. Feb. 21, 2000;191(4):717-30.

Farr et al., The structure of the sinus wall of the lymph node relative to its endocytic properties and transmural cell passage. Am J Anat. 1980;157(3):265-84.

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.

Fifis et al., Size-dependent immunogenicity: therapeutic and protective properties of nano-vaccines against tumors. J Immunol. Sep. 1, 2004;173(5):3148-54.

Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. DOI: 10.1002/art.27913. 2 pages.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Fourtounas et al., Different immunosuppressive combinations on T-cell regulation in renal transplant recipients. Am J Nephrol. 2010;32(1):1-9. doi:10.1159/000313940. Epub May 20, 2010.

Fraser et al., Nanoparticle therapy for allergic and inflammatory disease. Anti-Inflammatory & Anti-Allergy Agents Med Chem. Mar. 2010;9(1):54-70.

Gaitonde et al., Downregulation of CD40 signal and induction of TGF-β by phosphatidylinositol mediates reduction in immunogenicity against recombinant human Factor VIII. J Pharm Sci. Jan. 2012;101(1):48-55. doi: 10.1002/jps.22746. Epub Sep. 23, 2011.

Gajofatto et al., Treatment strategies for multiple sclerosis: When to start, when to change, when to stop? World J Clin Cases. Jul. 16, 2015;3(7):545-55. doi: 10.12998/wjcc.v3.i7.545.

Gao et al., Contrasting effects of cyclosporine and rapamycin in de novo generation of alloantigen-specific regulatory T cells. Am J Transplant. Jul. 2007;7(7):1722-32. Epub May 19, 2007.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Harnessing nanoparticles for immune modulation. Trends Immunol. Jul. 2015;36(7):419-27.

Getts et al., Microparticles bearing encephalitogenic peptides induce T-cell tolerance and ameliorate experimental autoimmune encephalomyelitis. Nat Biotechnol. Nov. 18, 2012. doi: 10.1038/nbt.2434. [Epub ahead of print].

Giannoukakis et al., Phase I (safety) study of autologous tolerogenic dendritic cells in type 1 diabetic patients. Diabetes Care. Sep. 2011;34(9):2026-32. Epub Jun. 16, 2011.

Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.

Goyenvalle et al., Rescue of dystrophic muscle through U7 snRNA-mediated exon skipping. Science. Dec. 3, 2004;306(5702):1796-9. Epub Nov. 4, 2004.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Gross et al., Fulfilling the dream: tolerogenic dendritic cells to treat multiple sclerosis. Eur J Immunol. Mar. 2012;42(3):569-72. doi: 10.1002/eji.201242402.

(56) References Cited

OTHER PUBLICATIONS

Haddadi et al., Delivery of rapamycin by PLGA nanoparticles enhances its suppressive activity on dendritic cells. J Biomed Mater Res A. Mar. 15, 2008;84(4):885-98.

Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.

Hamdy et al., Part I: targeted particles for cancer immunotherapy. Curr Drug Deliv. May 2011;8(3):261-73.

Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.

Hamdy et al., The immunosuppressive activity of polymeric micellar formulation of cyclosporine A: in vitro and in vivo studies. AAPS J. Jun. 2011;13(2):159-68. doi: 10.1208/s12248-011-9259-8. Epub Feb. 19, 2011.

Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.

Hangartner et al., Antiviral immune responses in gene-targeted mice expressing the immunoglobulin heavy chain of virus-neutralizing antibodies. Proc Natl Acad Sci USA. 2003;100:12883-88.

Harry et al., Generation and characterisation of therapeutic tolerogenic dendritic cells for rheumatoid arthritis. Ann Rheum Dis. Nov. 2010;69(11):2042-50. Epub Jun. 15, 2010.

Hashimoto et al., Stimulation of host NKT cells by synthetic glycolipid regulates acute graft-versus-host disease by inducing Th2 polarization of donor T cells. J Immunol. Jan. 1, 2005;174(1):551-6.

Hassan et al., Major cancer regressions in mesothelioma after treatment with an anti-mesothelin immunotoxin and immune suppression. Sci Transl Med. Oct. 23, 2013;5(208):208ra147. doi: 10.1126/scitranslmed.3006941.

Hawiger et al., Dendritic cells induce peripheral T cell unresponsiveness under steady state conditions in vivo. J Exp Med. 2001;194(6):769-79.

Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. doi: 10.1186/ar4500.

Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.

Ishii, [Allergen-specific immunotherapy utilizing mechanisms for immune regulation]. Nihon Rinsho Meneki Gakkai Kaishi. Oct. 2008;31(5):392-8. Review.

Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.

Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.

Jiang et al., Effects of transient immunosuppression on adeno-associated, virus-mediated, liver-directed gene transfer in rhesus macaques and implications for human gene therapy. Blood. Nov. 15, 2006;108(10):3321-8. Epub Jul. 25, 2006.

Jones, Critically assessing the state-of-the-art in protein structure prediction. Pharmacogenomics J. 2001;1(2):126-34. Review.

Jordan et al., Promotion of B cell immune responses via an alum-induced myeloid cell population. Science. Jun. 18, 2004;304(5678):1808-10.

Junt et al., Subcapsular sinus macrophages in lymph nodes clear lymph-borne viruses and present them to antiviral B cells. Nature. 2007;450:110-4. Supplemental material.

Kang et al., Cutting edge: Immunosuppressant as adjuvant for tolerogenic immunization. J Immunol. Apr. 15, 2008;180(8):5172-6.

Kang et al., Very low-dose tolerance with nucleosomal peptides controls lupus and induces potent regulatory T cell subsets. J Immunol. Mar. 15, 2005;174(6):3247-55.

Kaplan et al., Transient immunosuppression with deoxyspergualin improves longevity of transgene expression and ability to readminister adenoviral vector to the mouse lung. Hum Gene Ther. Jun. 10, 1997;8(9):1095-104.

Karamloo et al., Prevention of allergy by a recombinant multi-allergen vaccine with reduced IgE binding and preserved T cell epitopes. Eur J Immunol. Nov. 2005;35(11):3268-76.

Karrer et al., On the key role of secondary lymphoid organs in antiviral immune responses studied in alymphoplastic (aly/aly) and spleenless (Hox11(−)/−) mutant mice. J Exp Med. 1997;185(12):2157-70.

Katsnelson, Next-generation proteasome inhibitor approved in multiple myeloma. Next-generation proteasome inhibitor approved in multiple myeloma. Nat Biotechnol. Nov. 2012;30(11):1011-2. doi: 10.1038/nbt1112-1011.

Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.

Kim et al., Effects of cyclosporine and rapamycin on immunoglobulin production by preactivated human B cells. Clin Exp Immunol. Jun. 1994;96(3):508-12.

Kim et al., Inhibition of follicular T-helper cells by CD8(+) regulatory T cells is essential for self tolerance. Nature. Sep. 16, 2010;467(7313):328-32.

Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.

Kingsley et al., Transplantation tolerance: lessons from experimental rodent models. Transpl Int. Oct. 2007;20(10):828-41. Epub Aug. 17, 2007.

Kishimoto et al., Improving the efficacy and safety of biologic drugs with tolerogenic nanoparticles. Nat Nanotechnol. Oct. 2016;11(10):890-899. doi:10.1038/nnano.2016.135. Epub Aug. 1, 2016.

Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.

Krieg et al., CpG motifs in bacterial DNA trigger direct B-cell activation. Nature. 1995;374(6522):546-9.

Kunisawa et al., Fusogenic liposome functions as an efficient immunoadjuvant in inducing humoral immune-responses to soluble antigen. Drug Delivery System. Jan. 1998;13(1):21-26.

Kuwabara et al., Insulin biosynthesis in neuronal progenitors derived from adult hippocampus and the olfactory bulb. EMBO Mol Med. Dec. 2011;3(12):742-54. doi: 10.1002/emmm.201100177. Epub Oct. 10, 2011. E-pub verion.

Lanza et al., Transplantation of encapsulated cells and tissues. Surgery. Jan. 1997;121(1):1-9.

Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.

Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013.

(56) References Cited

OTHER PUBLICATIONS

Lipsky et al., Pegloticase immunogenicity: the relationship between efficacy and antibody development in patients treated for refractory chronic gout. Arthritis Res Ther. Mar. 4, 2014;16(2):R60. doi: 10.1186/ar4497.

Liu et al., Origin and development of dendritic cells. Immunol Rev. Mar. 2010;234(1):45-54.

Livingston et al., A rational strategy to design multiepitope immunogens based on multiple Tlymphocyte epitopes. J Immunol. Jun. 1, 2002;168(11):5499-506.

Lloyd, Disulphide reduction in lysosomes. The role of cysteine. Biochem J. Jul. 1, 1986;237(1):271-2.

Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.

Lowenstein, The case for immunosuppression in clinical gene transfer. Mol Ther. Aug. 2005;12(2):185-6.

Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.

Ludewig et al., Induction of optimal anti-viral neutralizing B cell responses by dendritic cells requires transport and release of virus particles in secondary lymphoid organs. Eur J Immunol. 2000;30(1):185-96.

Lund et al., Effector and regulatory B cells: modulators of CD4(+) T cell immunity. Nat Rev Immunol. Apr. 2010;10(4):236-47. Epub Mar. 12, 2010.

Lutsiak et al., Analysis of poly(D,L-lactic-co-glycolic acid) nanosphere uptake by human dendritic cells and macrophages in vitro. Pharm Res. Oct. 2002;19(10):1480-7.

Macary et al., Ovalbumin-specific, MHC class I-restricted, alpha beta-positive, Tc1 and Tc0 CD8+ T cell clones mediate the in vivo inhibition of rat IgE. J Immunol. Jan. 15, 1998;160(2):580-7.

Maher et al., Targeting cytotoxic T lymphocytes for cancer immunotherapy. Br J Cancer. Aug. 31, 2004;91(5):817-21. Review.

Maldonado et al., How tolerogenic dendritic cells induce regulatory T cells. Adv Immunol. 2010;108:111-65. doi: 10.1016/B978-0-12-380995-7.00004-5. Review.

Maldonado et al., Polymeric synthetic nanoparticles for the induction of antigen-specific immunological tolerance. Proc Natl Acad Sci U S A. Jan. 13, 2015;112(2):E156-65. doi: 10.1073/pnas.1408686111. Epub Dec. 29, 2014.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592.

Martin et al., A vector-based minigene vaccine approach results in strong induction of T-cell responses specific of hepatitis C virus. Vaccine. May 12, 2008;26(20):2471-81. Epub Apr. 1, 2008.

Martinez-Pomares et al., Antigen presentation the macrophage way. Cell. Nov. 16, 2007;131(4):641-3.

Martín-Gayo et al., Plasmacytoid dendritic cells resident in human thymus drive natural Treg cell development. Blood. Jul. 1, 2010;115(26):5366-75. Epub Mar. 31, 2010.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

Mason, Functional Analysis of the Cysteine Residues of Activin A. Mol Endocrinol. 1994;8(3):325-32.

Matsui et al., Delivery of full-length factor VIII using a piggyBac transposon vector to correct a mouse model of hemophilia A. PLoS One. Aug. 15, 2014;9(8):e104957. doi: 10.1371/journal.pone.0104957. eCollection 2014.

Matta et al., Tolerogenic plasmacytoid DC. Eur J Immunol. Oct. 2010;40(10):2667-76.

Matteoli et al., Gut CD103+ dendritic cells express indoleamine 2,3-dioxygenase which influences T regulatory/T effector cell balance and oral tolerance induction. Gut. May 2010;59(5):595-604.

Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.

Mazor et al., Immunogenicity of therapeutic recombinant immunotoxins. Immunol Rev. Mar. 2016;270(1):152-64. doi: 10.1111/imr.12390. Review.

McFarland et al., Ovalbumin(323-339) peptide binds to the major histocompatibility complex class II I-A(d) protein using two functionally distinct registers. Biochemistry. Dec. 14, 1999;38(50):16663-70.

McKay et al., A novel anti-inflammatory role of simvastatin in a murine model of allergic asthma. J Immunol. Mar. 1, 2004;172(5):2903-8.

McMahon et al., Epitope spreading initiates in the CNS in two mouse models of multiple sclerosis. Nat Med. Mar. 2005;11(3):335-9. Epub Feb. 27, 2005.

Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015.037.

Mempel et al., T-cell priming by dendritic cells in lymph nodes occurs in three distinct phases. Nature. 2004;427(6970):154-9.

Meng et al., Statins induce the accumulation of regulatory T cells in atherosclerotic plaque. Mol Med. May 9, 2012;18:598-605. doi: 10.2119/molmed.2011.00471.

Menzies et al., Simvastatin does not exhibit therapeutic anti-inflammatory effects in asthma. J Allergy Clin Immunol. Feb. 2007;119(2):328-35. Epub Dec. 4, 2006.

Metelitsa et al., Antidisialoganglioside/granulocyte macrophage-colonystimulating factor fusion protein facilitates neutrophil antibody-dependent cellular cytotoxicity and depends on FcγRII (CD32) and Mac-1 (CD11b/CD18) for enhanced effector cell adhesion and azurophil granule exocytosis. Blood. 2002;99(11):4166-73.

Mine et al., Epitope characterization of ovalbumin in BALB/c mice using different entry routes. Biochim Biophys Acta. Feb. 2007;1774(2):200-12. Epub Dec. 19, 2006.

Mingozzi et al., Modulation of tolerance to the trans gene product in a nonhuman primate model of AAV-mediated gene transfer to liver. Blood. Oct. 1, 2007;110(7):2334-41. Epub Jul. 3, 2007.

Miyara et al., Therapeutic approaches to allergy and autoimmunity based on FoxP3+ regulatory T-cell activation and expansion. J Allergy Clin Immunol. Apr. 2009;123(4):749-55.

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.

Mori et al., Biological drug for refractory juvenile idiopathic arthritis. Clin Rheum. 2006;18(2):191-6.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages.

Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.

Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.

(56) References Cited

OTHER PUBLICATIONS

Nayak et al., Prophylactic immune tolerance induced by changing the ratio of antigen-specific effector to regulatory T cells. J Thromb Haemost. Sep. 2009;7(9):1523-32. doi: 10.1111/j.1538-7836.2009.03548.x. Epub Jul. 6, 2009.
Nepom et al., Challenges in the pursuit of immune tolerance. Challenges in the pursuit of immune tolerance. Immunol Rev. May 2011;241(1):49-62. doi: 10.1111/j.1600-065X.2011.01003.x.
Neuhaus et al., mTOR inhibitors: an overview. Liver Transpl. Jun. 2001;7(6):473-84.
Ngo et al., In The Protein Folding Problem and Tertiary Structure Prediction, 1994. Eds Mertz et al. Birkhauser. Boston, MA. 1994:433,491-5.
Nikolic et al., Plasmacytoid dendritic cells in autoimmune diabetes—potential tools for immunotherapy. Immunobiology. 2009;214(9-10):791-9. Epub Jul. 22, 2009.
Nixon et al., Synthetic peptides entrapped in microparticles can elicit cytotoxic T cell activity. Vaccine. Nov. 1996;14(16):1523-30.
Notter et al., Targeting of a B7-1 (CD80) immunoglobulin G fusion protein to acute myeloid leukemia blasts increases their costimulatory activity for autologous remission T cells. Blood. 2001;97(10):3138-45.
Ochsenbein et al., Control of early viral and bacterial distribution and disease by natural antibodies. Science. 1999;286(5447):2156-9.
Ochsenbein et al., Protective T cell-independent antiviral antibody responses are dependent on complement. J Exp Med. 1999;190(8):1165-74.
Oh et al., CD4+CD25+ regulatory T cells in autoimmune arthritis. Immunol Rev. Jan. 2010;233(1):97-111.
Okada et al., Antigen-engaged B cells undergo chemotaxis toward the T zone and form motile conjugates with helper T cells. PLoS Biol. 2005;3(6):e150. 1047-61.
Omata et al., Ovalbumin-specific IgE modulates ovalbumin-specific T-cell response after repetitive oral antigen administration. J Allergy Clin Immunol. Apr. 2005;115(4):822-7.
Onda et al., Tofacitinib suppresses antibody responses to protein therapeutics in murine hosts. J Immunol. Jul. 1, 2014;193(1):48-55. doi: 10.4049/jimmunol.1400063. Epub Jun. 2, 2014.
O'Neil et al., Extracellular matrix binding mixed micelles for drug delivery applications. J Control Release. Jul. 20, 2009;137(2):146-51. Epub Mar. 27, 2009.
Orban et al., Prevention of Type 1 Diabetes Mellitus using a Novel Vaccine. Ther Adv Endocrinol Metab. Feb. 2011;2(1):9-16.
O'Sullivan et al., Truncation analysis of several DR binding epitopes. J Immunol. Feb. 15, 1991;146(4):1240-6.
Paolicelli et al., Surface-modified PLGA-based nanoparticles that can efficiently associate and deliver virus-like particles. Nanomedicine (Lond). Aug. 2010;5(6):843-53. doi: 10.2217/nnm.10.69.
Pape et al., The humoral immune response is initiated in lymph nodes by B cells that acquire soluble antigen directly in the follicles. Immunity. 2007;26(4):491-502.
Papisov, Acyclic polyacetals from polysaccharides: biomimetic biomedical "stealth" polymers. Chapter 19. ACS Symposium Series. Feb. 15, 2001:786:301-14.
Pastan et al., Immunotoxin therapy of cancer. Nat Rev Cancer. Jul. 2006;6(7):559-65. Review.
Phillips et al., Enhanced antibody response to liposome-associated protein antigens: preferential stimulation of IgG2a/b production. Vaccine. 1992;10(3):151-8.
Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.
Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.
Qadura et al., Reduction of the immune response to factor VIII mediated through tolerogenic factor VIII presentation by immature dendritic cells. J Thromb Haemost. Dec. 2008;6(12):2095-104. Epub Sep. 27, 2008.
Qi et al., Extrafollicular activation of lymph node B cells by antigen-bearing dendritic cells. Science. 2006;312(5780):1672-6.
Quarcoo et al., Resiquimod, a new immune response modifier from the family of imidazoquinolinamines, inhibits allergen-induced Th2 responses, airway inflammation and airway hyper-reactivity in mice. Clin Exp Allergy. Aug. 2004;34(8):1314-20.
Ragni et al., Factor VIII-pulsed dendritic cells reduce anti-factor VIII antibody formation in the hemophilia A mouse model. Exp Hematol. Jun. 2009;37(6):744-54.
Ran et al., In vivo genome editing using *Staphylococcus aureus* Cas9. Nature. Apr. 9, 2015;520(7546):186-91. doi: 10.1038/nature14299. Epub Apr. 1, 2015.
Reddy et al., Detection of autoreactive myelin proteolipid protein 139-151-specific T cells by using MHC II (IAs) tetramers. J Immunol. Jan. 15, 2003;170(2):870-7.
Reddy et al., Exploiting lymphatic transport and complement activation in nanoparticle vaccines. Nat Biotech. 2007;25(10):1159-64.
Reichardt et al., Impact of mammalian target of rapamycin inhibition on lymphoid homing and tolerogenic function of nanoparticle-labeled dendritic cells following allogeneic hematopoietic cell transplantation. J Immunol. Oct. 1, 2008;181(7):4770-9.
Reif et al., Balanced responsiveness to chemoattractants from adjacent zones determines B-cell position. Nature. 2002;416(6876):94-9.
Reinders et al., New advances in the treatment of gout: review of pegloticase. Ther Clin Risk Manag. Oct. 27, 2010;6:543-50. doi: 10.2147/TCRM.S6043.
Renz et al., Comparison of the allergenicity of ovalbumin and ovalbumin peptide 323-339. Differential expansion of V beta-expressing T cell populations. J Immunol. Dec. 15, 1993;151(12):7206-13.
Rice-Ficht et al., Polymeric particles in vaccine delivery. Curr Opin Microbiol. Feb. 2010;13(1):106-12. doi: 10.1016/j.mib.2009.12.001. Epub Jan. 14, 2010. Review.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Robbins et al., Stable expression of shRNAs in human CD34+ progenitor cells can avoid induction of interferon responses to siRNAs in vitro. Nature Biotechnology. 2006;24(5):566-71.
Rossbacher et al., The B cell receptor itself can activate complement to provide the complement receptor 1/2 ligand required to enhance B cell immune responses in vivo. J Exp Med. 2003;198(4):591-602.
Rybak-Smith et al., Complement activation by carbon nanotubes. Adv Drug Deliv Rev. Sep. 16, 2011;63(12):1031-41. doi: 10.1016/j.addr.2011.05.012. Epub Jun. 12, 2011. Review.
Samuel et al., Nanoparticle delivery systems for control of immunity. Proceedings of the 2004 Intl. Conference on MEMS, NANO and Smart Systems (ICMENS '04). IEEE 2004. 3 pages.
Samuel et al., Polymeric nanoparticles for targeted delivery of Therapeutic Vaccines to dendritic cells. Proceedings of the International Conference on MEMS, NANO and Smart Systems. (ICMENS '03). IEEE 2003. 5 pages.
Sato et al., Induction of immunotolerance by the application of chase-sulzberger effect. JP J Translpant. 1995;30(3):231-9.
Sato et al., Prolongation of the immunosuppression by repeated injections of donor antigen via the portal vein. JP J Transplant. 1995;30(2):149-54.
Sbiera et al., Influence of short-term glucocorticoid therapy on regulatory T cells in vivo. PLoS One. 2011;6(9):e24345. doi: 10.1371/journal.pone.0024345. Epub Sep. 2, 2011.
Scardino et al., A polyepitope DNA vaccine targeted to Her-2/ErbB-2 elicits a broad range of human and murine CTL effectors to protect against tumor challenge. Cancer Res. Jul. 15, 2007;67(14):7028-36.
Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.
Seffernick et al., Melamine deaminase and atrazine chlorohydrolase: 98 percent identical but functionally different. J Bacteriol. Apr. 2001;183(8):2405-10.

(56) References Cited

OTHER PUBLICATIONS

Senís et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014. Supporting Information. 26 pages.
Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.
Shen et al., Combined effect of cyclosporine and sirolimus on improving the longevity of recombinant adenovirus-mediated transgene expression in the retina. Arch Ophthalmol. Jul. 2001;119(7):1033-43.
Shen et al., Enhanced and prolonged cross-presentation following endosomal escape of exogenous antigens encapsulated in biodegradable nanoparticles. Immunol. 2006;117:78-88.
Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.
Shiow et al., CD69 acts downstream of interferon-alpha/beta to inhibit S1P1 and lymphocyte egress from lymphoid organs. Nature. Mar. 23, 2006;440(7083):540-4. Epub Mar. 8, 2006.
Shortman et al., Steady-state and inflammatory dendritic-cell development. Nat Rev Immunol. Jan. 2007;7(1):19-30. Epub Dec. 15, 2006.
Skolnick et al., From genes to protein structure and function: novel applications of computational approaches in the genomic era. Trends Biotechnol. Jan. 2000;18(1):34-9. Review.
Sondel et al., Preclinical and clinical development of immunocytokines. Curr Opin Investig Drugs. 2003;4(6):696-700.
Soroosh et al., Th9 and allergic disease. Immunology. Aug. 2009;127(4):450-8. doi: 10.1111/j.1365-2567.2009.03114.x.
Srinivasan et al., Prediction of class I T-cell epitopes: evidence of presence of immunological hot spots inside antigens. Bioinformatics. Aug. 4, 2004;20 Suppl 1:i297-302.
Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.
Stepkowski et al., Inhibition of host-versus-graft and graft-versus-host responses after small bowel transplantation in rats by rapamycin. Transplantation. Feb. 1992;53(2):258-64.
Storm et al., Surface Modification of Nanoparticles to Oppose Uptake by the Mononuclear Phagocyte System. Adv Drug Deliv Rev. 1995;17:31-48.
Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.
Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.
Tang et al., Adenovirus hexon T-cell epitope is recognized by most adults and is restricted by HLA DP4, the most common class II allele. Gene Ther. Sep. 2004;11(18):1408-15.
Tardieu et al., Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. Jun. 2014;25(6):506-16. doi: 10.1089/hum.2013.238. Epub May 5, 2014.
Tarlinton et al., Antigen to the node: B cells go native. Immunity. Apr. 2007;26(4):388-90.
Tarzi et al., Peptide immunotherapy for allergic disease. Expert Opin Biol Ther. Jul. 2003;3(4):617-26. Review.
Taylor et al., Macrophage receptors and immune recognition. Annu Rev Immunol. 2005;23:901-44.
Thomson et al., Immunoregulatory functions of mTOR inhibition. Nat Rev Immunol. May 2009;9(5):324-37. doi: 10.1038/nri2546.
Tosatto et al., Large-scale prediction of protein structure and function from sequence. Curr Pharm Des. 2006;12(17):2067-86. Review.
Tuohy, Peptide determinants of myelin proteolipid protein (PLP) in autoimmune demyelinating disease: a review. Neurochem Res. Aug. 1994;19(8):935-44.
Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.
Unkeless et al., Structure and function of human and murine receptors for IgG. Annu Rev Immunol. 1998;6:251-81.
Vascotto et al., Antigen presentation by B lymphocytes: how receptor signaling directs membrane trafficking. Curr Opin Immunol. 2007;19(1):93-8.
Velluto et al., PEG-b-PPS diblock copolymer aggregates for hydrophobic drug solubilization and release: cyclosporin A as an example. Mol Pharm. Jul.-Aug. 2008;5(4):632-42. Epub Jun. 12, 2008.
Vila et al., Regulatory T cells and autoimmunity. Curr Opin Hematol. Jul. 2009;16(4):274-9.
Villadangos et al., Found in translation: the human equivalent of mouse CD8+ dendritic cells. J Exp Med. Jun. 7, 2010;207(6):1131-4. Epub May 31, 2010.
Von Andrian et al., Homing and cellular traffic in lymph nodes. Nat Rev Immunol. 2003;3(11):867-78.
Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.
Wang et al., Blood mononuclear cells induce regulatory NK T thymocytes in anterior chamber-associated immune deviation. J Leukoc Biol. May 2001;69(5):741-6.
Wang et al., Sustained AAV-mediated dystrophin expression in a canine model of Duchenne muscular dystrophy with a brief course of immunosuppression. Mol Ther. Jun. 2007;15(6):1160-6. Epub Apr. 10, 2007.
Weber et al., T cell epitope: friend or foe? Immunogenicity of biologies in context. Adv Drug Deliv Rev. Sep. 30, 2009;61(11):965-76. Epub Jul. 18, 2009.
Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.
Wessels et al., Studies of group B streptococcal infection in mice deficient in complement component C3 or C4 demonstrate an essential role for complement in both innate and acquired immunity. Proc Natl Acad Sci USA. 1995;92(25):11490-4.
Witkowski et al., Conversion of a beta-ketoacyl synthase to a malonyl decarboxylase by replacement of the active-site cysteine with glutamine. Biochemistry. Sep. 7, 1999;38(36):11643-50.
Wu et al., Humanization of a murine monoclonal antibody by simultaneous optimization of framework and CDR residues. J Mol Biol. Nov. 19, 1999;294(1):151-62.
Yamaguchi et al., Around hematological malignancies. Trends in Hematological Malignancies. 2010;2(2):96-98.
Yamaki et al., Preventive and therapeutic effects of rapamycin, a mammalian target of rapamycin inhibitor, on food allergy in mice. Allergy. Oct. 2012;67(10):1259-70. doi: 10.1111/all.12000. Epub Aug. 23, 2012.
Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. Epub Jun. 27, 2012.
Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.
Zhang, Introduction to basic medicine. China University of Science and Technology Press. Aug. 31, 2012:423.
Zhang et al., Induction of tolerance to FVIII using nanoparticles in a murine model of hemophilia A. Blood. Nov. 15, 2013;122:2337.
Zhang et al., The mechanism of B lymphocytes in inducing immune tolerance. Immunol J. Jul. 2010;26(7):643-6.

(56) References Cited

OTHER PUBLICATIONS

Zhang-Hoover et al., Tolerogenic APC generate CD8+ T regulatory cells that modulate pulmonary interstitial fibrosis. J Immunol. Jan. 1, 2004;172(1):178-85.
Zheng et al., How antigen quantity and quality determine T-cell decisions in lymphoid tissue. Mol Cell Biol. Jun. 2008;28(12):4040-51. Epub Apr. 21, 2008.
Zhou et al., Updates of mTOR inhibitors. Anticancer Agents Med Chem. Sep. 2010;10(7):571-81.
Zhu et al., T cell epitope mapping of ragweed pollen allergen Ambrosia artemisiifolia (Amb a 5) and Ambrosia trifida (Amb t 5) and the role of free sulfhydryl groups in T cell recognition. J Immunol. Nov. 15, 1995;155(10):5064-73.
Zweers, Biodegradable nanoparticles of intravascular drug delivery. Unversiteit Twente, 2003.
Abeles, PEG-ing down (and preventing?) the cause of pegloticase failure. Arthritis Res Ther. May 30, 2014;16(3):112. doi: 10.1186/ar4572.
Dupont et al., The evolving role of sirolimus in renal transplantation. QJM. Jun. 2003;96(6):401-9. Review.
Garay et al., Therapeutic perspectives on uricases for gout. Joint Bone Spine. May 2012;79(3):237-42. doi: 10.1016/j.jbspin.2012.01.004. Epub Feb. 25, 2012. Review.
Heidt et al., Effects of immunosuppressive drugs on purified human B cells: evidence supporting the use of MMF and rapamycin. Transplantation. Nov. 2008;86(9):1292-1300. doi: 10.1097/TP.0b013e3181874a36.
Horibe et al., Rapamycin-conditioned, alloantigen-pulsed dendritic cells promote indefinite survival of vascularized skin allografts in association with T regulatory cell expansion. Transplant Immunol. Feb. 2008;18(4):307-318. doi: 10.1016/j.trim.2007.10.007.
Hushmendy et al., Select phytochemicals suppress human T-lymphocytes and mouse splenocytes suggesting their use in autoimmunity and transplantation. Nutr Res. Aug. 2009;29(8):568-78. doi: 10.1016/j.nutres.2009.08.003. PubMed PMID: 19761891.
Ming et al. Medical Immunology. Yunnan University Press. Feb. 28, 2009. p. 40-41.
Perez-Ruiz et al., Lesinurad in combination with allopurinol: results of a phase 2, randomised, double-blind study in patients with gout with an inadequate response to allopurinol. Ann Rheum Dis. Jun. 2016;75(6):1074-80. doi:10.1136/annrheumdis-2015-207919. Epub Jan. 7, 2016. PubMed PMID: 26742777; PubMed Central PMCID: PMC4893096.
Sundy et al., Reduction of plasma urate levels following treatment with multiple doses of pegloticase (polyethylene glycol-conjugated uricase) in patients with treatment-failure gout: results of a phase II randomized study. Arthritis Rheum. Sep. 2008;58(9):2882-91. doi: 10.1002/art.23810.
Ulivieri et al., Simvastatin impairs humoral and cell-mediated immunity in mice by inhibiting lymphocyte homing, T-cell activation and antigen cross-presentation. Eur J Immunol. Oct. 2008;38(10):2832-44. doi: 10.1002/eji.200838278. PubMed PMID: 18958884.
Vogt et al., Urate oxidase (rasburicase) for treatment of severe tophaceous gout. Nephrol Dial Transplant. Feb. 2005;20(2):431-3.
Chandler et al., Liver-directed adeno-associated virus serotype 8 gene transfer rescues a lethal murine model of citrullinemia type 1. Gene Ther. Dec. 2013;20(12):1188-91. doi: 10.1038/gt.2013.53. Epub Oct. 17, 2013.
De Sabbata et al., Development of a novel AAV vector in combination with tolerogenic nanoparticles for the treatment of ornithine transcarbamylase deficiency. Human Gene Ther. 2017; 28(12): A71. Abstract P197.
U.S. Appl. No. 15/061,204, filed Mar. 4, 2016, Kishimoto et al.
Antignani et al., Chemical Screens Identify Drugs that Enhance or Mitigate Cellular Responses to Antibody-Toxin Fusion Proteins. PLoS One. Aug. 24, 2016;11(8):e0161415. doi: 10.1371/journal.pone.0161415. eCollection 2016. PubMed PMID: 27556570; PubMed Central PMCID: PMC4996465.

Avramis et al., Asparaginase (native ASNase or pegylated ASNase) in the treatment of acute lymphoblastic leukemia. Int J Nanomedicine. 2006;1(3):241-54. Review. PubMed PMID: 17717965; PubMed Central PMCID: PMC2426805.
Bauss et al., Characterization of a re-engineered, mesothelin-targeted Pseudomonas exotoxin fusion protein for lung cancer therapy. Mol Oncol. Oct. 2016;10(8):1317-29. doi: 10.1016/j.molonc.2016.07.003. Epub Jul. 14, 2016. PubMed PMID: 27507537; PubMed Central PMCID: PMC5423209.
Becker et al., Febuxostat compared with allopurinol in patients with hyperuricemia and gout. N Engl J Med. Dec. 8, 2005;353(23):2450-61. PubMed PMID: 16339094.
Bell et al., Analysis of tumors arising in male B6C3F1 mice with and without AAV vector delivery to liver. Mol Ther. Jul. 2006;14(1):34-44. Epub May 6, 2006.
CAS Registry No. 1841500-93-3. LMB-100 Substance. 2020.
Chung et al., Cetuximab-induced anaphylaxis and IgE specific for galactose-alpha-1,3-galactose. N Engl J Med. Mar. 13, 2008;358(11):1109-17. doi: 10.1056/NEJMoa074943. PubMed PMID: 18337601; PubMed Central PMCID: PMC2361129.
Cuburu et al., Intravaginal immunization with HPV vectors induces tissue-resident CD8+ T cell responses. J Clin Invest. Dec. 2012;122(12):4606-20. doi: 10.1172/JCI63287. Epub Nov. 12, 2012. PubMed PMID: 23143305; PubMed Central PMCID: PMC3533540.
Cunningham et al., Induction and prevention of severe hyperammonemia in the spfash mouse model of ornithine transcarbamylase deficiency using shRNA and rAAV-mediated gene delivery. Mol Ther. May 2011;19(5):854-9. doi: 10.1038/mt.2011.32. Epub Mar. 8, 2011.
Dreaden et al., Size matters: gold nanoparticles in targeted cancer drug delivery. Ther Deliv. Apr. 2012;3(4):457-78. Review. PubMed PMID: 22834077; PubMed Central PMCID: PMC3596176.
Gordon, Ornithine transcarbamylase deficiency: a urea cycle defect. Eur J Paediatr Neurol. 2003;7(3):115-21. Review.
Guo et al., PD-1 blockade and OX40 triggering synergistically protects against tumor growth in a murine model of ovarian cancer. PLoS One. Feb. 27, 2014;9(2):e89350. doi: 10.1371/journal.pone.0089350. eCollection 2014. Erratum in: PLoS One. Oct. 18, 2017;12 (10 ):e0186965. PubMed PMID: 24586709; PubMed Central PMCID: PMC3937343.
Hassan et al., Phase 1 study of the antimesothelin immunotoxin SS1P in combination with pemetrexed and cisplatin for front-line therapy of pleural mesothelioma and correlation of tumor response with serum mesothelin, megakaryocyte potentiating factor, and cancer antigen 125. Cancer. Nov. 1, 2014;120(21):3311-9. doi: 10.1002/cncr.28875. Epub Jul. 2, 2014. PubMed PMID: 24989332.
Hassan et al., Phase I study of SS1P, a recombinant anti-mesothelin immunotoxin given as a bolus I.V. infusion to patients with mesothelin-expressing mesothelioma, ovarian, and pancreatic cancers. Clin Cancer Res. Sep. 1, 2007;13(17):5144-9. PubMed PMID: 17785569.
Hassan et al., Pretreatment with rituximab does not inhibit the human immune response against the immunogenic protein LMB-1. Clin Cancer Res. Jan. 1, 2004 ;10(1 Pt 1):16-8. PubMed PMID:14734446.
Hollevoet et al., In vitro and in vivo activity of the low-immunogenic antimesothelin immunotoxin RG7787 in pancreatic cancer. Mol Cancer Ther. Aug. 2014;13(8):2040-9. doi: 10.1158/1535-7163.MCT-14-0089-T. Epub Jun. 13, 2014. Erratum in: Mol Cancer Ther. Jul. 2015;14(7):1763. PubMed PMID: 24928849; PubMed Central PMCID: PMC4142475.
Jing et al., Comparison of immunosuppressive effects and ND4 expression among different immunosuppressive strategies following AAV2-ND4 gene treatment for leber hereditary optic neuropathy. Acta Med Univ Sci Technol Huazhong. Apr. 2013; 42(2):187-191.
Koerber et al., Molecular evolution of adeno-associated virus for enhanced glial gene delivery. Mol Ther. Dec. 2009;17(12):2088-95. doi: 10.1038/mt.2009.184. Epub Aug. 11, 2009. PubMed PMID: 19672246; PubMed Central PMCID: PMC2788045.
Kreitman et al., Phase I trial of anti-CD22 recombinant immunotoxin moxetumomab pasudotox (CAT-8015 or HA22) in patients with hairy cell leukemia. J Clin Oncol. May 20, 2012;30(15):1822-8. doi: 10.1200/JCO.2011.38.1756. Epub Feb. 21, 2012. PubMed PMID: 22355053; PubMed Central PMCID: PMC3383181.

(56) References Cited

OTHER PUBLICATIONS

Kreitman et al., Phase I trial of continuous infusion anti-mesothelin recombinant immunotoxin SS1P. Clin Cancer Res. Aug. 15, 2009;15(16):5274-9. doi: 10.1158/1078-0432.CCR-09-0062. Epub Aug. 11, 2009. PubMed PMID: 19671873; PubMed Central PMCID: PMC2754261.

Kreitman et al., Phase I trial of recombinant immunotoxin anti-Tac(Fv)-PE38 (LMB-2) in patients with hematologic malignancies. J Clin Oncol. Apr. 2000;18(8):1622-36. PubMed PMID: 10764422.

Kreitman et al., Phase I trial of recombinant immunotoxin RFB4(dsFv)-PE38 (BL22) in patients with B-cell malignancies. J Clin Oncol. Sep. 20, 2005;23(27):6719-29. Epub Aug. 1, 2005. PubMed PMID: 16061911.

Kreitman, Recombinant immunotoxins for the treatment of chemoresistant hematologic malignancies. Curr Pharm Des. 2009;15(23):2652-64. Review. PubMed PMID: 19689336.

Law. Rapamycin: an anti-cancer immunosuppressant? Crit Rev Oncol Hematol. Oct. 2005;56(1):47-60. Review. PubMed PMID: 16039868.

Leshem et al., Combining Local Immunotoxins Targeting Mesothelin with CTLA-4 Blockade Synergistically Eradicates Murine Cancer by Promoting Anticancer Immunity. Cancer Immunol Res. Aug. 2017;5(8):685-694. doi: 10.1158/2326-6066.CIR-16-0330. Epub Jul. 3, 2017. PubMed PMID: 28674083; PubMed Central PMCID: PMC5549555.

Liu et al., Recombinant immunotoxin engineered for low immunogenicity and antigenicity by identifying and silencing human B-cell epitopes. Proc Natl Acad Sci U S A. Jul. 17, 2012;109(29):11782-7. doi: 10.1073/pnas.1209292109. Epub Jul. 2, 2012. PubMed PMID: 22753489; PubMed Central PMCID: PMC3406843.

Maeda, Tumor-selective delivery of macromolecular drugs via the EPR effect: background and future prospects. Bioconjug Chem. May 19, 2010;21(5):797-802. doi: 10.1021/bc100070g. Review. PubMed PMID: 20397686.

Manoli et al., FGF21 underlies a hormetic response to metabolic stress in methylmalonic acidemia. JCI Insight. Dec. 6, 2018;3(23). pii:124351. doi: 10.1172/jci.insight.124351.

Maus et al., T cells expressing chimeric antigen receptors can cause anaphylaxis in humans. Cancer Immunol Res. Jul. 2013;1:26-31. PubMed PMID: 24432303; PubMed Central PMCID: PMC3888798.

Mazor et al., Elimination of murine and human T-cell epitopes in recombinant immunotoxin eliminates neutralizing and anti-drug antibodies in vivo. Cell Mol Immunol. May 2017;14(5):432-442. doi: 10.1038/cmi.2015.91. Epub Oct. 19, 2015. PubMed PMID: 26477977; PubMed Central PMCID: PMC5423085.

Mezzapelle et al., Human malignant mesothelioma is recapitulated in immunocompetent BALB/c mice injected with murine AB cells. Sci Rep. Mar. 10, 2016;6:22850. doi: 10.1038/srep22850. PubMed PMID: 26961782; PubMed Central PMCID: PMC4785401.

Mossoba et al., Pentostatin plus cyclophosphamide safely and effectively prevents immunotoxin immunogenicity in murine hosts. Clin Cancer Res. Jun. 1, 2011;17(11):3697-705. doi: 10.1158/1078-0432.CCR-11-0493. Epub Apr. 26, 2011. PubMed PMID: 21521777; PubMed Central PMCID: PMC3107891.

O'Donnell et al., PI3K-AKT-mTOR inhibition in cancer immunotherapy, redux. Semin Cancer Biol. Feb. 2018;48:91-103. doi:10.1016/j.semcancer.2017.04.015. Epub May 2, 2017. Review. PubMed PMID: 28467889.

Pandey et al., Photochemical linking of primary aromatic mines to carrier proteins to elicit antibody response against the mine haptens. J Immunol Methods. Nov. 20, 1986;94(1-2):237-46.

Pastan, Discovery of mesothelin and exploiting it as a target for immunotherapy. Cancer Res. Jun. 1, 2014;74(11):2907-12. doi:10.1158/0008-5472.CAN-14-0337. Epub May 13, 2014. Review. PubMed PMID: 24824231; PubMed Central PMCID: PMC4062095.

Piconese et al., OX40 triggering blocks suppression by regulatory T cells and facilitates tumor rejection. J Exp Med. Apr. 14, 2008;205(4):825-39. doi: 10.1084/jem.20071341. Epub Mar. 24, 2008. Erratum in: J Exp Med. Jun. 9, 2008;205(6):1505. PubMed PMID: 18362171; PubMed Central PMCID:PMC2292222.

Ronzitti et al., A translationally optimized AAV-UGT1A1 vector drives safe and long-lasting correction of Crigler-Najjar syndrome. Mol Ther Methods Clin Dev. Jul. 20, 2016;3:16049. eCollection 2016.

Schlesinger et al., Treatment of chronic gouty arthritis: it is not just about urate-lowering therapy. Semin Arthritis Rheum. Oct. 2012;42(2):155-65. doi:10.1016/j.semarthrit.2012.03.010. Epub Apr. 26, 2012. Review. PubMed PMID:22542277.

Selby et al., Anti-CTLA-4 antibodies of IgG2a isotype enhance antitumor activity through reduction of intratumoral regulatory T cells. Cancer Immunol Res. Jul. 2013;1(1):32-42. doi: 10.1158/2326-6066.CIR-13-0013. Epub Apr. 7, 2013. PubMed PMID: 24777248.

Setiady et al., In vivo depletion of CD4+FOXP3+ Treg cells by the PC61 anti-CD25 monoclonal antibody is mediated by FcgammaRIII+ phagocytes. Eur J Immunol. Mar. 2010;40(3):780-6. doi: 10.1002/eji.200939613. PubMed PMID: 20039297.

Stallone et al., mTOR inhibitors effects on regulatory T cells and on dendritic cells. J Transl Med. May 31, 2016;14(1):152. doi: 10.1186/s12967-016-0916-7. Review. PubMed PMID: 27245075; PubMed Central PMCID: PMC4886438.

Sun et al., Immunogenic issues concerning recombinant adeno-associated virus vectors for gene therapy. Curr Gene Ther. Dec. 2002;2(4):485-500. Review. PubMed PMID: 12477257.

Sundy et al., Efficacy and tolerability of pegloticase for the treatment of chronic gout in patients refractory to conventional treatment: two randomized controlled trials. JAMA. Aug. 17, 2011;306(7):711-20. doi:10.1001/jama.2011.1169. PubMed PMID: 21846852.

Sundy et al., Pharmacokinetics and pharmacodynamics of intravenous PEGylated recombinant mammalian urate oxidase in patients with refractory gout. Arthritis Rheum. 2007 ar;56(3):1021-8. Erratum in: Arthritis Rheum. Apr. 2007;56(4):1370. PubMed PMID: 17328081.

Tange et al., The antineoplastic drug Paclitaxel has immunosuppressive properties that can effectively promote allograft survival in a rat heart transplant model. Transplantation. Jan. 27, 2002;73(2):216-23.

Velazquez et al., Effective Depletion of Pre-existing Anti-AAV Antibodies Requires Broad Immune Targeting. Mol Ther Methods Clin Dev. Jan. 25, 2017;4:159-168. doi: 10.1016/j.omtm.2017.01.003. eCollection Mar. 17, 2017. PubMed PMID: 28345001; PubMed Central PMCID: PMC5363314.

Vilar et al., Pushing the envelope in the mTOR pathway: the second generation of inhibitors. Mol Cancer Ther. Mar. 2011;10(3):395-403. doi: 10.1158/1535-7163.MCT-10-0905. Epub Jan. 7, 2011.

Wang et al., Preclinical evaluation of a clinical candidate AAV8 vector for ornithine transcarbamylase (OTC) deficiency reveals functional enzyme from each persisting vector genome. Mol Genet Metab. Feb. 2012;105(2):203-11. doi:10.1016/j.ymgme.2011.10.020. Epub Nov. 7, 2011.

Weng et al., The toxin component of targeted anti-tumor toxins determines their efficacy increase by saponins. Mol Oncol. Jun. 2012;6(3):323-32. doi: 10.1016/j.molonc.2012.01.004. Epub Jan. 24, 2012. PubMed PMID: 22309811; PubMed Central PMCID: PMC5528334.

Yanwei et al., High-efficiency targeted editing of large viral genomes by RNA-guided nucleases. PLoS Pathog. May 1, 2014;10(5):e1004090. doi: 10.1371/journal.ppat.1004090. eCollection May 2014.

Youn et al., Subsets of myeloid-derived suppressor cells in tumor-bearing mice. J Immunol. Oct. 15, 2008;181(8):5791-802. PubMed PMID: 18832739; PubMed Central PMCID: PMC2575748.

Youn et al., The biology of myeloid-derived suppressor cells: the blessing and the curse of morphological and functional heterogeneity. Eur J Immunol. Nov. 2010;40(11):2969-75. doi: 10.1002/eji.201040895. Review. PubMed PMID: 21061430; PubMed Central PMCID:PMC3277452.

Zhang et al., Tolerogenic nanoparticles to induce immunologic tolerance: Prevention and reversal of FVIII inhibitor formation. Cell Immunol. Mar. 2016;301:74-81. doi: 10.1016/j.cellimm.2015.11.004. Epub Dec. 11, 2015. PubMed PMID: 26687613.

[No Author Listed] 3SBio Inc. Exclusively Licenses Pegsiticase (Uricase PEG-20) to Selecta Biosciences to Develop Drug Candidate to Treat Gout. Cision PR Newswire. Jun. 18, 2014.

(56) References Cited

OTHER PUBLICATIONS

[No Author Listed] Highlights of Prescribing Information, Krystexxa (pegloticase). Apr. 2012, pp. 1-14. Retrieved from https://www.accessdata.fda.gov/drugsatfda_docs/label/2012/125293s0341b1.pdf.

Aldhamen et al., Immune recognition of gene transfer vectors: focus on adenovirus as a paradigm. Frontiers in Immunology. 2011 ;2:40. DOI: 10.3389/fimmu.2011.00040.

Azeem et al., 11 Initial Phase 2 Clinical Data of SEL-212 in Symptomatic Gout Patients: Monthly Dosing of a Pegylated Uricase (Pegadricase) with Svp-Rapamycin Enables Sustained Reduction of Acute Gout Flares. Arthritis Rheumatol., Oct. 22, 2018. Retrieved from the Internet https://acrabstracts.org/abstract/initial-phase-2-clinical-data-of-sel-212-in-symptomatic-gout-patients-monthly-dosing-ofa-pegylated-uricase-pegadricase-with-svp-rapamycin-enables-sustained-reduction-of-acute-gout-flares/.

Biosis, Accession No. 2011:426302. Blood, 2010, vol. 116, No. 21:1541, STN [online], retrieved on Mar. 19, 2021.

Chandler et al., Anc80 and SVP Rapamycin: A novel approach to AAV gene therapy for methylmalonic acidemia. Human Gene Therapy. Jan. 1, 2017;28:A70.

Czock et al., Pharmacokinetics and pharmacodynamics of systemically administered glucocorticoids. Clin Pharmacokinet. 2005;44(1):61-98. doi: 10.2165/00003088-200544010-00003.

Davis et al., Hypouricaemic effect of polyethyleneglycol modified urate oxidase. Lancet. Aug. 8, 1981;2(8241):281-3. doi: 10.1016/s0140-6736(81)90528-6. PMID: 6114326.

Dehaan et al., Monthly Dosing of InmTOR Tolerogenic Nanoparticles Combined with Pegylated Uricase (Pegadricase) Mitigates Formation of Anti-Drug Antibodies Resulting in Sustained Uricas. American College of Rheumatology (ACR) and Association for Rheumatology Professionals (ARP) Annual Meeting, Nov. 1, 2019 (Nov. 1, 2019) Retrieved from the Internet https://acrabstracts.org/abstract/monthly-dosing-of-inmtor-tolerogenic-nanoparticles-combined-with-pegylated-uricase-pegadricase-mitigates-formation-of-anti-drug-antibodies-resulting-in-sustained-uricase-activity-in-symptomatic-gout/.

Fraser, Nanoparticle Therapy for Allergic and Inflammatory Disease. Anti-Inflammatory & Anti-Allergy Agents in Medicinal Chemistry (2010) 9:54. https://doi.org/10.2174/187152310790711683.

Hao, Rehabilitation Guidelines for Kidney Transplant. Tianjin Science & Tehcnology Translation & Publishing Co., Ltd. Jun. 2006. p. 43.

Horisawa et al., Prolonged anti-inflammatory action of DL-lactide/glycolide copolymer nanospheres containing betamethasone sodium phosphate for an intra-articular delivery system in antigen-induced arthritic rabbit. Pharm Res. Apr. 2002;19(4):403-10. doi: 10.1023/a:1015123024113. PMID: 12033371.

Ilyinskii et al., Combination of an engineered AAV vector Anc80 and tolerogenic nanoparticles encapsulating rapamycin enables efficient transgene expression in mice with pre-existing neutralizing antibodies and provides a therapeutic benefit in a mouse model of methylmalonic acidemia. Changing The Face Of Modern Medicine: Stem Cell And Gene Therapy. 29 (12). Dec. 13, 2018, A168. DOI: 10.1089/hum.2018.29077.abstracts p. P491.

Ilyinskii et al., ImmTOR Tolerogenic Nanoparticles Enhance Transgene Expression after Both Initial and Repeat Dosing in a Mouse Model of Methylmalonic Acidemia Treated with an Anc80 AAV Vector. ASGCT 22nd Annual Meeting. 27(4S1);Apr. 12, 2019:14-15.

Ilyinskii et al., Tolerogenic ImmTOR™ Nanoparticles Enhance Vector Transduction, mRNA Synthesis and Transgene Expression after Initial and Repeated Administrations of AAV-Based Gene Therapy Vectors through Immunological and Non-Immunological Mechanisms. Mol Ther. Apr. 2019;29:77-78.

Ilyinskii et al., Tolerogenic nanoparticles enhance transgene expression and intracellular vector copy number after initial and repeated administrations of AAV-based gene therapy vectors through immunological and non-immunological mechanisms. CNS Neuroscience & Therapeutics. 29(12), Dec. 13, 2018:A153.

Jiang et al., Rapamycin enhances adenovirus-mediated cancer imaging and therapy in pre-immunized murine hosts. PLoS One. Sep. 2, 2013;8(9):e73650. doi: 10.1371/journal.pone.0073650. PMID: 24023896; PMCID: PMC3759448.

Kishimoto, Development of ImmTOR Tolerogenic Nanoparticles for the Mitigation of Anti-drug Antibodies. Front Immunol. May 20, 2020;11:969. doi: 10.3389/fimmu.2020.00969.

Kontos et al., Engineering antigens for in situ erythrocyte binding induces T-cell deletion. Proc Natl Acad Sci U S A. Jan. 2, 2013;110(1):E60-8. doi: 10.1073/pnas.1216353110. Epub Dec. 17, 2012. PMID: 23248266; PMCID: PMC3538192.

Krensky et al., Immunosuppressants, Tolerogens, and Immunostimulants. In: Goodman and Gilman's The Pharmacological Basis of Therapeutics 12th Edition. Chapter 35. Ed.: Laurence L. Brunton. McGraw Hill Medical. 2011.

Marwa et al., Type IV Hypersensitivity Reaction. Aug. 14, 2021. In: StatPearls [Internet]. Treasure Island (FL): StatPearls Publishing; Jan. 2021. PMID: 32965899.

Meliani et al., Antigen-selective modulation of AAV immunogenicity with tolerogenic rapamycin nanoparticles enables successful vector re-administration. Nat Commun. Oct. 5, 2018;9(1):4098. doi: 10.1038/s41467-018-06621-3.

Mikuls, Antihyperuricemic Agents. Section: Uricases. Chapter 65 in Kelley's Textbook of Rheumatology (Ninth ed.). 2013:1001-1003.

Nayak et al., Progress and prospects: immune responses to viral vectors. Gene Ther. Mar. 2010;17(3):295-304. doi: 10.1038/gt.2009.148. Epub Nov. 12, 2009. Erratum in: Gene Ther. Feb. 2010;17(2):294.

Qiu et al., Impact of natural IgM concentration on gene therapy with adenovirus type 5 vectors. J Virol. Mar. 2015;89(6):3412-6. doi: 10.1128/JVI.03217-14. Epub Dec. 31, 2014. PMID: 25552715.

Sands et al., Session Title: Metabolic and Crystal Arthropathies Poster II Session Type: ACR Poster Session C Initial Phase 2 Clinical Data of SEL-212 in Symptomatic Gout Patients: Monthly Dosing of a Pegylated Uricase (Pegsiticase) with Svp-Rapamycin Enables Sustained Reduction of Serum Uric Acid Levels By Mitig 11, Sep. 18, 2017 (Sep. 18, 2017). Retrieved from https://acrabstracts.org/abstract/initial-phase-2-clinical-data-of-sel-212-in-sy mptomatic-gout-patients-monthly-dosing-ofa-pegylated-uricase-pegsiticase-with-svp-rapamycin-enables-sustained-reduction-of-serum-uric-acid-levels-by-m/ on Sep. 14, 2020.

Smolinksi, SAT0402 SEL-212 Phase 2 Clinical Study In Symptomatic Gout Patients: Immtor Tolerogenic Nanoparticles Combined With Pegadricase Mitigates Immunogenicity And Enables Sustained Reduction Of Serum Uric Acid Levels, Low Rate Of Gout Flares And Monthly Dosing. Annals Rheum Dis. Jun. 2019;78(Suppl 2):1288-1289.

Zou et al., Rapamycin-loaded nanoparticles for inhibition of neointimal hyperplasia in experimental vein grafts. Ann Vasc Surg. 2011;25(4):538-546. doi:10.1016/j.avsg.2011.01.003.

[No Author Listed] Cirrhosis. Mayo Clinic. Accessed from <https://www.mayoclinic.org/diseases-conditions/cirrhosis/symptoms-causes/syc-20351487?p=1> on Dec. 14, 2022. 4 pages.

[No Author Listed] History of Changes for Study: NCT02648269; Safety and Pharmacodynamics of SEL-212 (Pegsiticase + SEL-110) in Subjects With Elevated Blood Uric Acid Levels. Jan. 6, 2016. Accessed Jan. 25, 2023 from <https://clinicaltrials.gov/ct2/history/NCT02648269?V_1=View#StudyPageTop>.

[No Author Listed] Mammal. Wikipedia. Retrieved from <https://en.wikipedia.org/wiki/Mammal> on Aug. 31, 2022. 49 pages.

[No Author Listed] The Five Kingdoms of Life. Retrieved from <https://www2.palomar.edu/users/warmstrong/trfeb98.htm> on Apr. 8, 2021. 18 pages.

[No Author Listed], An Open Label Phase II Multiple Dose Safety, Pharmacokinetic and Pharmacodynamics Study of SEL-212 Followed by Open Label Administration of SEL-037 in Subjects with Symptomatic Gout and Elevated Blood Uric Acid. Selecta Biosciences. Mar. 19, 2018. 120 pages.

[No Author Listed], Crystal Arthropathies including Gout. Penn Medicine. Accessed from <https://www.pennmedicine.org/for-patients-and-visitors/find-a-program-or-service/rheumatology/crystal-arthropathies-including-gout> on Mar. 15, 2023. 3 pages.

(56) References Cited

OTHER PUBLICATIONS

[No Author Listed], Pegadricase. PubChem CID No. 86278331. Created Nov. 22, 2014. Retrieved from <https://pubchem.ncbi.nlm.nih.gov/compound/86278331> on Jan. 12, 2023. 17 pages.

Abdelwahed et al., Freeze-drying of nanoparticles: formulation, process and storage considerations. Adv Drug Deliv Rev. Dec. 30, 2006;58(15):1688-713. doi: 10.1016/j.addr.2006.09.017. Epub Oct. 6, 2006.

Calcedo et al., Adeno-associated virus antibody profiles in newborns, children, and adolescents. Clin Vaccine Immunol. Sep. 2011;18(9):1586-8. doi: 10.1128/CVI.05107-11. Epub Jul. 20, 2011.

Chapman, Practical management of organic acidemias. Translational Science of Rare Diseases. 2019;4:121-31.

Doerfler et al., Targeted approaches to induce immune tolerance for Pompe disease therapy. Mol Ther Methods Clin Dev. Jan. 27, 2016;3:15053. doi: 10.1038/mtm.2015.53.

Du et al., Regulation role of ibuprofen toward the morphology of porous silica nanospheres during its in situ encapsulation. J Colloid Interface Sci. May 15, 2010;345(2):269-77. doi: 10.1016/j.jcis.2010.02.012. Epub Feb. 11, 2010.

Fang et al., Gene therapy for hemophilia B: host immunosuppression prolongs the therapeutic effect of adenovirus-mediated factor IX expression. Hum Gene Ther. Aug. 1995;6(8):1039-44. doi: 10.1089/hum.1995.6.8-1039.

Franks et al. Non-equivalence of different evaluation algorithms to derive mean particle size from dynamic light scattering data. J Nanopart Res. Aug. 28, 2019;21:195. 10 pages. https://doi.org/10.1007/s11051-019-4630-2.

Franks, F., Freeze-drying of bioproducts: putting principles into practice. Eur J Pharm Biopharm. May 1998;45(3):221-9. doi: 10.1016/s0939-6411(98)00004-6.

Hamdy et al., Activation of antigen-specific T cell-responses by mannan-decorated PLGA nanoparticles. Pharm Res. Sep. 2011;28(9):2288-301. doi: 10.1007/s11095-011-0459-9. Epub May 11, 2011.

Ilyinskii et al., Dose finding study of AAV-LSP-MMUT in a mouse model of MMA and efficient suppression of anti-capsid antibody responses by single and multiple administrations of ImmTOR nanoparticles. Selecta Biosciences. 28th Annual Congress of the European Society of Gene & Cell Therapy (ESGCT). Oct. 19-22, 2021. Poster. 13 pages.

Ilyinskii et al., Efficient suppression of IgG antibody responses to high doses of AAV8 capsids by single and multiple administrations of ImmTOR nanoparticles. Selecta Biosciences. 28th Annual Congress of the European Society of Gene & Cell Therapy (ESGCT). Oct. 19-22, 2021. Poster. 13 pages.

Ilyinskii et al., Enhancement of liver-directed transgene expression at initial and repeat doses of AAV vectors admixed with ImmTOR nanoparticles. Sci Adv. Feb. 24, 2021;7(9):eabd0321. doi: 10.1126/sciadv.abd0321.

Ilyinskii et al., ImmTOR combined with B cell-targeted therapies provides synergistic activity in mitigating anti-AAV capsid antibody responses and enables repeated vector dosings. Selecta Biosciences. 28th Annual Congress of the European Society of Gene & Cell Therapy (ESGCT). Oct. 19-22, 2021. Poster. 14 pages.

Ilyinskii et al., ImmTOR nanoparticles enhance AAV transgene expression after initial and repeat dosing in a mouse model of methylmalonic acidemia. Mol Ther Methods Clin Dev. Jul. 16, 2021;22:279-292. doi: 10.1016/j.omtm.2021.06.015.

Ilyinskii et al., ImmTOR™ tolerogenic nanoparticles enhance transgene expression after both initial and repeat dosing in a mouse model of methylmalonic acidemia treated with Anc80 AAV-Mut vector. ESGCT 27th Annual Congress in collaboration with SETGyc Barcelona, Spain. Oct. 22-25, 2019. Human Gene Ther. Nov. 1, 2019;30(11). Abstract. 1 page.

Jhunjhunwala et al., Controlled release formulations of IL-2, TGF-β1 and rapamycin for the induction of regulatory T cells. J Control Release. Apr. 10, 2012;159(1):78-84. doi: 10.1016/j.jconrel.2012.01.013. Epub Jan. 21, 2012.

Kang et al., De novo induction of antigen-specific CD4+CD25+Foxp3+ regulatory T cells in vivo following systemic antigen administration accompanied by blockade of mTOR. J Leukoc Biol. May 2008;83(5):1230-9. doi: 10.1189/jlb.1207851. Epub Feb. 12, 2008.

Kassis, E.N., Nanoparticle use in the modulation of transplant rejection in a murine model. Yale Medicine Thesis Digital Library. Sep. 10, 2010;93. 96 pages. Accessed from <http://elischolar.library.yale.edu/ymtdl/93 >.

Khoryati et al., An IL-2 mutein engineered to promote expansion of regulatory T cells arrests ongoing autoimmunity in mice. Sci Immunol. Aug. 14, 2020;5(50):eaba5264. doi: 10.1126/sciimmunol.aba5264.

Kishimoto et al., Enhanced level and durability of AAV transgene expression and mitigation of anti-capsid neutralizing antibodies by ImmTOR tolerogenic nanoparticles in nonhuman primates. Selecta Biosciences. 28th Annual Congress of the European Society of Gene & Cell Therapy (ESGCT). Oct. 19-22, 2021. Poster. 9 pages.

Kishimoto et al., ImmTOR nanoparticles enhance the level and durability of AAV transgene expression after initial dosing and mitigate the formation of neutralizing antibodies in nonhuman primates. Selecta Biosciences. May 11, 2021. Accessed from <https://selectabio.com/wp-content/uploads/2021/10/Kishimoto-Abstract-761-ASGCT-NHP-11May2021.pdf> on Jan. 19, 2023. Poster 1 page.

Lechner et al., IgA1 Protease Treatment Reverses Mesangial Deposits and Hematuria in a Model of IgA Nephropathy. J Am Soc Nephrol. Sep. 2016;27(9):2622-9. doi: 10.1681/ASN.2015080856. Epub Feb. 5, 2016.

Li et al., The combination therapy of ImmTOR™ with AAV Anc80 is Therapeutic, Safe and Repeatable in Mice with Methylmalonic Acidemia, and Compatible with the low seroprevalence of Anc80 Nabs in the patient population. 22nd Annual Meeting of the American Society of Gene and Cell Therapy. Mol Ther. Apr. 2019;27(4):Suppl 1:202. 1 page.

Ma et al., Enhanced presentation of MHC class Ia, Ib and class II-restricted peptides encapsulated in biodegradable nanoparticles: a promising strategy for tumor immunotherapy. J Transl Med. Mar. 31, 2011;9:34. doi: 10.1186/1479-5876-9-34.

Northrup et al., Screening Immunomodulators To Skew the Antigen-Specific Autoimmune Response. Mol Pharm. Jan. 3, 2017;14(1):66-80. doi: 10.1021/acs.molpharmaceut.6b00725. Epub Dec. 7, 2016.

Pilon et al., Administration of low doses of IL-2 combined to rapamycin promotes allogeneic skin graft survival in mice. Am J Transplant. Dec. 2014;14(12):2874-82. doi: 10.1111/ajt.12944.

Ross et al., The DNA sequence of the human X chromosome. Nature. Mar. 17, 2005;434(7031):325-37. doi: 10.1038/nature03440.

Sands et al., SEL-212: Selective Mitigation of Anti-Drug Antibodies Against Pegsiticase to Control Serum Uric Acid in Hyperuricemic Subjects. Annals of Rheumatic Diseases. Jun. 15, 2018;77:658-9.

Satake et al., Inhibition of calcineurin abrogates while inhibition of mTOR promotes regulatory T cell expansion and graft-versus-host disease protection by IL-2 in allogeneic bone marrow transplantation. PLoS One. Mar. 21, 2014;9(3):e92888. doi: 10.1371/journal.pone.0092888.

Shin et al., Rapamycin and IL-2 reduce lethal acute graft-versus-host disease associated with increased expansion of donor type CD4+CD25+Foxp3+ regulatory T cells. Blood. Aug. 25, 2011;118(8):2342-50. doi: 10.1182/blood-2010-10-313684. Epub Jul. 6, 2011.

Taniguchi, Treatment of refractory gout with Pegloticase. Hyperuricemia and Gout. 2014;22(2):147-152.

Tian et al., Rapamycin slows IgA nephropathy progression in the rat. Am J Nephrol. 2014;39(3):218-29. doi: 10.1159/000358844. Epub Mar. 6, 2014.

Uermosi et al., Mechanisms of allergen-specific desensitization. J Allergy Clin Immunol. Aug. 2010;126(2):375-83. doi: 10.1016/j.jaci.2010.05.040. Epub Jul. 10, 2010.

Van, P.Y., Liver Injury. Merck Manual Consumer Version. Modified Sep. 2022. Accessed from <https://www.merckmanuals.com/home/injuries-and-poisoning/abdominal-injuries/liver-injury#:~:text=The%20liver%20can%20be%20damaged,go%20deep%20into%20the%20liver> on Dec. 14, 2022. 2 pages.

(56) References Cited

OTHER PUBLICATIONS

Wang et al., The potential of adeno-associated viral vectors for gene delivery to muscle tissue. Expert Opin Drug Deliv. Mar. 2014;11(3):345-364. doi: 10.1517/17425247.2014.871258. Epub Jan. 3, 2014.
Xinqiang et al., Therapeutic efficacy of experimental rheumatoid arthritis with low-dose methotrexate by increasing partially CD4+ CD25+ Treg cells and inducing Th1 to Th2 shift in both cells and cytokines. Biomed Pharmacother. Sep. 2010;64(7):463-71. doi: 10.1016/j.biopha.2010.01.007. Epub Feb. 25, 2010.
Zhou et al., Challenges and strategies: the immune responses in gene therapy. Med Res Rev. Nov. 2004;24(6):748-61. doi: 10.1002/med.20009.
U.S. Appl. No. 12/764,569, filed Apr. 21, 2010, Lipford et al.
U.S. Appl. No. 12/788,261, filed May 26, 2010, Lipford et al.
U.S. Appl. No. 12/862,076, filed Aug. 24, 2010, Fraser et al.
U.S. Appl. No. 13/116,453, filed May 26, 2011, Bratzler et al.
U.S. Appl. No. 13/116,488, filed May 26, 2011, Bratzler et al.
U.S. Appl. No. 13/116,556, filed May 26, 2011, Bratzler et al.
U.S. Appl. No. 13/428,340, filed Mar. 23, 2012, Altreuter et al.
U.S. Appl. No. 13/457,994, filed Apr. 27, 2012, Fraser et al.
U.S. Appl. No. 13/560,955, filed Jul. 27, 2012, Altreuter et al.
U.S. Appl. No. 13/948,129, filed Jul. 22, 2013, Zepp et al.
U.S. Appl. No. 14/269,048, filed May 2, 2014, Maldonado.
U.S. Appl. No. 14/269,056, filed May 2, 2014, Maldonado et al.
U.S. Appl. No. 14/269,042, filed May 2, 2014, Kishimoto et al.
U.S. Appl. No. 14/296,204, filed Jun. 4, 2014, Maldonado et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/810,418, filed Jul. 27, 2015, Fraser et al.
U.S. Appl. No. 14/810,427, filed Jul. 27, 2015, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 14/810,476, filed Jul. 27, 2015, Maldonado.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 15/050,397, filed Feb. 22, 2016, Fraser et al.
U.S. Appl. No. 15/061,096, filed Mar. 4, 2016, Fraser et al.
U.S. Appl. No. 15/456,520, filed Mar. 11, 2017, Johnston.
U.S. Appl. No. 15/629,973, filed Jun. 22, 2017, Lipford et al.
U.S. Appl. No. 15/684,896, filed Aug. 23, 2017, Ilyinskii et al.
U.S. Appl. No. 15/685,648, filed Aug. 24, 2017, O'Neil.
U.S. Appl. No. 15/717,710, filed Sep. 27, 2017, Kishimoto.
U.S. Appl. No. 15/863,076, filed Jan. 5, 2018, Ilyinskii et al.
U.S. Appl. No. 15/889,014, filed Feb. 5, 2018, Zepp et al.
U.S. Appl. No. 15/917,742, filed Mar. 11, 2018, Johnston.
U.S. Appl. No. 16/056,204, filed Aug. 6, 2018, Altreuter et al.
U.S. Appl. No. 16/100,040, filed Aug. 9, 2018, Kishimoto.
U.S. Appl. No. 16/159,166, filed Oct. 12, 2018, Ilyinskii et al.
U.S. Appl. No. 16/410,876, filed May 13, 2019, Kishimoto.
U.S. Appl. No. 16/433,622, filed Jun. 6, 2019, Maldonado et al.
U.S. Appl. No. 16/438,147, filed Jun. 11, 2019, Maldonado.
U.S. Appl. No. 16/513,566, filed Jul. 16, 2019, Keller.
U.S. Appl. No. 16/513,576, filed Jul. 16, 2019, Keller.
U.S. Appl. No. 16/536,154, filed Aug. 8, 2019, Fraser et al.
U.S. Appl. No. 16/550,725, filed Aug. 26, 2019, Maldonado et al.
U.S. Appl. No. 16/560,419, filed Sep. 4, 2019, Kishimoto et al.
U.S. Appl. No. 16/739,450, filed Jan. 10, 2020, Zepp et al.
U.S. Appl. No. 16/773,551, filed Jan. 27, 2020, Lipford et al.
U.S. Appl. No. 16/858,349, filed Apr. 24, 2020, Maldonado.
U.S. Appl. No. 16/860,729, filed Apr. 28, 2020, Kishimoto et al.
U.S. Appl. No. 16/885,758, filed May 28, 2020, Kishimoto et al.
U.S. Appl. No. 16/893,153, filed Jun. 4, 2020, Johnston et al.
U.S. Appl. No. 17/076,080, filed Oct. 21, 2020, Ilyinskii et al.
U.S. Appl. No. 17/092,148, filed Nov. 6, 2020, Johnston et al.
U.S. Appl. No. 17/154,414, filed Jan. 21, 2021, Altreuter et al.
U.S. Appl. No. 17/187,512, filed Feb. 26, 2021, Ilyinskii et al.
U.S. Appl. No. 17/199,130, filed Mar. 11, 2021, Johnston.
U.S. Appl. No. 17/211,459, filed Mar. 24, 2021, Kishimoto.
U.S. Appl. No. 17/519,413, filed Nov. 4, 2021, Kishimoto.

\* cited by examiner

SEQUENCE LISTING

```
<160> NUMBER OF SEQ ID NOS: 516

<210> SEQ ID NO 1
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 1

Ala His Ala Ser Ala Arg Gln Gln Trp Glu Leu Gln Gly Asp Arg Arg
1               5                   10                  15

Cys Gln Ser Gln
            20

<210> SEQ ID NO 2
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 2

Ala Lys Leu Thr Ile Leu Val Ala Leu Ala Leu Phe Leu Leu Ala Ala
1               5                   10                  15

His Ala Ser Ala
            20

<210> SEQ ID NO 3
<211> LENGTH: 19
<212> TYPE: PRT
<213> ORGANISM: Artificial Sequence
<220> FEATURE:
<223> OTHER INFORMATION: Arachis hypogaea 2S protein 1 epitope
```

-continued

```
<400> SEQUENCE: 3

Ala Leu Gln Gln Ile Met Glu Asn Gln Ser Asp Arg Leu Gln Gly Arg
1               5                   10                  15

Gln Gln Glu

<210> SEQ ID NO 4
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 4

Ala Asn Leu Arg Pro Cys Glu Gln His Leu Met Gln Lys Ile Gln Arg
1               5                   10                  15

Asp Glu Asp Ser
            20

<210> SEQ ID NO 5
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 5

Cys Asn Glu Leu Asn Glu Phe Glu Asn Asn Gln Arg Cys Met Cys Glu
1               5                   10                  15

Ala Leu Gln Gln
            20

<210> SEQ ID NO 6
<211> LENGTH: 16
<212> TYPE: PRT
<213> ORGANISM: Artificial Sequence
<220> FEATURE:
<223> OTHER INFORMATION: Homo sapiens 5-hydroxytryptamine receptor 2C
      (5-HT-2C) (Serotonin receptor 2C) (5-HT2C) (5-HTR2C) (5HT-1C)
      epitope

<400> SEQUENCE: 6

Pro Arg Gly Thr Met Gln Ala Ile Asn Asn Glu Arg Lys Ala Ser Lys
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 7

Asp Gln Gly Thr Cys Leu Leu Leu Thr Glu Val Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 8

Glu Leu Glu Lys Tyr Gln Gln Leu Asn Ser Glu Arg Gly Val
1               5                   10
```

-continued

```
<210> SEQ ID NO 9
<211> LENGTH: 13
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 9

Gly Glu Arg Ile Thr Lys Met Thr Glu Gly Leu Ala Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 10

Pro Gly Glu Trp Arg Ile Ile Tyr Ala Ala Ala Asp Asn Lys
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 11

Arg Ile Glu Cys Ile Asn Asp Cys
1               5

<210> SEQ ID NO 12
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 12

Val Ala Lys Arg Gln Glu Gly Tyr Val Tyr Val Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 13

Val Ser Glu Asn Met Leu Val Thr Tyr Val
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 14

Glu Leu Glu Lys Tyr Gln Gln Leu Asn Ser Glu Arg Gly Val Pro Asn
1               5                   10                  15
```

```
<210> SEQ ID NO 15
<211> LENGTH: 13
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 15

Asp Ile Phe Ala Ser Lys Asn Phe His Leu Gln Lys Asn
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 16

Gly Ile Ile Ala Ala Tyr Gln Asn Pro Ala Ser Trp Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 17

Lys Leu Thr Ser Gly Lys Ile Ala Ser Cys Leu Asn
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 18

Gln Phe Ala Lys Leu Thr Gly Phe Thr Leu Met Gly
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 19

Ile Asn Gln Gln Leu Asn Pro Lys
1               5

<210> SEQ ID NO 20
<211> LENGTH: 15
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 20

Ile Asn Gln Gln Leu Asn Pro Lys Thr Asn Lys Trp Glu Asp Lys
1               5                   10                  15
```

```
<210> SEQ ID NO 21
<211> LENGTH: 11
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 21

Leu Asn Pro Lys Thr Asn Lys Trp Glu Asp Lys
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 22

Thr Asn Lys Trp Glu Asp Lys
1               5

<210> SEQ ID NO 23
<211> LENGTH: 12
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 23

Leu Asn Pro Lys Thr Asn Lys Trp Glu Asp Lys Arg
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 24

Pro Arg Leu Ser Trp His Gln Tyr Thr Lys Arg Asp Ser Arg Glu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 25

Thr Val Asp Leu Ile Ser Pro Val Thr Lys Arg Ala Ser Leu Lys
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 26

Ala Trp Tyr Tyr Val Pro Leu Gly Thr Gln Tyr Thr Asp Ala Pro Ser
1               5                   10                  15
```

Phe Ser

<210> SEQ ID NO 27
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 27

Asp Ala Tyr Pro Ser Gly Ala Trp Tyr Tyr Val Pro Leu Gly Thr Gln
1               5                   10                  15

Tyr Thr

<210> SEQ ID NO 28
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 28

Asp Ile Gly Ser Glu Ser Thr Glu Asp Gln Ala Met Glu Asp Ile Lys
1               5                   10                  15

Gln Met

<210> SEQ ID NO 29
<211> LENGTH: 6
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 29

Glu Asp Ile Lys Gln Met
1               5

<210> SEQ ID NO 30
<211> LENGTH: 12
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 30

Glu Pro Met Ile Gly Val Asn Gln Glu Leu Ala Tyr
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 31

Glu Pro Met Ile Gly Val Asn Gln Glu Leu Ala Tyr Phe Tyr Pro Glu
1               5                   10                  15

Leu Phe

<210> SEQ ID NO 32
<211> LENGTH: 17
<212> TYPE: PRT
<213> ORGANISM: Artificial Sequence

```
<220> FEATURE:
<223> OTHER INFORMATION: Arachis hypogaea Ara h 2.01 allergen epitope

<400> SEQUENCE: 32

Glu Leu Asn Glu Phe Glu Asn Asn Gln Arg Cys Met Cys Glu Ala Leu
1               5                   10                  15

Gln

<210> SEQ ID NO 33
<211> LENGTH: 16
<212> TYPE: PRT
<213> ORGANISM: Artificial Sequence
<220> FEATURE:
<223> OTHER INFORMATION: Arachis hypogaea Ara h 2.01 allergen epitope

<400> SEQUENCE: 33

Ser Gln Leu Glu Arg Ala Asn Leu Arg Pro Cys Glu Gln His Leu Met
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 34

Gly Ala Thr Arg Asp Arg Pro Leu Trp Ile Ile Phe Ser Gly Asn
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 35

Ile Phe Ser Gly Asn Met Asn Ile Lys Leu Lys Met Pro Met Tyr Ile
1               5                   10                  15

Ala Gly Tyr Lys
            20

<210> SEQ ID NO 36
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 36

Lys Met Pro Met Tyr Ile Ala Gly Tyr Lys Thr Phe Asp Gly Arg Gly
1               5                   10                  15

Ala Gln Val Tyr
            20

<210> SEQ ID NO 37
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 37

Leu Gly His Asp Asp Ala Tyr Ser Asp Asp Lys Ser Met Lys Val Thr
```

```
<210> SEQ ID NO 38
<211> LENGTH: 19
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 38

Ser Gly Lys Tyr Glu Gly Gly Asn Ile Tyr Thr Lys Lys Glu Ala Phe
1               5                   10                  15
Asn Val Glu

<210> SEQ ID NO 39
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 39

Glu Asn Pro Lys Lys Tyr Ile Pro Gly Thr Lys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 40

Gly Leu Phe Gly Arg Lys Thr Gly Ser Val Ala
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 41

Lys Ile Gly Pro Glu Leu His Gly Leu
1               5

<210> SEQ ID NO 42
<211> LENGTH: 12
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 42

Leu Lys Ala Gly Glu Gly Asn Lys Ile Gly Pro Glu
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Cochliobolus lunatus Cytochrome c epitope
```

(Val Ala Phe Asn continued from previous: Val Ala Phe Asn at position 20)

<400> SEQUENCE: 43

Leu Lys Lys Pro Lys Asp Arg Asn Asp Leu Ile
1               5                   10

<210> SEQ ID NO 44
<211> LENGTH: 18
<212> TYPE: PRT
<213> ORGANISM: Artificial Sequence
<220> FEATURE:
<223> OTHER INFORMATION: Dermatophagoides farinae Der f 2 allergen
      epitope

<400> SEQUENCE: 44

Gly Leu Glu Ile Asp Val Pro Gly Ile Asp Thr Asn Ala Cys His Phe
1               5                   10                  15

Val Lys

<210> SEQ ID NO 45
<211> LENGTH: 20
<212> TYPE: PRT
<213> ORGANISM: Artificial Sequence
<220> FEATURE:
<223> OTHER INFORMATION: Dermatophagoides farinae Der f 2 allergen
      epitope

<400> SEQUENCE: 45

Pro Gly Ile Asp Thr Asn Ala Cys His Phe Val Lys Cys Pro Leu Val
1               5                   10                  15

Lys Gly Gln Gln
            20

<210> SEQ ID NO 46
<211> LENGTH: 19
<212> TYPE: PRT
<213> ORGANISM: Artificial Sequence
<220> FEATURE:
<223> OTHER INFORMATION: Dermatophagoides pteronyssinus Der p 1
      allergen epitope

<400> SEQUENCE: 46

Arg Phe Gly Ile Ser Asn Tyr Cys Gln Ile Tyr Pro Pro Asn Ala Asn
1               5                   10                  15

Lys Ile Arg

<210> SEQ ID NO 47
<211> LENGTH: 15
<212> TYPE: PRT
<213> ORGANISM: Artificial Sequence
<220> FEATURE:
<223> OTHER INFORMATION: Dermatophagoides pteronyssinus Der p 1
      allergen epitope

<400> SEQUENCE: 47

Ala Val Asn Ile Val Gly Tyr Ser Asn Ala Gln Gly Val Asp Tyr
1               5                   10                  15

<210> SEQ ID NO 48
<211> LENGTH: 20
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 48

Phe Ala Gly Lys Asp Leu Glu Ser Ile Lys Gly Thr Ala Pro Phe Glu
1               5                   10                  15

Thr His Ala Asn
            20

<210> SEQ ID NO 49
<211> LENGTH: 11
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 49

Gly Thr Ala Pro Phe Glu Thr His Ala Asn Arg
1               5                   10

<210> SEQ ID NO 50
<211> LENGTH: 21
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 50

Lys Gly Thr Ala Pro Phe Glu Thr His Ala Asn Arg Ile Val Gly Phe
1               5                   10                  15

Phe Ser Lys Ile Ile
            20

<210> SEQ ID NO 51
<211> LENGTH: 21
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 51

Ala His Thr Asp Phe Ala Gly Ala Glu Ala Ala Trp Gly Ala Thr Leu
1               5                   10                  15

Asp Thr Phe Phe Gly
            20

<210> SEQ ID NO 52
<211> LENGTH: 20
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 52

Phe Ala Gly Lys Asp Leu Glu Ser Ile Lys Gly Thr Ala Pro Phe Glu
1               5                   10                  15

Ile His Ala Asn
            20

<210> SEQ ID NO 53
<211> LENGTH: 21
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 53

Val Asn Thr Phe Val Ala Ser His Lys Pro Arg Gly Val Thr His Asp
1               5                   10                  15

Gln Leu Asn Asn Phe
            20

<210> SEQ ID NO 54
<211> LENGTH: 8
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 54

Ala Asp Pro Ser Ile Met Ala Lys
1               5

<210> SEQ ID NO 55
<211> LENGTH: 21
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 55

Ala Asp Pro Ser Ile Met Ala Lys Phe Thr Gln Phe Ala Gly Lys Asp
1               5                   10                  15

Leu Glu Ser Ile Lys
            20

<210> SEQ ID NO 56
<211> LENGTH: 5
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 56

Ala Glu Ala Ala Trp
1               5

<210> SEQ ID NO 57
<211> LENGTH: 20
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 57

Ala Glu Ala Ala Trp Gly Ala Thr Leu Asp Thr Phe Phe Gly Met Ile
1               5                   10                  15

Phe Ser Lys Met
            20

<210> SEQ ID NO 58
<211> LENGTH: 8
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 58

Ala Gly Phe Val Ser Tyr Met Lys
1               5

<210> SEQ ID NO 59
<211> LENGTH: 15
<212> TYPE: PRT
<213> ORGANISM: Artificial Sequence
<220> FEATURE:
<223> OTHER INFORMATION: Phaseolus vulgaris Glycine-rich cell wall
      structural protein 1.8 precursor epitope

<400> SEQUENCE: 59

Gly Gly Tyr Gly Asp Gly Gly Ala His Gly Gly Gly Tyr Gly Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 60

Ala Thr Pro Glu Ala Lys Tyr Asp Ala Tyr Val Ala Thr Leu Ser
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 61

Phe Thr Val Phe Glu Ala Ala Phe Asn Asn Ala Ile Lys Ala Gly
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 62

Lys Tyr Asp Ala Tyr Val Ala Thr Leu Ser Glu Ala Leu Arg Ile
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 63

Pro Ala Asn Asp Lys Phe Thr Val Phe Glu Ala Ala Phe Asn Asn
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 64

Pro Lys Gly Gly Ala Glu Ser Ser Ser Lys Ala Ala Leu Thr Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Homo sapiens KIAA1224 protein epitope

<400> SEQUENCE: 65

Asp Leu Glu Ser Tyr Leu Gln Leu Asn Cys Glu Arg Gly Thr Trp Arg
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Lepidoglyphus destructor Lep D 2 precursor
      epitope

<400> SEQUENCE: 66

Lys Gly Glu Ala Leu Asp Phe Asn Tyr Gly Met Thr Ile Pro Ala
1               5                   10                  15

<210> SEQ ID NO 67
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 67

Ala Gly Leu Pro Gly Lys Cys Gly Val Asn Ile Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 68

Ala Lys Gly Ile Ala Gly Leu Asn Pro Asn Leu Ala
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 69

Cys Gly Val Asn Ile Pro Tyr Lys Ile Ser Pro Ser
1               5                   10

<210> SEQ ID NO 70
<211> LENGTH: 12
<212> TYPE: PRT

```
<213> ORGANISM: Artificial Sequence
<220> FEATURE:
<223> OTHER INFORMATION: Corylus avellana lipid transfer protein
      precursor epitope

<400> SEQUENCE: 70

Cys Lys Gly Val Arg Ala Val Asn Asp Ala Ser Arg
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 71

Cys Val Leu Tyr Leu Lys Asn Gly Gly Val Leu Pro
1               5                   10

<210> SEQ ID NO 72
<211> LENGTH: 16
<212> TYPE: PRT
<213> ORGANISM: Artificial Sequence
<220> FEATURE:
<223> OTHER INFORMATION: Homo sapiens Lipocalin 1 (tear prealbumin)
      epitope

<400> SEQUENCE: 72

Lys Pro Val Arg Gly Val Lys Leu Val Gly Arg Asp Pro Lys Asn Asn
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 73

Glu Phe Asn Thr Glu Phe Thr Ile His Ala Asp Lys Asn Asn Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 74

Phe Thr Ile His Ala Asp Lys Asn Asn Leu Lys Met His Met Asp
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 75

Lys Met His Met Asp Phe Pro Asn Val Phe Gln Ala Asp Leu Thr
1               5                   10                  15

<210> SEQ ID NO 76
```

-continued

```
<211> LENGTH: 13
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 76

Ala Leu Phe Lys Ala Leu Glu Ala Tyr Leu Ile Ala Asn
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 77

Asp Ala Val Val Pro Glu Glu Asn Ile Lys Tyr Ala
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 78

Asp Ile Leu Leu Gly Phe Ile Glu Ser Ile Glu Asn
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 79

Gly Gly Ser Ile Cys Lys Thr Thr Ala Ile Phe His
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 80

Gly Val Gln Thr His Val Leu Glu Leu Thr Ser Ser
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Aspergillus fumigatus Major allergen Asp f 2
      precursor epitope

<400> SEQUENCE: 81

Phe Gly Asn Arg Pro Thr Met Glu Ala Val Gly Ala Tyr Asp Val
1               5                   10                  15

<210> SEQ ID NO 82
```

```
<211> LENGTH: 15
<212> TYPE: PRT
<213> ORGANISM: Artificial Sequence
<220> FEATURE:
<223> OTHER INFORMATION: Aspergillus fumigatus Major allergen Asp f 2
      precursor epitope

<400> SEQUENCE: 82

Met Glu Ala Val Gly Ala Tyr Asp Val Ile Val Asn Gly Asp Lys
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Canis lupus familiaris Major allergen Can f 1
      precursor epitope

<400> SEQUENCE: 83

Ala Leu Glu Asp Phe Arg Glu Phe Ser Arg Ala Lys Gly Leu Asn Gln
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Canis lupus familiaris Major allergen Can f 1
      precursor epitope

<400> SEQUENCE: 84

Asp Gln Glu Val Pro Glu Lys Pro Asp Ser Val Thr Pro Met Ile Leu
1               5                   10                  15

<210> SEQ ID NO 85
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 85

Ala Gly Lys Glu Lys Ala Ala Gly Leu Phe Lys Ala
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 86

Ala Gly Leu Phe Lys Ala Val Glu Ala Tyr Leu Leu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 87
```

```
Ala Pro Gln His Phe Thr Ser Ala Glu Asn Leu Glu
1               5                   10
```

<210> SEQ ID NO 88
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 88

```
Ala Arg Leu Phe Lys Ser Phe Val Leu Asp Ala Asp
1               5                   10
```

<210> SEQ ID NO 89
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 89

```
Glu Ile Asp His Ala Asn Phe Lys Tyr Cys Tyr Ser
1               5                   10
```

<210> SEQ ID NO 90
<211> LENGTH: 13
<212> TYPE: PRT
<213> ORGANISM: Artificial Sequence
<220> FEATURE:
<223> OTHER INFORMATION: Daucus carota Major allergen Dau c 1 epitope

<400> SEQUENCE: 90

```
Ala Leu Phe Lys Ala Ile Glu Ala Tyr Leu Ile Ala Asn
1               5                   10
```

<210> SEQ ID NO 91
<211> LENGTH: 16
<212> TYPE: PRT
<213> ORGANISM: Artificial Sequence
<220> FEATURE:
<223> OTHER INFORMATION: Equus caballus Major allergen Equ c 1
      precursor epitope

<400> SEQUENCE: 91

```
Asp Gly Tyr Asn Val Phe Arg Ile Ser Glu Phe Glu Asn Asp Glu His
1               5                   10                  15
```

<210> SEQ ID NO 92
<211> LENGTH: 16
<212> TYPE: PRT
<213> ORGANISM: Artificial Sequence
<220> FEATURE:
<223> OTHER INFORMATION: Equus caballus Major allergen Equ c 1
      precursor epitope

<400> SEQUENCE: 92

```
Asp Lys Asp Arg Pro Phe Gln Leu Phe Glu Phe Tyr Ala Arg Glu Pro
1               5                   10                  15
```

<210> SEQ ID NO 93
<211> LENGTH: 16
<212> TYPE: PRT
<213> ORGANISM: Artificial Sequence
<220> FEATURE:
<223> OTHER INFORMATION: Equus caballus Major allergen Equ c 1

```
    precursor epitope

<400> SEQUENCE: 93

Asp Leu Thr Lys Ile Asp Arg Cys Phe Gln Leu Arg Gly Asn Gly Val
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Equus caballus Major allergen Equ c 1
      precursor epitope

<400> SEQUENCE: 94

Asp Arg Pro Phe Gln Leu Phe Glu Phe Tyr Ala Arg Glu Pro Asp Val
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Equus caballus Major allergen Equ c 1
      precursor epitope

<400> SEQUENCE: 95

Asp Val Ser Pro Glu Ile Lys Glu Glu Phe Val Lys Ile Val Gln Lys
1               5                   10                  15

<210> SEQ ID NO 96
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 96

Glu Asn Ala Arg Ile Leu Lys Asn Cys Val Asp Ala Lys Met Thr Glu
1               5                   10                  15

Glu

<210> SEQ ID NO 97
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 97

Arg Asp Val Asp Leu Phe Leu Thr Gly Thr Pro Asp Glu Tyr Val Glu
1               5                   10                  15

Gln

<210> SEQ ID NO 98
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 98

Thr Gly Thr Pro Asp Glu Tyr Val Glu Gln Val Ala Gln Tyr Lys Ala
1               5                   10                  15

Leu
```

```
<210> SEQ ID NO 99
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 99

Asp Val Asp Leu Phe Leu Thr Gly Thr Pro Asp Glu Tyr Val Glu Gln
1               5                   10                  15
Val

<210> SEQ ID NO 100
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 100

Glu Ile Cys Pro Ala Val Lys Arg Asp Val Asp Leu Phe Leu Thr Gly
1               5                   10                  15
Thr

<210> SEQ ID NO 101
<211> LENGTH: 16
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 101

Glu Gln Val Ala Gln Tyr Lys Ala Leu Pro Val Val Leu Glu Asn Ala
1               5                   10                  15

<210> SEQ ID NO 102
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 102

Lys Ala Leu Pro Val Val Leu Glu Asn Ala Arg Ile Leu Lys Asn Cys
1               5                   10                  15
Val

<210> SEQ ID NO 103
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 103

Leu Phe Leu Thr Gly Thr Pro Asp Glu Tyr Val Glu Gln Val Ala Gln
1               5                   10                  15
Tyr
```

<210> SEQ ID NO 104
<211> LENGTH: 16
<212> TYPE: PRT
<213> ORGANISM: Artificial Sequence
<220> FEATURE:
<223> OTHER INFORMATION: Felis catus major allergen I, polypeptide
      chain 1 epitope

<400> SEQUENCE: 104

Lys Glu Asn Ala Leu Ser Leu Leu Asp Lys Ile Tyr Thr Ser Pro Leu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Felis catus major allergen I, polypeptide
      chain 1 epitope

<400> SEQUENCE: 105

Lys Met Thr Glu Glu Asp Lys Glu Asn Ala Leu Ser Leu Leu Asp Lys
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Malus x domestica Major allergen Mal d 1
      epitope

<400> SEQUENCE: 106

Gly Leu Phe Lys Leu Ile Glu Ser Tyr Leu Lys Asp His Pro Asp
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Prunus avium Major allergen Pru av 1 epitope

<400> SEQUENCE: 107

Asn Leu Phe Lys Leu Ile Glu Thr Tyr Leu Lys Gly His Pro Asp
1               5                   10                  15

<210> SEQ ID NO 108
<211> LENGTH: 20
<212> TYPE: PRT
<213> ORGANISM: Artificial Sequence
<220> FEATURE:
<223> OTHER INFORMATION: Hevea brasiliensis Major latex allergen Hev b
      5 epitope

<400> SEQUENCE: 108

Ala Ala Pro Ala Glu Gly Glu Lys Pro Ala Glu Glu Lys Pro Ile
1               5                   10                  15

Thr Glu Ala Ala
            20

<210> SEQ ID NO 109
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5 epitope

<400> SEQUENCE: 109

Ala Glu Glu Glu Lys Pro Ile Thr Glu Ala Ala Glu Thr Ala Thr Thr
1               5                   10                  15

Glu Val Pro Val
            20

<210> SEQ ID NO 110
<211> LENGTH: 20
<212> TYPE: PRT
<213> ORGANISM: Artificial Sequence
<220> FEATURE:
<223> OTHER INFORMATION: Hevea brasiliensis Major latex allergen Hev b
      5 epitope

<400> SEQUENCE: 110

Ala Pro Ala Glu Pro Glu Ala Pro Ala Pro Glu Thr Glu Lys Ala Glu
1               5                   10                  15

Glu Val Glu Lys
            20

<210> SEQ ID NO 111
<211> LENGTH: 20
<212> TYPE: PRT
<213> ORGANISM: Artificial Sequence
<220> FEATURE:
<223> OTHER INFORMATION: Hevea brasiliensis Major latex allergen Hev b
      5 epitope

<400> SEQUENCE: 111

Ala Pro Glu Ala Asp Gln Thr Thr Pro Glu Glu Lys Pro Ala Glu Pro
1               5                   10                  15

Glu Pro Val Ala
            20

<210> SEQ ID NO 112
<211> LENGTH: 20
<212> TYPE: PRT
<213> ORGANISM: Artificial Sequence
<220> FEATURE:
<223> OTHER INFORMATION: Hevea brasiliensis Major latex allergen Hev b
      5 epitope

<400> SEQUENCE: 112

Ala Ser Glu Gln Glu Thr Ala Asp Ala Thr Pro Glu Lys Glu Glu Pro
1               5                   10                  15

Thr Ala Ala Pro
            20

<210> SEQ ID NO 113
<211> LENGTH: 11
<212> TYPE: PRT
<213> ORGANISM: Artificial Sequence
<220> FEATURE:
<223> OTHER INFORMATION: Dermatophagoides pteronyssinus Major mite
      fecal allergen Der p 1 epitope

<400> SEQUENCE: 113

Tyr Ala Tyr Val Ala Arg Glu Gln Ser Cys Arg
1               5                   10

<210> SEQ ID NO 114
<211> LENGTH: 19
<212> TYPE: PRT

```
<213> ORGANISM: Artificial Sequence
<220> FEATURE:
<223> OTHER INFORMATION: Dermatophagoides pteronyssinus Major mite
      fecal allergen Der p 1 epitope

<400> SEQUENCE: 114

Ala Leu Ala Gln Thr His Thr Ala Ile Ala Val Ile Ile Gly Ile Lys
1               5                   10                  15

Asp Leu Asp

<210> SEQ ID NO 115
<211> LENGTH: 35
<212> TYPE: PRT
<213> ORGANISM: Artificial Sequence
<220> FEATURE:
<223> OTHER INFORMATION: Olea europaea Major pollen allergen epitope

<400> SEQUENCE: 115

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro
        35

<210> SEQ ID NO 116
<211> LENGTH: 31
<212> TYPE: PRT
<213> ORGANISM: Artificial Sequence
<220> FEATURE:
<223> OTHER INFORMATION: Olea europaea Major pollen allergen epitope

<400> SEQUENCE: 116

Gly Ala Ser Leu Arg Leu Gln Cys Lys Asp Lys Glu Asn Gly Asp Val
1               5                   10                  15

Thr Phe Thr Glu Val Gly Tyr Thr Arg Ala Glu Gly Leu Tyr Ser
            20                  25                  30

<210> SEQ ID NO 117
<211> LENGTH: 34
<212> TYPE: PRT
<213> ORGANISM: Artificial Sequence
<220> FEATURE:
<223> OTHER INFORMATION: Olea europaea Major pollen allergen epitope

<400> SEQUENCE: 117

Gly Thr Thr Arg Thr Val Asn Pro Leu Gly Phe Phe Lys Lys Glu Ala
1               5                   10                  15

Leu Pro Lys Cys Ala Gln Val Tyr Asn Lys Leu Gly Met Tyr Pro Pro
            20                  25                  30

Asn Met

<210> SEQ ID NO 118
<211> LENGTH: 53
<212> TYPE: PRT
<213> ORGANISM: Artificial Sequence
<220> FEATURE:
<223> OTHER INFORMATION: Olea europaea Major pollen allergen epitope

<400> SEQUENCE: 118

Leu Val Glu Arg Asp His Lys Asn Glu Phe Cys Glu Ile Thr Leu Ile
1               5                   10                  15

Ser Ser Gly Arg Lys Asp Cys Asn Glu Ile Pro Thr Glu Gly Trp Ala
```

```
                    20                  25                  30
Lys Pro Ser Leu Lys Phe Lys Leu Asn Thr Val Asn Gly Thr Thr Arg
        35                  40                  45

Thr Val Asn Pro Leu
    50

<210> SEQ ID NO 119
<211> LENGTH: 33
<212> TYPE: PRT
<213> ORGANISM: Artificial Sequence
<220> FEATURE:
<223> OTHER INFORMATION: Olea europaea Major pollen allergen epitope

<400> SEQUENCE: 119

Met Leu Val Glu Arg Asp His Lys Asn Glu Phe Cys Glu Ile Thr Leu
1               5                   10                  15

Ile Ser Ser Gly Arg Lys Asp Cys Asn Glu Ile Pro Thr Glu Gly Trp
            20                  25                  30

Ala

<210> SEQ ID NO 120
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 120

Ala Gly Gly Ser Pro Ser Pro Pro Ala Asp Gly Gly
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 121

Ala Gly Ser Lys Leu Cys Glu Lys Thr Ser Lys Thr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 122

Cys Asp Lys Lys Cys Ile Glu Trp Glu Lys Ala Gln
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 123
```

Asp Gly Gly Ser Pro Pro Pro Ala Asp Gly Gly
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 124

Glu Lys Thr Ser Lys Thr Tyr Ser Gly Lys Cys Asp
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 125

Ala Ala Arg Leu Phe Lys Ala Phe Ile Leu Asp Gly
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 126

Ala Ala Arg Leu Phe Lys Ala Phe Ile Leu Asp Gly Asp Asn Leu
1               5                   10                  15

<210> SEQ ID NO 127
<211> LENGTH: 12
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 127

Ala Glu Gln Val Lys Ala Ser Lys Glu Met Gly Glu
1               5                   10

<210> SEQ ID NO 128
<211> LENGTH: 21
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 128

Ala Phe Ile Leu Asp Gly Asp Asn Leu Phe Pro Lys Val Ala Pro Gln
1               5                   10                  15

Ala Ile Ser Ser Val
            20

<210> SEQ ID NO 129
<211> LENGTH: 12

```
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 129

Ala Ile Ser Ser Val Glu Asn Ile Glu Gly Asn Gly
1               5                   10

<210> SEQ ID NO 130
<211> LENGTH: 15
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 130

Glu Thr Leu Leu Arg Ala Val Glu Ser Tyr Leu Leu Ala His Ser
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Betula pendula Major pollen allergen Bet v
      1-F/I epitope

<400> SEQUENCE: 131

Gly Glu Thr Leu Leu Arg Ala Val Glu Ser Tyr Leu Leu Ala His Ser
1               5                   10                  15

<210> SEQ ID NO 132
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 132

Ala Asn Asn Asn Tyr Asp Pro Trp Ser Ile Tyr Ala Ile Gly Gly Ser
1               5                   10                  15

Ser Asn Pro Thr
            20

<210> SEQ ID NO 133
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 133

Ala Ser Thr Gly Val Thr Ile Ser Asn Asn His Phe Phe Asn His His
1               5                   10                  15

Lys Val Met Leu
            20

<210> SEQ ID NO 134
<211> LENGTH: 20
<212> TYPE: PRT
<213> ORGANISM: Artificial Sequence
<220> FEATURE:
```

-continued

<223> OTHER INFORMATION: Chamaecyparis obtusa Major pollen allergen Cha
      o 1 precursor epitope

<400> SEQUENCE: 134

Cys Ala Asn Trp Val Trp Arg Ser Thr Gln Asp Ser Phe Asn Asn Gly
1               5                   10                  15

Ala Tyr Phe Val
            20

<210> SEQ ID NO 135
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 135

Asp Ala Ile Thr Met Arg Asn Val Thr Asp Val Trp Ile Asp His Asn
1               5                   10                  15

Ser Leu Ser Asp
            20

<210> SEQ ID NO 136
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 136

Asp Ala Asn Trp Asp Gln Asn Arg Met Lys Leu Ala Asp Cys Ala Val
1               5                   10                  15

Gly Phe Gly Ser
            20

<210> SEQ ID NO 137
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 137

Ala Ile Gly Asp Lys Pro Gly Pro Asn Ile Thr Ala Thr Tyr Gly Asn
1               5                   10                  15

Lys Trp Leu Glu
            20

<210> SEQ ID NO 138
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 138

Cys Tyr Glu Ile Lys Cys Lys Glu Pro Val Glu Cys Ser Gly Glu Pro
1               5                   10                  15

Val Leu Val Lys
            20

<210> SEQ ID NO 139
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 139

Asp His Gly Gly Ala Cys Gly Tyr Lys Asp Val Asp Lys Pro Pro Phe
1               5                   10                  15

Asp Gly Met Thr
            20

<210> SEQ ID NO 140
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 140

Glu Gly Gly Ala His Leu Val Gln Asp Asp Val Ile Pro Ala Asn Trp
1               5                   10                  15

Lys Pro Asp Thr
            20

<210> SEQ ID NO 141
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 141

Phe Lys Asp Gly Leu Gly Cys Gly Ala Cys Tyr Glu Ile Lys Cys Lys
1               5                   10                  15

Glu Pro Val Glu
            20

<210> SEQ ID NO 142
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 142

Phe Ala Glu Tyr Lys Ser Asp Tyr Val Tyr Gln Pro Phe Pro Lys
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 143

Met Leu Leu Arg Lys Tyr Gly Ile Ala Ala Glu Asn Val Ile Asp
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 144

Asn Ser Phe Lys Pro Phe Ala Glu Tyr Lys Ser Asp Tyr Val Tyr
1               5                   10                  15

<210> SEQ ID NO 145
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 145

Ala Ser Asn Lys Arg Glu Lys Ile Glu Glu Asn Gly Ser Met Arg Val
1               5                   10                  15

Phe Met Gln His
            20

<210> SEQ ID NO 146
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 146

Asp Ile Lys Glu Lys Phe Ala Lys Leu Cys Glu Ala His Gly Ile Thr
1               5                   10                  15

Arg Asp Asn Ile
            20

<210> SEQ ID NO 147
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 147

Glu Glu Ala Ser Ser Thr Arg Gly Asn Leu Asp Val Ala Lys Leu Asn
1               5                   10                  15

Gly Asp Trp Phe
            20

<210> SEQ ID NO 148
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 148

Glu Glu Asn Gly Ser Met Arg Val Phe Met Gln His Ile Asp Val Leu
1               5                   10                  15

Glu Asn Ser Leu
            20

<210> SEQ ID NO 149
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 149

Glu Asn Ser Leu Gly Phe Lys Phe Arg Ile Lys Glu Asn Gly Glu Cys
1               5                   10                  15

Arg Glu Leu Tyr
            20

<210> SEQ ID NO 150
<211> LENGTH: 21
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 150

Asp Ile Lys Tyr Thr Trp Asn Val Pro Lys Ile Ala Pro Lys Ser Glu
1               5                   10                  15

Asn Val Val Val Thr
            20

<210> SEQ ID NO 151
<211> LENGTH: 17
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 151

Asp Asn Gly Val Leu Ala Cys Ala Ile Ala Thr His Gly Lys Ile Arg
1               5                   10                  15

Asp

<210> SEQ ID NO 152
<211> LENGTH: 21
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 152

Glu Ala Leu Phe Asp Ala Asn Gln Asn Thr Lys Thr Ala Lys Ile Glu
1               5                   10                  15

Ile Lys Ala Ser Leu
            20

<210> SEQ ID NO 153
<211> LENGTH: 45
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

```
<400> SEQUENCE: 153

Gln Tyr Asp Ile Lys Tyr Thr Trp Asn Val Pro Lys Ile Ala Pro Lys
1               5                   10                  15

Ser Glu Asn Val Val Thr Val Lys Leu Ile Gly Asp Asn Gly Val
                20                  25                  30

Leu Ala Cys Ala Ile Ala Thr His Gly Lys Ile Arg Asp
                35                  40                  45

<210> SEQ ID NO 154
<211> LENGTH: 19
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 154

Thr Lys Thr Ala Lys Ile Glu Ile Lys Ala Ser Leu Asp Gly Leu Glu
1               5                   10                  15

Ile Asp Val

<210> SEQ ID NO 155
<211> LENGTH: 14
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 155

Ala Ser Ile Asp Gly Leu Gly Val Asp Val Pro Gly Ile Asp
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 156

Phe Glu Ala Val Gln Asn Thr Lys Thr Ala Lys Ile Glu Ile Lys
1               5                   10                  15

<210> SEQ ID NO 157
<211> LENGTH: 17
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 157

Arg Gly Lys Pro Pro Gln Leu Glu Ala Val Phe Glu Ala Val Gln Asn
1               5                   10                  15

Thr

<210> SEQ ID NO 158
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope
```

<400> SEQUENCE: 158

Cys His Gly Ser Glu Pro Cys Ile Ile His Arg Gly Lys Pro Phe
1               5                   10                  15

<210> SEQ ID NO 159
<211> LENGTH: 27
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 159

Cys Pro Leu Val Lys Gly Gln Gln Tyr Asp Ile Lys Tyr Thr Trp Asn
1               5                   10                  15

Val Pro Lys Ile Ala Pro Lys Ser Glu Asn Val
            20                  25

<210> SEQ ID NO 160
<211> LENGTH: 26
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 160

Asp Ile Lys Tyr Thr Trp Asn Val Pro Lys Ile Ala Pro Lys Ser Glu
1               5                   10                  15

Asn Val Val Val Thr Val Lys Val Met Gly
            20                  25

<210> SEQ ID NO 161
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 161

Asp Gln Val Asp Val Lys Asp Cys Ala Asn His Glu Ile Lys Lys
1               5                   10                  15

<210> SEQ ID NO 162
<211> LENGTH: 20
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 162

Asp Gln Val Asp Val Lys Asp Cys Ala Asn His Glu Ile Lys Lys Val
1               5                   10                  15

Leu Val Pro Gly
            20

<210> SEQ ID NO 163
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope -continued

<400> SEQUENCE: 163

Asp His Gly Val Met Ala Cys Gly Thr Val His Gly Gln Val Glu
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 164

Gly Cys Lys Phe Ile Lys Cys Pro Val Lys Lys Gly Glu Ala Leu
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 165

Gly Glu Lys Met Thr Leu Glu Ala Lys Phe Ala Ala Asn Gln Asp
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 166

Gly Glu Val Thr Glu Leu Asp Ile Thr Gly Cys Ser Gly Asp Thr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 167

Gly Lys Met Thr Phe Lys Asp Cys Gly His Gly Glu Val Thr Glu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Homo sapiens Neurofilament heavy polypeptide
      (NF-H) (Neurofilament triplet H protein) (200 kDa neurofilament
      protein) epitope

<400> SEQUENCE: 168

Tyr Gln Glu Ala Ile Gln Gln Leu Asp Ala Glu Leu Arg Asn Thr Lys
1               5                   10                  15

<210> SEQ ID NO 169

```
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 169

Ala Ala Ala Leu Pro Gly Lys Cys Gly Val
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 170

Ala Cys Cys Asn Gly Ile Arg Asn Val Asn
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 171

Ala Pro Cys Ile Pro Tyr Val Arg Gly Gly
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 172

Ile Arg Asn Val Asn Asn Leu Ala Arg Thr
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 173

Ile Ser Ala Ser Thr Asn Cys Ala Thr Val Lys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 174
```

-continued

Asn Leu Ala Arg Thr Thr Pro Asp Arg Gln
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Gallus gallus Ovalbumin epitope

<400> SEQUENCE: 175

Cys Phe Asp Val Phe Lys Glu Leu Lys Val
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Gallus gallus Ovalbumin epitope

<400> SEQUENCE: 176

Gly Ser Ile Gly Ala Ala Ser Met Glu Phe
1               5                   10

<210> SEQ ID NO 177
<211> LENGTH: 18
<212> TYPE: PRT
<213> ORGANISM: Artificial Sequence
<220> FEATURE:
<223> OTHER INFORMATION: Gallus gallus Ovalbumin epitope

<400> SEQUENCE: 177

Ile Gly Leu Phe Arg Val Ala Ser Met Ala Ser Glu Lys Met Lys Ile
1               5                   10                  15

Leu Glu

<210> SEQ ID NO 178
<211> LENGTH: 18
<212> TYPE: PRT
<213> ORGANISM: Artificial Sequence
<220> FEATURE:
<223> OTHER INFORMATION: Gallus gallus Ovalbumin epitope

<400> SEQUENCE: 178

Ile Lys His Ile Ala Thr Asn Ala Val Leu Phe Phe Gly Arg Cys Val
1               5                   10                  15

Ser Pro

<210> SEQ ID NO 179
<211> LENGTH: 13
<212> TYPE: PRT
<213> ORGANISM: Artificial Sequence
<220> FEATURE:
<223> OTHER INFORMATION: Gallus gallus Ovalbumin epitope

<400> SEQUENCE: 179

Ile Met Ser Ala Leu Ala Met Val Tyr Leu Gly Ala Lys
1               5                   10

<210> SEQ ID NO 180
<211> LENGTH: 14
<212> TYPE: PRT
<213> ORGANISM: Artificial Sequence
<220> FEATURE:
<223> OTHER INFORMATION: Gallus gallus Ovomucoid precursor epitope -continued

```
<400> SEQUENCE: 180

Ala Glu Val Asp Cys Ser Arg Phe Pro Asn Ala Thr Asp Lys
1               5                   10

<210> SEQ ID NO 181
<211> LENGTH: 14
<212> TYPE: PRT
<213> ORGANISM: Artificial Sequence
<220> FEATURE:
<223> OTHER INFORMATION: Gallus gallus Ovomucoid precursor epitope

<400> SEQUENCE: 181

Ala Thr Asp Lys Glu Gly Lys Asp Val Leu Val Cys Asn Lys
1               5                   10

<210> SEQ ID NO 182
<211> LENGTH: 17
<212> TYPE: PRT
<213> ORGANISM: Artificial Sequence
<220> FEATURE:
<223> OTHER INFORMATION: Gallus gallus Ovomucoid precursor epitope

<400> SEQUENCE: 182

Ala Val Val Glu Ser Asn Gly Thr Leu Thr Leu Ser His Phe Gly Lys
1               5                   10                  15

Cys

<210> SEQ ID NO 183
<211> LENGTH: 16
<212> TYPE: PRT
<213> ORGANISM: Artificial Sequence
<220> FEATURE:
<223> OTHER INFORMATION: Gallus gallus Ovomucoid precursor epitope

<400> SEQUENCE: 183

Cys Leu Leu Cys Ala Tyr Ser Ile Glu Phe Gly Thr Asn Ile Ser Lys
1               5                   10                  15

<210> SEQ ID NO 184
<211> LENGTH: 20
<212> TYPE: PRT
<213> ORGANISM: Artificial Sequence
<220> FEATURE:
<223> OTHER INFORMATION: Gallus gallus Ovomucoid precursor epitope

<400> SEQUENCE: 184

Asp Asn Glu Cys Leu Leu Cys Ala His Lys Val Glu Gln Gly Ala Ser
1               5                   10                  15

Val Asp Lys Arg
            20

<210> SEQ ID NO 185
<211> LENGTH: 16
<212> TYPE: PRT
<213> ORGANISM: Artificial Sequence
<220> FEATURE:
<223> OTHER INFORMATION: Musa acuminata pectate lyase epitope

<400> SEQUENCE: 185

Gly His Ser Asp Glu Leu Thr Ser Asp Lys Ser Met Gln Val Thr Ile
1               5                   10                  15

<210> SEQ ID NO 186
<211> LENGTH: 16
```

```
<212> TYPE: PRT
<213> ORGANISM: Artificial Sequence
<220> FEATURE:
<223> OTHER INFORMATION: Zinnia violacea Pectate lyase precursor epitope

<400> SEQUENCE: 186

Gly His Ser Asp Ser Tyr Thr Gln Asp Lys Asn Met Gln Val Thr Ile
1               5                   10                  15

<210> SEQ ID NO 187
<211> LENGTH: 21
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 187

Asp Gly Arg Thr Ile Ile Gln His Asp Asn Gly Tyr Gln Pro Asn Tyr
1               5                   10                  15

His Ala Val Asn Ile
            20

<210> SEQ ID NO 188
<211> LENGTH: 19
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 188

Asp Leu Arg Ser Leu Arg Thr Val Thr Pro Ile Arg Met Gln Gly Gly
1               5                   10                  15

Cys Gly Ser

<210> SEQ ID NO 189
<211> LENGTH: 19
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 189

Gly Cys Gly Ser Cys Trp Ala Phe Ser Gly Val Ala Ala Thr Glu Ser
1               5                   10                  15

Ala Tyr Leu

<210> SEQ ID NO 190
<211> LENGTH: 21
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 190

Ile Arg Glu Ala Leu Thr Gln Thr His Thr Ala Ile Ala Val Ile Ile
1               5                   10                  15

Gly Ile Lys Asp Leu
            20

<210> SEQ ID NO 191
<211> LENGTH: 19
```

-continued

```
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 191

Ile Arg Met Gln Gly Gly Cys Gly Ser Cys Trp Ala Phe Ser Gly Val
1               5                   10                  15

Ala Ala Thr

<210> SEQ ID NO 192
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 192

Phe Arg His Tyr Asp Gly Arg Thr Ile Met Gln His Asp Asn Gly Tyr
1               5                   10                  15

Gln Pro Asn

<210> SEQ ID NO 193
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 193

Gly Arg Thr Ile Met Gln His Asp Asn Gly Tyr Gln Pro Asn Tyr His
1               5                   10                  15

Ala Val Asn

<210> SEQ ID NO 194
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 194

His Ala Val Asn Ile Val Gly Tyr Gly Asn Thr Gln Gly Val Asp Tyr
1               5                   10                  15

Trp Ile Val

<210> SEQ ID NO 195
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 195

Asn Lys Ile Arg Gln Ala Leu Thr Gln Thr His Thr Ala Val Ala Val
1               5                   10                  15

Ile Ile Gly

<210> SEQ ID NO 196
```

```
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 196

Pro Tyr Val Ala Arg Glu Gln Ser Cys His Arg Pro Asn Ala Gln Arg
1               5                   10                  15

Tyr Gly Leu

<210> SEQ ID NO 197
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 197

Ala Val Gln Val Thr Phe Thr Val Gln Lys Gly Ser Asp Pro Lys
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 198

Glu Glu Trp Glu Pro Leu Thr Lys Lys Gly Asn Val Trp Glu Val
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 199

Phe Thr Val Gln Lys Gly Ser Asp Pro Lys Lys Leu Val Leu Asp
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 200

Phe Thr Val Gln Lys Gly Ser Asp Pro Lys Lys Leu Val Leu Asn
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 201

Gly Ser Asp Pro Lys Lys Leu Val Leu Asp Ile Lys Tyr Thr Arg
1               5                   10                  15
```

```
<210> SEQ ID NO 202
<211> LENGTH: 15
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 202

Cys Asp Cys Asp Asp Lys Phe Tyr Asp Cys Leu Lys Asn Ser Ala
1               5                   10                  15

<210> SEQ ID NO 203
<211> LENGTH: 12
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 203

Cys Leu His Tyr Thr Val Asp Lys Ser Lys Pro Lys
1               5                   10

<210> SEQ ID NO 204
<211> LENGTH: 15
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 204

Cys Arg Thr His Asp Met Cys Pro Asp Val Met Ser Ala Gly Glu
1               5                   10                  15

<210> SEQ ID NO 205
<211> LENGTH: 18
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 205

Asp Thr Ile Ser Ser Tyr Phe Val Gly Lys Met Tyr Phe Asn Leu Ile
1               5                   10                  15

Asp Thr

<210> SEQ ID NO 206
<211> LENGTH: 18
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 206

Glu Arg Thr Glu Gly Arg Cys Leu His Tyr Thr Val Asp Lys Ser Lys
1               5                   10                  15

Pro Lys

<210> SEQ ID NO 207
<211> LENGTH: 16
<212> TYPE: PRT
<213> ORGANISM: Artificial Sequence
```

```
<220> FEATURE:
<223> OTHER INFORMATION: Spiroplasma citri plectrovirus spv1-r8a2b orf
      14 transmembrane protein epitope

<400> SEQUENCE: 207

His Val Ile Glu Val Gln Gln Ile Asn Ser Glu Arg Ser Trp Phe Phe
1               5                   10                  15

<210> SEQ ID NO 208
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 208

Cys Gly Tyr Lys Asp Val Asp Lys Ala Pro Phe Asn Gly Met Thr Gly
1               5                   10                  15

Cys Gly Asn Thr
            20

<210> SEQ ID NO 209
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 209

Gly Ala Gly Pro Lys Asp Asn Gly Gly Ala Cys Gly Tyr Lys Asp Val
1               5                   10                  15

Asp Lys Ala Pro
            20

<210> SEQ ID NO 210
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 210

Ser Glu Val Glu Asp Val Ile Pro Glu Gly Trp Lys Ala Asp Thr Ser
1               5                   10                  15

Tyr Ser Ala Lys
            20

<210> SEQ ID NO 211
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 211

Val Glu Lys Gly Ser Asn Pro Asn Tyr Leu Ala Ile Leu Val Lys Tyr
1               5                   10                  15

Val Asp Gly Asp
            20

<210> SEQ ID NO 212
<211> LENGTH: 20
<212> TYPE: PRT
<213> ORGANISM: Artificial Sequence
<220> FEATURE:
```

<223> OTHER INFORMATION: Lolium perenne pollen allergen epitope

<400> SEQUENCE: 212

Tyr Pro Asp Asp Thr Lys Pro Thr Phe His Val Glu Lys Gly Ser Asn
1               5                   10                  15

Pro Asn Tyr Leu
            20

<210> SEQ ID NO 213
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb a
      1.1 precursor epitope

<400> SEQUENCE: 213

Gly Ala Gly Asp Glu Asn Ile Glu Asp Arg Gly Met Leu Ala Thr Val
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb a
      2 precursor epitope

<400> SEQUENCE: 214

Gly Ala Ser Asp Thr His Phe Gln Asp Leu Lys Met His Val Thr Leu
1               5                   10                  15

<210> SEQ ID NO 215
<211> LENGTH: 11
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 215

Glu Glu Ala Tyr His Ala Cys Asp Ile Lys Asp
1               5                   10

<210> SEQ ID NO 216
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 216

Gly Lys Val Tyr Leu Val Gly Gly Pro Glu Leu Gly Gly Trp Lys
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 217

Leu Gly Gly Trp Lys Leu Gln Ser Asp Pro Arg Ala Tyr Ala Leu
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 218

Pro Gly Gly Pro Asp Arg Phe Thr Leu Leu Thr Pro Gly Ser His
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 219

Ala Tyr Cys Cys Ser Asp Pro Gly Arg Tyr Cys Pro Trp Gln Val
1               5                   10                  15

<210> SEQ ID NO 220
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 220

Cys Gly Glu Lys Arg Ala Tyr Cys Cys Ser Asp Pro Gly Arg Tyr Cys
1               5                   10                  15

Pro Trp Gln Val
            20

<210> SEQ ID NO 221
<211> LENGTH: 17
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 221

Asp Pro Gly Arg Tyr Cys Pro Trp Gln Val Val Cys Tyr Glu Ser Ser
1               5                   10                  15

Glu

<210> SEQ ID NO 222
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 222

Asp Pro Gly Arg Tyr Cys Pro Trp Gln Val Val Cys Tyr Glu Ser Ser
1               5                   10                  15

Glu Ile Cys Ser
            20

-continued

<210> SEQ ID NO 223
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 223

Gly Asn Val Cys Gly Glu Lys Arg Ala Tyr Cys Cys Ser Asp Pro
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 224

Leu Val Pro Cys Ala Trp Ala Gly Asn Val Cys Gly Glu Lys Arg
1               5                   10                  15

<210> SEQ ID NO 225
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 225

Leu Val Pro Cys Ala Trp Ala Gly Asn Val Cys Gly Glu Lys Arg Ala
1               5                   10                  15

Tyr Cys Cys Ser
            20

<210> SEQ ID NO 226
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 226

Val Cys Tyr Glu Ser Ser Glu Ile Cys Ser Lys Lys Cys Gly Lys
1               5                   10                  15

<210> SEQ ID NO 227
<211> LENGTH: 20
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 227

Cys Gly Lys Val Gly Lys Tyr Cys Cys Ser Pro Ile Gly Lys Tyr Cys
1               5                   10                  15

Val Cys Tyr Asp
            20

<210> SEQ ID NO 228
<211> LENGTH: 20

```
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 228

Asp Asp Gly Leu Cys Tyr Glu Gly Thr Asn Cys Gly Lys Val Gly Lys
1               5                   10                  15

Tyr Cys Cys Ser
            20

<210> SEQ ID NO 229
<211> LENGTH: 12
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 229

Gly Lys Tyr Cys Val Cys Tyr Asp Ser Lys Ala Ile
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 230

Pro Ile Gly Lys Tyr Cys Val Cys Tyr Asp Ser Lys Ala Ile
1               5                   10

<210> SEQ ID NO 231
<211> LENGTH: 20
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 231

Pro Ile Gly Lys Tyr Cys Val Cys Tyr Asp Ser Lys Ala Ile Cys Asn
1               5                   10                  15

Lys Asn Cys Thr
            20

<210> SEQ ID NO 232
<211> LENGTH: 14
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 232

Val Cys Tyr Asp Ser Lys Ala Ile Cys Asn Lys Asn Cys Thr
1               5                   10

<210> SEQ ID NO 233
<211> LENGTH: 15
<212> TYPE: PRT
<213> ORGANISM: Artificial Sequence
<220> FEATURE:
```

<223> OTHER INFORMATION: Betula pendula pollen allergen Bet v 1 epitope

<400> SEQUENCE: 233

His Glu Val Lys Ala Glu Gln Val Lys Ala Thr Lys Glu Met Gly
1 5 10 15

<210> SEQ ID NO 234
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor epitope

<400> SEQUENCE: 234

Ala Ala Asn Lys Tyr Lys Thr Phe Val Ala Thr Phe Gly Ala Ala Ser
1 5 10 15

Asn Lys Ala Phe
20

<210> SEQ ID NO 235
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor epitope

<400> SEQUENCE: 235

Ala Ala Pro Ala Asn Asp Lys Phe Thr Val Phe Glu Ala Ala Phe Asn
1 5 10 15

Asp Ala Ile Lys
20

<210> SEQ ID NO 236
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor epitope

<400> SEQUENCE: 236

Ala Ala Val Asp Ser Ser Lys Ala Ala Leu Thr Ser Lys Leu Asp Ala
1 5 10 15

Ala Tyr Lys Leu
20

<210> SEQ ID NO 237
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor epitope

<400> SEQUENCE: 237

Ala Glu Glu Val Lys Ala Thr Pro Ala Gly Glu Leu Gln Val Ile Asp
1 5 10 15

Lys Val Asp Ala
20

<210> SEQ ID NO 238
<211> LENGTH: 20
<212> TYPE: PRT

```
<213> ORGANISM: Artificial Sequence
<220> FEATURE:
<223> OTHER INFORMATION: Poa pratensis Pollen allergen KBG 60 precursor
      epitope

<400> SEQUENCE: 238

Ala Phe Lys Val Ala Ala Thr Ala Ala Asn Ala Ala Pro Ala Asn Asp
1               5                   10                  15

Lys Phe Thr Val
            20

<210> SEQ ID NO 239
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 239

Ala Phe Gly Ser Met Ala Lys Lys Gly Glu Glu Gln Asn Val Arg Ser
1               5                   10                  15

Ala Gly Glu Leu
            20

<210> SEQ ID NO 240
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 240

Ala Gly Glu Leu Glu Leu Gln Phe Arg Arg Val Lys Cys Lys Tyr Pro
1               5                   10                  15

Asp Asp Thr Lys
            20

<210> SEQ ID NO 241
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 241

Ala Lys Ser Thr Trp Tyr Gly Lys Pro Thr Gly Ala Gly Pro Lys Asp
1               5                   10                  15

Asn Gly Gly Ala
            20

<210> SEQ ID NO 242
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 242

Ala Pro Tyr His Phe Asp Leu Ser Gly His Ala Phe Gly Ser Met Ala
1               5                   10                  15

Lys Lys Gly Glu
```

20

<210> SEQ ID NO 243
<211> LENGTH: 12
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 243

Ile Ala Pro Tyr His Phe Asp Leu Ser Gly His Ala
1               5                   10

<210> SEQ ID NO 244
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 244

Ala Ala Leu Thr Lys Ala Ile Thr Ala Met Thr Gln Ala Gln Lys Ala
1               5                   10                  15

Gly Lys Pro Ala
            20

<210> SEQ ID NO 245
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 245

Ala Ala Asn Ala Ala Pro Thr Asn Asp Lys Phe Thr Val Phe Glu Ser
1               5                   10                  15

Ala Phe Asn Lys
            20

<210> SEQ ID NO 246
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 246

Ala Asp Lys Phe Lys Ile Phe Glu Ala Ala Phe Ser Glu Ser Ser Lys
1               5                   10                  15

Gly Leu Leu Ala
            20

<210> SEQ ID NO 247
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 247

Ala Phe Ser Glu Ser Ser Lys Gly Leu Leu Ala Thr Ser Ala Ala Lys

Ala Pro Gly Leu
            20

<210> SEQ ID NO 248
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 248

Ala Tyr Ala Ala Thr Val Ala Ala Ala Pro Glu Val Lys Tyr Ala Val
1               5                   10                  15

Phe Glu Ala Ala
            20

<210> SEQ ID NO 249
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 249

Ala Cys Ser Gly Glu Pro Val Val Val His Ile Thr
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 250

Ala Glu Asp Val Ile Pro Glu Gly Trp Lys Ala Asp
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 251

Ala Gly Glu Leu Glu Leu Gln Phe Arg Arg Val Lys
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 252

Asp Lys Trp Ile Glu Leu Lys Glu Ser Trp Gly Ala
1               5                   10

<210> SEQ ID NO 253
<211> LENGTH: 12
<212> TYPE: PRT
<213> ORGANISM: Artificial Sequence

```
<220> FEATURE:
<223> OTHER INFORMATION: Phleum pratense Pollen allergen Phl p 1 epitope

<400> SEQUENCE: 253

Asp Lys Trp Leu Asp Ala Lys Ser Thr Trp Tyr Gly
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 254

Phe Glu Ile Lys Cys Thr Lys Pro Glu Ala Cys Ser
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 255

Tyr His Phe Asp Leu Ser Gly His Ala Phe Gly Ala
1               5                   10

<210> SEQ ID NO 256
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 256

Glu Leu Lys Glu Ser Trp Gly Ala Ile Trp Arg Ile Asp Thr Pro
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 257

Glu Pro Ile Ala Pro Tyr His Phe Asp Leu Ser Gly His Ala Phe
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 258

Phe Glu Ile Lys Cys Thr Lys Pro Glu Ala Cys Ser Gly Glu Pro
1               5                   10                  15
```

-continued

```
<210> SEQ ID NO 259
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 259

Trp Gly Ala Ile Trp Arg Ile Asp Thr Pro Asp Lys Leu Thr Gly
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Phleum pratense Pollen allergen Phl p 11
      epitope

<400> SEQUENCE: 260

Arg Tyr Ala Asn Pro Ile Ala Phe Phe Arg Lys Glu Pro Leu Lys
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 261

Glu His Gly Ser Asp Glu Trp Val Ala Met Thr Lys Gly Glu Gly
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 262

Glu Trp Val Ala Met Thr Lys Gly Glu Gly Gly Val Trp Thr Phe
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 263

Gly Val Trp Thr Phe Asp Ser Glu Glu Pro Leu Gln Gly Pro Phe
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 264

Lys Asn Val Phe Asp Asp Val Val Pro Glu Lys Tyr Thr Ile Gly
1               5                   10                  15
```

```
<210> SEQ ID NO 265
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 265

Leu Gln Gly Pro Phe Asn Phe Arg Phe Leu Thr Glu Lys Gly Met
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 266

Phe Lys Pro Phe Ala Glu Tyr Lys Ser Asp Tyr Val Tyr Glu Pro
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 267

Phe Pro Lys Glu Val Trp Glu Gln Ile Phe Ser Thr Trp Leu Leu
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 268

Phe Val His Leu Gly His Arg Asp Asn Ile Glu Asp Asp Leu Leu
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 269

Gly Ile Val Val Ala Trp Lys Val Arg Leu Leu Pro Val Pro Pro
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 270

Asn Arg Asn Asn Thr Phe Lys Pro Phe Ala Glu Tyr Lys Ser Asp
1               5                   10                  15
```

```
<210> SEQ ID NO 271
<211> LENGTH: 12
<212> TYPE: PRT
<213> ORGANISM: Artificial Sequence
<220> FEATURE:
<223> OTHER INFORMATION: Phleum pratense Pollen allergen Phl p 5a
      epitope

<400> SEQUENCE: 271

Glu Val Lys Tyr Thr Val Phe Glu Thr Ala Leu Lys
1               5                   10

<210> SEQ ID NO 272
<211> LENGTH: 19
<212> TYPE: PRT
<213> ORGANISM: Artificial Sequence
<220> FEATURE:
<223> OTHER INFORMATION: Phleum pratense Pollen allergen Phl p 5a
      epitope

<400> SEQUENCE: 272

Asn Ala Gly Phe Lys Ala Ala Leu Ala Gly Ala Gly Val Gln Pro Ala
1               5                   10                  15

Asp Lys Tyr

<210> SEQ ID NO 273
<211> LENGTH: 27
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 273

Ala Ala Gly Lys Ala Thr Thr Glu Glu Gln Lys Leu Ile Glu Asp Ile
1               5                   10                  15

Asn Val Gly Phe Lys Ala Ala Val Ala Ala Ala
            20                  25

<210> SEQ ID NO 274
<211> LENGTH: 33
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 274

Ala Ala Gly Lys Ala Thr Thr Glu Glu Gln Lys Leu Ile Glu Asp Ile
1               5                   10                  15

Asn Val Gly Phe Lys Ala Ala Val Ala Ala Ala Ser Val Pro Ala
            20                  25                  30

Ala

<210> SEQ ID NO 275
<211> LENGTH: 19
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 275

Ala Ala Val Ala Ala Ala Ala Ser Val Pro Ala Ala Asp Lys Phe Lys
1               5                   10                  15
```

Thr Phe Glu

<210> SEQ ID NO 276
<211> LENGTH: 27
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 276

Ala Lys Phe Asp Ser Phe Val Ala Ser Leu Thr Glu Ala Leu Arg Val
1               5                   10                  15

Ile Ala Gly Ala Leu Glu Val His Ala Val Lys
            20                  25

<210> SEQ ID NO 277
<211> LENGTH: 19
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 277

Ala Met Ser Glu Val Gln Lys Val Ser Gln Pro Ala Thr Gly Ala Ala
1               5                   10                  15

Thr Val Ala

<210> SEQ ID NO 278
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 278

Ala Arg Trp Lys Asn Ser Lys Ile Trp Leu Gln Phe Ala Gln Leu Thr
1               5                   10                  15

Asp Phe Asn Leu
            20

<210> SEQ ID NO 279
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 279

Ala Val Leu Leu Val Pro Ala Asn Lys Lys Phe Phe Val Asn Asn Leu
1               5                   10                  15

Val Phe Arg Gly
            20

<210> SEQ ID NO 280
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 280

Asp Gly Thr Ile Val Ala Gln Pro Asp Pro Ala Arg Trp Lys Asn Ser
1               5                   10                  15

Lys Ile Trp Leu
            20

<210> SEQ ID NO 281
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 281

Phe Phe Val Asn Asn Leu Val Phe Arg Gly Pro Cys Gln Pro His Leu
1               5                   10                  15

Ser Phe Lys Val
            20

<210> SEQ ID NO 282
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 282

Phe Gly Glu Cys Glu Gly Val Lys Ile Gln Gly Leu Lys Ile Lys Ala
1               5                   10                  15

Pro Arg Asp Ser
            20

<210> SEQ ID NO 283
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 283

Ala Ala Tyr Gln Asn Pro Ala Ser Trp Lys Asn Asn Arg Ile Trp
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 284

Ala Cys Lys Lys Pro Ser Ala Met Leu Leu Val Pro Gly Asn Lys
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 285

Ala Ile Lys Phe Asp Phe Ser Thr Gly Leu Ile Ile Gln Gly Leu
1               5                   10                  15

```
<210> SEQ ID NO 286
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 286

Ala Ile Asn Ile Phe Asn Val Glu Lys Tyr Gly Ala Val Gly Asp
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 287

Ala Asn Gly Tyr Phe Ser Gly His Val Ile Pro Ala Cys Lys Asn
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Arabidopsis thaliana Probable pectate lyase 18
      precursor epitope

<400> SEQUENCE: 288

Gly His Ser Asp Thr Tyr Ser Arg Asp Lys Asn Met Gln Val Thr Ile
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Phleum pratense Profilin-2/4 epitope

<400> SEQUENCE: 289

Leu Gly His Asp Gly Thr Val Trp Ala Gln Ser Ala Asp Phe Pro
1               5                   10                  15

<210> SEQ ID NO 290
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 290

Asp Glu Tyr Cys Ser Pro Asp His Asn Cys Gln Ser Asn Cys Lys Asp
1               5                   10                  15

Ser Gly Glu Gly
            20

<210> SEQ ID NO 291
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 291
```

```
Glu Gln Cys Gly Arg Gln Ala Gly Gly Lys Leu Cys Pro Asn Asn Leu
1               5                   10                  15

Cys Cys Ser Gln
            20

<210> SEQ ID NO 292
<211> LENGTH: 43
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 292

Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp
        35                  40

<210> SEQ ID NO 293
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 293

Lys Leu Cys Pro Asn Asn Leu Cys Cys Ser Gln Trp Gly Trp Cys Gly
1               5                   10                  15

Ser Thr Asp Glu
            20

<210> SEQ ID NO 294
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 294

Asn Gly Gly Leu Asp Leu Asp Val Asn Val Phe Arg Gln Leu Asp Thr
1               5                   10                  15

Asp Gly Lys Gly
            20

<210> SEQ ID NO 295
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 295

Gly Lys Cys Gly Val Ser Ile Pro Tyr Lys
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Prunus persica pru p 1 epitope
```

```
<400> SEQUENCE: 296

Ile Thr Cys Gly Gln Val Ser Ser Ser Leu
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 297

Ser Ile Pro Tyr Lys Ile Ser Ala Ser Thr
1               5                   10

<210> SEQ ID NO 298
<211> LENGTH: 15
<212> TYPE: PRT
<213> ORGANISM: Artificial Sequence
<220> FEATURE:
<223> OTHER INFORMATION: Prunus persica pru p 1 epitope

<400> SEQUENCE: 298

Asp Arg Gln Ala Ala Cys Asn Cys Leu Lys Gln Leu Ser Ala Ser
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Prunus persica pru p 1 epitope

<400> SEQUENCE: 299

Val Asn Pro Asn Asn Ala Ala Ala Leu Pro Gly Lys Cys Gly Val
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Arabidopsis thaliana Putative pectate lyase 17
      precursor epitope

<400> SEQUENCE: 300

Gly His Asn Asp Asn Phe Val Lys Asp Val Lys Met Lys Val Thr Val
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: Homo sapiens RAD51-like 1 isoform 1 epitope

<400> SEQUENCE: 301

Thr Arg Leu Ile Leu Gln Tyr Leu Asp Ser Glu Arg Arg Gln Ile Leu
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: Aspergillus fumigatus Ribonuclease mitogillin
      precursor epitope
```

```
<400> SEQUENCE: 302

Asp Pro Gly Pro Ala Arg Val Ile Tyr Thr Tyr Pro Asn Lys Val Phe
1               5                   10                  15

<210> SEQ ID NO 303
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 303

Ala Thr Trp Thr Cys Ile Asn Gln Gln Leu Asn Pro Lys Thr Asn Lys
1               5                   10                  15

Trp Glu Asp Lys
            20

<210> SEQ ID NO 304
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 304

His Tyr Leu Leu Glu Phe Pro Thr Phe Pro Asp Gly His Asp Tyr Lys
1               5                   10                  15

Phe Asp Ser Lys
            20

<210> SEQ ID NO 305
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 305

Lys Phe Asp Ser Lys Lys Pro Lys Glu Asp Pro Gly Pro Ala Arg Val
1               5                   10                  15

Ile Tyr Thr Tyr
            20

<210> SEQ ID NO 306
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 306

Leu Ile Lys Gly Arg Thr Pro Ile Lys Phe Gly Lys Ala Asp Cys Asp
1               5                   10                  15

Arg Pro Pro Lys
            20

<210> SEQ ID NO 307
<211> LENGTH: 20
<212> TYPE: PRT
<213> ORGANISM: Artificial Sequence
```

```
<220> FEATURE:
<223> OTHER INFORMATION: Aspergillus fumigatus Ribonuclease mitogillin
      precursor epitope

<400> SEQUENCE: 307

Ser Tyr Pro His

```
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 312

Arg Ser Leu Pro Pro Ile Val Lys Asp Ala Ser Ile Gln Val Val Ser
1               5                   10                  15

Ala Ile Arg

<210> SEQ ID NO 313
<211> LENGTH: 17
<212> TYPE: PRT
<213> ORGANISM: Artificial Sequence
<220> FEATURE:
<223> OTHER INFORMATION: Bos taurus Serum albumin precursor epitope

<400> SEQUENCE: 313

Asp Asp Ser Pro Asp Leu Pro Lys Leu Lys Pro Asp Pro Asn Thr Leu
1               5                   10                  15

Cys

<210> SEQ ID NO 314
<211> LENGTH: 20
<212> TYPE: PRT
<213> ORGANISM: Artificial Sequence
<220> FEATURE:
<223> OTHER INFORMATION: Bos taurus Serum albumin precursor epitope

<400> SEQUENCE: 314

Glu Lys Asp Ala Ile Pro Glu Asn Leu Pro Pro Leu Thr Ala Asp Phe
1               5                   10                  15

Ala Glu Asp Lys
            20

<210> SEQ ID NO 315
<211> LENGTH: 9
<212> TYPE: PRT
<213> ORGANISM: Artificial Sequence
<220> FEATURE:
<223> OTHER INFORMATION: Bos taurus Serum albumin precursor epitope

<400> SEQUENCE: 315

Glu Ser His Ala Gly Cys Glu Lys Ser
1               5

<210> SEQ ID NO 316
<211> LENGTH: 10
<212> TYPE: PRT
<213> ORGANISM: Artificial Sequence
<220> FEATURE:
<223> OTHER INFORMATION: Bos taurus Serum albumin precursor epitope

<400> SEQUENCE: 316

His Pro Glu Tyr Ala Val Ser Val Leu Leu
1               5                   10

<210> SEQ ID NO 317
<211> LENGTH: 9
<212> TYPE: PRT
<213> ORGANISM: Artificial Sequence
<220> FEATURE:
<223> OTHER INFORMATION: Bos taurus Serum albumin precursor epitope

<400> SEQUENCE: 317
```

```
Leu Ser Leu Ile Leu Asn Arg Leu Cys
1               5

<210> SEQ ID NO 318
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 318

Asp Phe Val Arg Ala Ala Gly Val Tyr Ala Val Asp
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 319

Lys Tyr Leu Asp Phe Val Arg Ala Ala Gly Val Tyr
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 320

Asn Val Val Lys Thr Val Val Thr Pro Val Tyr Tyr
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 321

Pro Arg Ile Val Leu Asp Val Ala Ser Ser Val Phe
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 322

Gln Gly Tyr Arg Val Ser Ser Tyr Leu Pro Leu Leu
1               5                   10

<210> SEQ ID NO 323
<211> LENGTH: 15
<212> TYPE: PRT
<213> ORGANISM: Artificial Sequence
```

```
<220> FEATURE:
<223> OTHER INFORMATION: Glycine max Stress-induced protein SAM22
      epitope

<400> SEQUENCE: 323

Ala Leu Phe Lys Ala Ile Glu Ala Tyr Leu Leu Ala His Pro Asp
1               5                   10                  15

<210> SEQ ID NO 324
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 324

Ala Phe Asn Val Glu Asn Gly Asn Ala Thr Pro Gln Leu Thr Lys
1               5                   10                  15

<210> SEQ ID NO 325
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 325

Ala Asn Asn Asn Tyr Asp Pro Trp Thr Ile Tyr Ala Ile Gly Gly
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 326

Ala Tyr Ser Asp Asp Lys Ser Met Lys Val Thr Val Ala Phe Asn
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 327

Cys Gly Gln Arg Met Pro Arg Ala Arg Tyr Gly Leu Val His Val
1               5                   10                  15

<210> SEQ ID NO 328
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 328

Cys Ser Asn Trp Val Trp Gln Ser Thr Gln Asp Val Phe Tyr Asn
1               5                   10                  15
```

<210> SEQ ID NO 329
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 329

```
Ala Asp Phe Ser Asn Tyr Gly Ala Val Val Asp Val Tyr Ala Pro Gly
1               5                   10                  15

Lys Asp Ile Thr
            20
```

<210> SEQ ID NO 330
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 330

```
Ala Lys Gly Val Ser Leu Val Ala Val Lys Val Leu Asp Cys Asp Gly
1               5                   10                  15

Ser Gly Ser Asn
            20
```

<210> SEQ ID NO 331
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 331

```
Ala Ser Asn Gln Ala Ala Lys Ala Ile Ser Asp Ala Gly Ile Phe Met
1               5                   10                  15

Ala Val Ala Ala
            20
```

<210> SEQ ID NO 332
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 332

```
Asp Cys Asn Gly His Gly Thr His Val Ala Gly Thr Val Gly Gly Thr
1               5                   10                  15

Lys Tyr Gly Leu
            20
```

<210> SEQ ID NO 333
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 333

```
Asp Pro Ser Ala Gly Lys Gly Val Thr Ala Tyr Ile Ile Asp Thr Gly
1               5                   10                  15

Ile Asp Ile Asp
            20
```

<210> SEQ ID NO 334
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 334

Ala Cys Lys Tyr Gly Ser Leu Lys Pro Asn Cys Gly
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 335

Cys Asn Tyr Gly Pro Ser Gly Asn Phe Met Asn Glu
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 336

Asp Val Ala Lys Tyr Gln Val Gly Gln Asn Val Ala
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 337

Glu Lys Trp His Lys His Tyr Leu Val Cys Asn Tyr
1               5                   10

<210> SEQ ID NO 338
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 338

Glu Leu Ala Tyr Val Ala Gln Val Trp Ala Asn Gln
1               5                   10

<210> SEQ ID NO 339
<211> LENGTH: 15
<212> TYPE: PRT
<213> ORGANISM: Artificial Sequence
<220> FEATURE:
<223> OTHER INFORMATION: Corylus avellana 11S globulin-like protein
      epitope

```
<400> SEQUENCE: 339

Ala Phe Gln Ile Ser Arg Glu Glu Ala Arg Arg Leu Lys Tyr Asn
1               5                   10                  15

<210> SEQ ID NO 340
<211> LENGTH: 12
<212> TYPE: PRT
<213> ORGANISM: Artificial Sequence
<220> FEATURE:
<223> OTHER INFORMATION: Carya illinoinensis 11S legumin protein
      epitope

<400> SEQUENCE: 340

Glu Glu Ser Gln Arg Gln Ser Gln Gln Gly Gln Arg
1               5                   10

<210> SEQ ID NO 341
<211> LENGTH: 18
<212> TYPE: PRT
<213> ORGANISM: Artificial Sequence
<220> FEATURE:
<223> OTHER INFORMATION: Fagopyrum esculentum 13S globulin epitope

<400> SEQUENCE: 341

Asp Ala His Gln Pro Thr Arg Arg Val Arg Lys Gly Asp Val Val Ala
1               5                   10                  15

Leu Pro

<210> SEQ ID NO 342
<211> LENGTH: 12
<212> TYPE: PRT
<213> ORGANISM: Artificial Sequence
<220> FEATURE:
<223> OTHER INFORMATION: Fagopyrum esculentum 13S globulin seed storage
      protein 1 precursor (Legumin-like protein 1) epitope

<400> SEQUENCE: 342

Phe Lys Gln Asn Val Asn Arg Pro Ser Arg Ala Asp
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Fagopyrum esculentum 13S globulin seed storage
      protein 3 precursor (Legumin-like protein 3) (Allergen Fag e 1)
      epitope

<400> SEQUENCE: 343

Asp Ile Ser Thr Lys Glu Ala Phe Arg Leu Lys Asn
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Anacardium occidentale 2s albumin epitope

<400> SEQUENCE: 344

Cys Gln Arg Gln Phe Glu Glu Gln Gln Arg Phe Arg
1               5                   10

<210> SEQ ID NO 345
```

```
<211> LENGTH: 10
<212> TYPE: PRT
<213> ORGANISM: Artificial Sequence
<220> FEATURE:
<223> OTHER INFORMATION: Sesamum indicum 2S seed storage protein 1
      epitope

<400> SEQUENCE: 345

His Phe Arg Glu Cys Cys Asn Glu Ile Arg
1               5                   10

<210> SEQ ID NO 346
<211> LENGTH: 10
<212> TYPE: PRT
<213> ORGANISM: Artificial Sequence
<220> FEATURE:
<223> OTHER INFORMATION: Sesamum indicum 2S seed storage protein 1
      precursor epitope

<400> SEQUENCE: 346

Cys Met Gln Trp Met Arg Ser Met Arg Gly
1               5                   10

<210> SEQ ID NO 347
<211> LENGTH: 14
<212> TYPE: PRT
<213> ORGANISM: Artificial Sequence
<220> FEATURE:
<223> OTHER INFORMATION: Bertholletia excelsa 2S sulfur-rich seed
      storage protein precursor (Allergen Ber e 1) epitope

<400> SEQUENCE: 347

Cys Arg Cys Glu Gly Leu Arg Met Met Met Met Arg Met Gln
1               5                   10

<210> SEQ ID NO 348
<211> LENGTH: 21
<212> TYPE: PRT
<213> ORGANISM: Artificial Sequence
<220> FEATURE:
<223> OTHER INFORMATION: Cynodon dactylon acidic Cyn d 1 isoallergen
      isoform 1 precursor epitope

<400> SEQUENCE: 348

Gln Asp Asp Val Ile Pro Glu Asp Trp Lys Pro Asp Thr Val Tyr Lys
1               5                   10                  15

Ser Lys Ile Gln Phe
            20

<210> SEQ ID NO 349
<211> LENGTH: 50
<212> TYPE: PRT
<213> ORGANISM: Artificial Sequence
<220> FEATURE:
<223> OTHER INFORMATION: Cynodon dactylon acidic Cyn d 1 isoallergen
      isoform 3 precursor epitope

<400> SEQUENCE: 349

Glu Glu Asp Lys Leu Arg Lys Ala Gly Glu Leu Met Leu Gln Phe Arg
1               5                   10                  15

Arg Val Lys Cys Glu Tyr Pro Ser Asp Thr Lys Ile Thr Phe His Val
            20                  25                  30

Glu Lys Gly Ser Ser Pro Asn Tyr Leu Ala Leu Leu Val Lys Tyr Ala
        35                  40                  45

Ala Gly
    50
```

<210> SEQ ID NO 350
<211> LENGTH: 7
<212> TYPE: PRT
<213> ORGANISM: Artificial Sequence
<220> FEATURE:
<223> OTHER INFORMATION: Bos taurus albumin epitope

<400> SEQUENCE: 350

Pro Val Glu Ser Lys Val Thr
1               5

<210> SEQ ID NO 351
<211> LENGTH: 13
<212> TYPE: PRT
<213> ORGANISM: Artificial Sequence
<220> FEATURE:
<223> OTHER INFORMATION: Juglans regia Albumin seed storage protein
      epitope

<400> SEQUENCE: 351

Gly Leu Arg Gly Glu Glu Met Glu Glu Met Val Gln Ser
1               5                   10

<210> SEQ ID NO 352
<211> LENGTH: 18
<212> TYPE: PRT
<213> ORGANISM: Artificial Sequence
<220> FEATURE:
<223> OTHER INFORMATION: Cochliobolus lunatus alcohol dehydrogenase
      epitope

<400> SEQUENCE: 352

Ala Val Asn Gly Asp Trp Pro Leu Pro Thr Lys Leu Pro Leu Val Gly
1               5                   10                  15

Gly His

<210> SEQ ID NO 353
<211> LENGTH: 37
<212> TYPE: PRT
<213> ORGANISM: Artificial Sequence
<220> FEATURE:
<223> OTHER INFORMATION: Penicillium chrysogenum alkaline serine
      protease epitope

<400> SEQUENCE: 353

Ala Asn Val Val Gln Arg Asn Ala Pro Ser Trp Gly Leu Ser Arg Ile
1               5                   10                  15

Ser Ser Lys Lys Ser Gly Ala Thr Asp Tyr Val Tyr Asp Ser Thr Ala
            20                  25                  30

Gly Glu Gly Ile Val
        35

<210> SEQ ID NO 354
<211> LENGTH: 10
<212> TYPE: PRT
<213> ORGANISM: Artificial Sequence
<220> FEATURE:
<223> OTHER INFORMATION: Arachis hypogaea allergen epitope

<400> SEQUENCE: 354

Asp Asp Gln Cys Gln Arg Gln Leu Gln Arg
1               5                   10

<210> SEQ ID NO 355

```
<211> LENGTH: 15
<212> TYPE: PRT
<213> ORGANISM: Artificial Sequence
<220> FEATURE:
<223> OTHER INFORMATION: Anacardium occidentale allergen Ana o 2 epitope

<400> SEQUENCE: 355

Glu Glu Ser Glu Asp Glu Lys Arg Arg Trp Gly Gln Arg Asp Asn
1               5                   10                  15

<210> SEQ ID NO 356
<211> LENGTH: 10
<212> TYPE: PRT
<213> ORGANISM: Artificial Sequence
<220> FEATURE:
<223> OTHER INFORMATION: Arachis hypogaea Allergen Ara h 1, clone P41B
      precursor epitope

<400> SEQUENCE: 356

Ala Lys Ser Ser Pro Tyr Gln Lys Lys Thr
1               5                   10

<210> SEQ ID NO 357
<211> LENGTH: 15
<212> TYPE: PRT
<213> ORGANISM: Artificial Sequence
<220> FEATURE:
<223> OTHER INFORMATION: Arachis hypogaea allergen Arah3/Arah4 epitope

<400> SEQUENCE: 357

Ala Gly Val Ala Leu Ser Arg Leu Val Leu Arg Arg Asn Ala Leu
1               5                   10                  15

<210> SEQ ID NO 358
<211> LENGTH: 10
<212> TYPE: PRT
<213> ORGANISM: Artificial Sequence
<220> FEATURE:
<223> OTHER INFORMATION: Arachis hypogaea allergen Arah6 epitope

<400> SEQUENCE: 358

Asp Arg Gln Met Val Gln His Phe Lys Arg
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Periplaneta americana Allergen Cr-PI epitope

<400> SEQUENCE: 359

Ile Pro Lys Gly Lys Lys Gly Gly Gln Ala Tyr
1               5                   10

<210> SEQ ID NO 360
<211> LENGTH: 8
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 360

Ile Asn Gln Gln Leu Asn Pro Lys
1               5
```

```
<210> SEQ ID NO 361
<211> LENGTH: 10
<212> TYPE: PRT
<213> ORGANISM: Artificial Sequence
<220> FEATURE:
<223> OTHER INFORMATION: Arachis hypogaea Allergen II epitope

<400> SEQUENCE: 361

Asp Arg Leu Gln Gly Arg Gln Gln Glu Gln
1               5                   10

<210> SEQ ID NO 362
<211> LENGTH: 15
<212> TYPE: PRT
<213> ORGANISM: Artificial Sequence
<220> FEATURE:
<223> OTHER INFORMATION: Lens culinaris allergen Len c 1.0101 epitope

<400> SEQUENCE: 362

Ala Ile Asn Ala Ser Ser Asp Leu Asn Leu Ile Gly Phe Gly Ile
1               5                   10                  15

<210> SEQ ID NO 363
<211> LENGTH: 12
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 363

Asp Val Glu Leu Ser Leu Arg Ser Ser Asp Ile Ala
1               5                   10

<210> SEQ ID NO 364
<211> LENGTH: 31
<212> TYPE: PRT
<213> ORGANISM: Artificial Sequence
<220> FEATURE:
<223> OTHER INFORMATION: Penicillium chrysogenum Allergen Pen n 18
      epitope

<400> SEQUENCE: 364

Ala His Ile Lys Lys Ser Lys Lys Gly Asp Lys Lys Phe Lys Gly Ser
1               5                   10                  15

Val Ala Asn Met Ser Leu Gly Gly Gly Ser Ser Arg Thr Leu Asp
            20                  25                  30

<210> SEQ ID NO 365
<211> LENGTH: 14
<212> TYPE: PRT
<213> ORGANISM: Artificial Sequence
<220> FEATURE:
<223> OTHER INFORMATION: Sinapis alba Allergen Sin a 1 epitope

<400> SEQUENCE: 365

Gln Gly Pro His Val Ile Ser Arg Ile Tyr Gln Thr Ala Thr
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Ziziphus mauritiana allergen Ziz m 1 epitope

<400> SEQUENCE: 366

Lys Thr Asn Tyr Ser Ser Ser Ile Ile Leu Glu Tyr
```

```
1               5               10
```

<210> SEQ ID NO 367
<211> LENGTH: 37
<212> TYPE: PRT
<213> ORGANISM: Artificial Sequence
<220> FEATURE:
<223> OTHER INFORMATION: Fagopyrum tataricum allergenic protein epitope

<400> SEQUENCE: 367

```
Asp Ile Ser Thr Glu Glu Ala Tyr Lys Leu Lys Asn Gly Arg Gln Glu
1               5                   10                  15

Val Glu Val Phe Arg Pro Phe Gln Ser Arg Tyr Glu Lys Glu Glu Glu
            20                  25                  30

Lys Glu Arg Glu Arg
        35
```

<210> SEQ ID NO 368
<211> LENGTH: 30
<212> TYPE: PRT
<213> ORGANISM: Artificial Sequence
<220> FEATURE:
<223> OTHER INFORMATION: Bos taurus alpha S1 casein epitope

<400> SEQUENCE: 368

```
Glu Asp Gln Ala Met Glu Asp Ile Lys Gln Met Glu Ala Glu Ser Ile
1               5                   10                  15

Ser Ser Ser Glu Glu Ile Val Pro Asn Ser Val Glu Gln Lys
            20                  25                  30
```

<210> SEQ ID NO 369
<211> LENGTH: 10
<212> TYPE: PRT
<213> ORGANISM: Artificial Sequence
<220> FEATURE:
<223> OTHER INFORMATION: Triticum aestivum Alpha/beta-gliadin A-II
      precursor epitope

<400> SEQUENCE: 369

```
Gln Val Ser Phe Gln Gln Pro Gln Gln Gln
1               5                   10
```

<210> SEQ ID NO 370
<211> LENGTH: 10
<212> TYPE: PRT
<213> ORGANISM: Artificial Sequence
<220> FEATURE:
<223> OTHER INFORMATION: Triticum aestivum Alpha/beta-gliadin A-V
      epitope

<400> SEQUENCE: 370

```
Leu Ala Leu Gln Thr Leu Pro Ala Met Cys
1               5                   10
```

<210> SEQ ID NO 371
<211> LENGTH: 20
<212> TYPE: PRT
<213> ORGANISM: Artificial Sequence
<220> FEATURE:
<223> OTHER INFORMATION: Bos taurus alpha2(I) collagen epitope

<400> SEQUENCE: 371

```
Leu Pro Gly Leu Lys Gly His Asn Gly Leu Gln Gly Leu Pro Gly Leu
1               5                   10                  15

Ala Gly His His
```

-continued

```
                         20

<210> SEQ ID NO 372
<211> LENGTH: 5
<212> TYPE: PRT
<213> ORGANISM: Artificial Sequence
<220> FEATURE:
<223> OTHER INFORMATION: Triticum aestivum Alpha-amylase inhibitor 0.28
      precursor (CIII) (WMAI-1) epitope

<400> SEQUENCE: 372

Ala Tyr Pro Asp Val
1               5

<210> SEQ ID NO 373
<211> LENGTH: 12
<212> TYPE: PRT
<213> ORGANISM: Artificial Sequence
<220> FEATURE:
<223> OTHER INFORMATION: Triticum aestivum Alpha-gliadin epitope

<400> SEQUENCE: 373

Leu Gly Gln Gly Ser Phe Arg Pro Ser Gln Gln Asn
1               5                   10

<210> SEQ ID NO 374
<211> LENGTH: 10
<212> TYPE: PRT
<213> ORGANISM: Artificial Sequence
<220> FEATURE:
<223> OTHER INFORMATION: Bos taurus Alpha-lactalbumin epitope

<400> SEQUENCE: 374

Lys Asp Leu Lys Gly Tyr Gly Gly Val Ser
1               5                   10

<210> SEQ ID NO 375
<211> LENGTH: 14
<212> TYPE: PRT
<213> ORGANISM: Artificial Sequence
<220> FEATURE:
<223> OTHER INFORMATION: Bos taurus Alpha-lactalbumin precursor epitope

<400> SEQUENCE: 375

Lys Cys Glu Val Phe Arg Glu Leu Lys Asp Leu Lys Gly Tyr
1               5                   10

<210> SEQ ID NO 376
<211> LENGTH: 20
<212> TYPE: PRT
<213> ORGANISM: Artificial Sequence
<220> FEATURE:
<223> OTHER INFORMATION: Bos taurus alpha-S1-casein epitope

<400> SEQUENCE: 376

Leu Asn Glu Asn Leu Leu Arg Phe Phe Val Ala Pro Phe Pro Gln Val
1               5                   10                  15

Phe Gly Lys Glu
            20

<210> SEQ ID NO 377
<211> LENGTH: 10
<212> TYPE: PRT
<213> ORGANISM: Artificial Sequence
<220> FEATURE:
<223> OTHER INFORMATION: Bos taurus Alpha-S1-casein precursor epitope
```

```
<400> SEQUENCE: 377

Ala Met Glu Asp Ile Lys Gln Met Glu Ala
1               5                   10

<210> SEQ ID NO 378
<211> LENGTH: 10
<212> TYPE: PRT
<213> ORGANISM: Artificial Sequence
<220> FEATURE:
<223> OTHER INFORMATION: Bos taurus Alpha-S2-casein precursor epitope

<400> SEQUENCE: 378

Glu Asn Leu Cys Ser Thr Phe Cys Lys Glu
1               5                   10

<210> SEQ ID NO 379
<211> LENGTH: 15
<212> TYPE: PRT
<213> ORGANISM: Artificial Sequence
<220> FEATURE:
<223> OTHER INFORMATION: Arachis hypogaea Ara h 2.01 allergen epitope

<400> SEQUENCE: 379

Cys Cys Asn Glu Leu Asn Glu Phe Glu Asn Asn Gln Arg Cys Met
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: Glycine max Bd 30K (34 kDa maturing seed
      protein) epitope

<400> SEQUENCE: 380

Glu Asp Trp Gly Glu Asp Gly Tyr Ile Trp Ile Gln Arg Asn Thr
1               5                   10                  15

<210> SEQ ID NO 381
<211> LENGTH: 8
<212> TYPE: PRT
<213> ORGANISM: Artificial Sequence
<220> FEATURE:
<223> OTHER INFORMATION: Betula pendula Bet v 4 epitope

<400> SEQUENCE: 381

Phe Ala Arg Ala Asn Arg Gly Leu
1               5

<210> SEQ ID NO 382
<211> LENGTH: 9
<212> TYPE: PRT
<213> ORGANISM: Artificial Sequence
<220> FEATURE:
<223> OTHER INFORMATION: Musa acuminata beta-1, 3-glucananse epitope

<400> SEQUENCE: 382

Gly Leu Phe Tyr Pro Asn Lys Gln Pro
1               5

<210> SEQ ID NO 383
<211> LENGTH: 15
<212> TYPE: PRT
<213> ORGANISM: Artificial Sequence
<220> FEATURE:
<223> OTHER INFORMATION: Hevea brasiliensis beta-1,3-glucanase epitope
```

```
-continued

<400> SEQUENCE: 383

Gly Leu Phe Phe Pro Asp Lys Arg Pro Lys Tyr Asn Leu Asn Phe
1               5                   10                  15

<210> SEQ ID NO 384
<211> LENGTH: 12
<212> TYPE: PRT
<213> ORGANISM: Artificial Sequence
<220> FEATURE:
<223> OTHER INFORMATION: Olea europaea beta-1,3-glucanase-like protein
      epitope

<400> SEQUENCE: 384

Ala Gly Arg Asn Ser Trp Asn Cys Asp Phe Ser Gln
1               5                   10

<210> SEQ ID NO 385
<211> LENGTH: 13
<212> TYPE: PRT
<213> ORGANISM: Artificial Sequence
<220> FEATURE:
<223> OTHER INFORMATION: Bos taurus beta-casein epitope

<400> SEQUENCE: 385

Gln Ser Lys Val Leu Pro Val Pro Gln Lys Ala Val Pro
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Bos taurus Beta-casein precursor epitope

<400> SEQUENCE: 386

Asp Glu Leu Gln Asp Lys Ile His Pro Phe Ala Gln
1               5                   10

<210> SEQ ID NO 387
<211> LENGTH: 10
<212> TYPE: PRT
<213> ORGANISM: Artificial Sequence
<220> FEATURE:
<223> OTHER INFORMATION: Bos taurus Beta-lactoglobulin epitope

<400> SEQUENCE: 387

Ala Gln Lys Lys Ile Ile Ala Glu Lys Thr
1               5                   10

<210> SEQ ID NO 388
<211> LENGTH: 16
<212> TYPE: PRT
<213> ORGANISM: Artificial Sequence
<220> FEATURE:
<223> OTHER INFORMATION: Bos taurus Beta-lactoglobulin precursor epitope

<400> SEQUENCE: 388

Ala Ala Ser Asp Ile Ser Leu Leu Asp Ala Gln Ser Ala Pro Leu Arg
1               5                   10                  15

<210> SEQ ID NO 389
<211> LENGTH: 8
<212> TYPE: PRT
<213> ORGANISM: Artificial Sequence
<220> FEATURE:
<223> OTHER INFORMATION: Fagopyrum esculentum BW 16kDa allergen epitope
```

```
<400> SEQUENCE: 389

Glu Gly Val Arg Asp Leu Lys Glu
1               5

<210> SEQ ID NO 390
<211> LENGTH: 17
<212> TYPE: PRT
<213> ORGANISM: Artificial Sequence
<220> FEATURE:
<223> OTHER INFORMATION: Betula pendula Chain A, Birch Pollen Profilin
      epitope

<400> SEQUENCE: 390

Ala Gln Ser Ser Ser Phe Pro Gln Phe Lys Pro Gln Glu Ile Thr Gly
1               5                   10                  15

Ile

<210> SEQ ID NO 391
<211> LENGTH: 20
<212> TYPE: PRT
<213> ORGANISM: Artificial Sequence
<220> FEATURE:
<223> OTHER INFORMATION: Oncorhynchus mykiss collagen a2(I) epitope

<400> SEQUENCE: 391

Met Lys Gly Leu Arg Gly His Gly Gly Leu Gln Gly Met Pro Gly Pro
1               5                   10                  15

Asn Gly Pro Ser
            20

<210> SEQ ID NO 392
<211> LENGTH: 46
<212> TYPE: PRT
<213> ORGANISM: Artificial Sequence
<220> FEATURE:
<223> OTHER INFORMATION: Bos taurus collagen, type I, alpha 2 epitope

<400> SEQUENCE: 392

Ala Pro Gly Pro Asp Gly Asn Asn Gly Ala Gln Gly Pro Pro Gly Leu
1               5                   10                  15

Gln Gly Val Gln Gly Gly Lys Gly Glu Gln Gly Pro Ala Gly Pro Pro
                20                  25                  30

Gly Phe Gln Gly Leu Pro Gly Pro Ala Gly Thr Ala Gly Glu
        35                  40                  45

<210> SEQ ID NO 393
<211> LENGTH: 15
<212> TYPE: PRT
<213> ORGANISM: Artificial Sequence
<220> FEATURE:
<223> OTHER INFORMATION: Arachis hypogaea Conglutin-7 precursor epitope

<400> SEQUENCE: 393

Ala Ala His Ala Ser Ala Arg Gln Gln Trp Glu Leu Gln Gly Asp
1               5                   10                  15

<210> SEQ ID NO 394
<211> LENGTH: 8
<212> TYPE: PRT
<213> ORGANISM: Artificial Sequence
<220> FEATURE:
<223> OTHER INFORMATION: Periplaneta americana Cr-PII allergen epitope

<400> SEQUENCE: 394
```

```
Ile Arg Ser Trp Phe Gly Leu Pro
1               5
```

<210> SEQ ID NO 395
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 395

```
Glu Asn Pro Lys Lys Tyr Ile Pro Gly Thr Lys
1               5                   10
```

<210> SEQ ID NO 396
<211> LENGTH: 10
<212> TYPE: PRT
<213> ORGANISM: Artificial Sequence
<220> FEATURE:
<223> OTHER INFORMATION: Rattus norvegicus Cytochrome P450 3A1 epitope

<400> SEQUENCE: 396

```
Asp Met Val Leu Asn Glu Thr Leu Arg Leu
1               5                   10
```

<210> SEQ ID NO 397
<211> LENGTH: 9
<212> TYPE: PRT
<213> ORGANISM: Artificial Sequence
<220> FEATURE:
<223> OTHER INFORMATION: Dermatophagoides farinae Der f 2 epitope

<400> SEQUENCE: 397

```
Ile Ala Thr His Ala Lys Ile Arg Asp
1               5
```

<210> SEQ ID NO 398
<211> LENGTH: 15
<212> TYPE: PRT
<213> ORGANISM: Artificial Sequence
<220> FEATURE:
<223> OTHER INFORMATION: Dermatophagoides farinae Der f 7 allergen
      epitope

<400> SEQUENCE: 398

```
His Ile Gly Gly Leu Ser Ile Leu Asp Pro Ile Phe Gly Val Leu
1               5                   10                  15
```

<210> SEQ ID NO 399
<211> LENGTH: 43
<212> TYPE: PRT
<213> ORGANISM: Artificial Sequence
<220> FEATURE:
<223> OTHER INFORMATION: Dermatophagoides pteronyssinus Der p 1
      allergen epitope

<400> SEQUENCE: 399

```
Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Ala Asn Lys Ile Arg Glu
            20                  25                  30

Ala Leu Ala Gln Thr His Ser Ala Ile Ala Val
            35                  40
```

<210> SEQ ID NO 400
<211> LENGTH: 15

```
<212> TYPE: PRT
<213> ORGANISM: Artificial Sequence
<220> FEATURE:
<223> OTHER INFORMATION: Dermatophagoides pteronyssinus Der p 7
      allergen polypeptide epitope

<400> SEQUENCE: 400

His Ile Gly Gly Leu Ser Ile Leu Asp Pro Ile Phe Ala Val Leu
1               5                   10                  15

<210> SEQ ID NO 401
<211> LENGTH: 39
<212> TYPE: PRT
<213> ORGANISM: Artificial Sequence
<220> FEATURE:
<223> OTHER INFORMATION: Candida albicans Enolase 1 (2-phosphoglycerate
      dehydratase) (2-phospho-D-glycerate hydro-lyase) epitope

<400> SEQUENCE: 401

Gln Ala Ala Asn Asp Ser Tyr Ala Ala Gly Trp Gly Val Met Val Ser
1               5                   10                  15

His Arg Ser Gly Glu Thr Glu Asp Thr Phe Ile Ala Asp Leu Ser Val
            20                  25                  30

Gly Leu Arg Ser Gly Gln Ile
        35

<210> SEQ ID NO 402
<211> LENGTH: 21
<212> TYPE: PRT
<213> ORGANISM: Artificial Sequence
<220> FEATURE:
<223> OTHER INFORMATION: Hevea brasiliensis ENSP-like protein epitope

<400> SEQUENCE: 402

Phe Pro Leu Ile Thr Cys Cys Gly Tyr Gly Gly Lys Tyr Asn Phe Ser
1               5                   10                  15

Val Thr Ala Pro Cys
            20

<210> SEQ ID NO 403
<211> LENGTH: 12
<212> TYPE: PRT
<213> ORGANISM: Artificial Sequence
<220> FEATURE:
<223> OTHER INFORMATION: Fagopyrum esculentum Fag e 1 epitope

<400> SEQUENCE: 403

Ala Val Val Leu Lys Ala Gly Asn Glu Gly Leu Glu
1               5                   10

<210> SEQ ID NO 404
<211> LENGTH: 10
<212> TYPE: PRT
<213> ORGANISM: Artificial Sequence
<220> FEATURE:
<223> OTHER INFORMATION: Triticum aestivum Gamma-gliadin precursor
      epitope

<400> SEQUENCE: 404

Leu Gln Pro Gln Gln Pro Phe Pro Gln Gln
1               5                   10

<210> SEQ ID NO 405
<211> LENGTH: 21
<212> TYPE: PRT
<213> ORGANISM: Artificial Sequence
```

```
<220> FEATURE:
<223> OTHER INFORMATION: Chironomus thummi thummi Globin CTT-III epitope

<400> SEQUENCE: 405

Ala His Thr Asp Phe Ala Gly Ala Glu Ala Ala Trp Gly Ala Thr Leu
1               5                   10                  15

Asp Thr Phe Phe Gly
            20

<210> SEQ ID NO 406
<211> LENGTH: 11
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 406

Gly Val Thr His Asp Gln Leu Asn Asn Phe Arg
1               5                   10

<210> SEQ ID NO 407
<211> LENGTH: 23
<212> TYPE: PRT
<213> ORGANISM: Artificial Sequence
<220> FEATURE:
<223> OTHER INFORMATION: Chironomus thummi thummi Globin CTT-IV
      precursor epitope

<400> SEQUENCE: 407

Lys Ala His Thr Asp Phe Ala Gly Ala Glu Ala Ala Trp Gly Ala Thr
1               5                   10                  15

Leu Asp Ala Phe Phe Gly Met
            20

<210> SEQ ID NO 408
<211> LENGTH: 35
<212> TYPE: PRT
<213> ORGANISM: Artificial Sequence
<220> FEATURE:
<223> OTHER INFORMATION: Chironomus thummi thummi Globin CTT-VI
      precursor epitope

<400> SEQUENCE: 408

Ile Val Ser Phe Leu Ser Glu Val Ile Ser Leu Ala Gly Ser Asp Ala
1               5                   10                  15

Asn Ile Pro Ala Ile Gln Asn Leu Ala Lys Glu Leu Ala Thr Ser His
            20                  25                  30

Lys Pro Arg
        35

<210> SEQ ID NO 409
<211> LENGTH: 35
<212> TYPE: PRT
<213> ORGANISM: Artificial Sequence
<220> FEATURE:
<223> OTHER INFORMATION: Chironomus thummi thummi Globin CTT-VIII
      epitope

<400> SEQUENCE: 409

Ile Val Gly Phe Phe Ser Glu Val Ile Gly Leu Ile Gly Asn Pro Glu
1               5                   10                  15

Asn Arg Pro Ala Leu Lys Thr Leu Ile Asp Gly Leu Ala Ser Ser His
            20                  25                  30
```

Lys Ala Arg
        35

<210> SEQ ID NO 410
<211> LENGTH: 9
<212> TYPE: PRT
<213> ORGANISM: Artificial Sequence
<220> FEATURE:
<223> OTHER INFORMATION: Hevea brasiliensis Glucan endo-1,3-beta-
      glucosidase, basic vacuolar isoform epitope

<400> SEQUENCE: 410

Ala Trp Leu Ala Gln Phe Val Leu Pro
1               5

<210> SEQ ID NO 411
<211> LENGTH: 14
<212> TYPE: PRT
<213> ORGANISM: Artificial Sequence
<220> FEATURE:
<223> OTHER INFORMATION: Triticum aestivum Glutenin, high molecular
      weight subunit DX5 epitope

<400> SEQUENCE: 411

Ala Gln Gly Gln Gln Pro Gly Gln Gly Gln Gln Gly Gln Gln
1               5                   10

<210> SEQ ID NO 412
<211> LENGTH: 5
<212> TYPE: PRT
<213> ORGANISM: Artificial Sequence
<220> FEATURE:
<223> OTHER INFORMATION: Triticum aestivum Glutenin, high molecular
      weight subunit DX5 precursor epitope

<400> SEQUENCE: 412

Gln Gln Pro Gly Gln
1               5

<210> SEQ ID NO 413
<211> LENGTH: 5
<212> TYPE: PRT
<213> ORGANISM: Artificial Sequence
<220> FEATURE:
<223> OTHER INFORMATION: Triticum aestivum Glutenin, low molecular
      weight subunit precursor epitope

<400> SEQUENCE: 413

Gln Gln Gln Pro Pro
1               5

<210> SEQ ID NO 414
<211> LENGTH: 15
<212> TYPE: PRT
<213> ORGANISM: Artificial Sequence
<220> FEATURE:
<223> OTHER INFORMATION: Phaseolus vulgaris Glycine-rich cell wall
      structural protein 1.8 precursor epitope

<400> SEQUENCE: 414

Gly Gly Tyr Gly Asp Gly Gly Ala His Gly Gly Tyr Gly Gly
1               5                   10                  15

<210> SEQ ID NO 415
<211> LENGTH: 15
<212> TYPE: PRT
<213> ORGANISM: Artificial Sequence
<220> FEATURE:

<223> OTHER INFORMATION: Arachis hypogaea Glycinin epitope

<400> SEQUENCE: 415

Ala Leu Ser Arg Leu Val Leu Arg Arg Asn Ala Leu Arg Arg Pro
1               5                   10                  15

<210> SEQ ID NO 416
<211> LENGTH: 13
<212> TYPE: PRT
<213> ORGANISM: Artificial Sequence
<220> FEATURE:
<223> OTHER INFORMATION: Glycine max Glycinin G1 precursor epitope

<400> SEQUENCE: 416

Gly Ala Ile Val Thr Val Lys Gly Gly Leu Ser Val Ile
1               5                   10

<210> SEQ ID NO 417
<211> LENGTH: 15
<212> TYPE: PRT
<213> ORGANISM: Artificial Sequence
<220> FEATURE:
<223> OTHER INFORMATION: Glycine max Glycinin G2 precursor epitope

<400> SEQUENCE: 417

Ala Leu Ser Arg Cys Thr Leu Asn Arg Asn Ala Leu Arg Arg Pro
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: Holcus lanatus group V allergen epitope

<400> SEQUENCE: 418

Ala Asn Val Pro Pro Ala Asp Lys Tyr Lys Thr Phe Glu Ala Ala
1               5                   10                  15

<210> SEQ ID NO 419
<211> LENGTH: 12
<212> TYPE: PRT
<213> ORGANISM: Artificial Sequence
<220> FEATURE:
<223> OTHER INFORMATION: Oryza sativa Japonica Group hypothetical
      protein epitope

<400> SEQUENCE: 419

Ala Phe Asn His Phe Gly Ile Gln Leu Val Gln Arg
1               5                   10

<210> SEQ ID NO 420
<211> LENGTH: 14
<212> TYPE: PRT
<213> ORGANISM: Artificial Sequence
<220> FEATURE:
<223> OTHER INFORMATION: Bos taurus Kappa-casein precursor epitope

<400> SEQUENCE: 420

Ala Lys Tyr Ile Pro Ile Gln Tyr Val Leu Ser Arg Tyr Pro
1               5                   10

<210> SEQ ID NO 421
<211> LENGTH: 20
<212> TYPE: PRT
<213> ORGANISM: Artificial Sequence
<220> FEATURE:

<223> OTHER INFORMATION: Alternaria alternata Major allergen Alt a 1
      precursor epitope

<400> SEQUENCE: 421

Ala Asp Pro Val Thr Thr Glu Gly Asp Tyr Val Val Lys Ile Ser Glu
1               5                   10                  15

Phe Tyr Gly Arg
            20

<210> SEQ ID NO 422
<211> LENGTH: 15
<212> TYPE: PRT
<213> ORGANISM: Artificial Sequence
<220> FEATURE:
<223> OTHER INFORMATION: Anisakis simplex Major allergen Ani s 1 epitope

<400> SEQUENCE: 422

Cys Lys Met Pro Asp Arg Gly Ala Cys Ala Leu Gly Lys Lys Pro
1               5                   10                  15

<210> SEQ ID NO 423
<211> LENGTH: 13
<212> TYPE: PRT
<213> ORGANISM: Artificial Sequence
<220> FEATURE:
<223> OTHER INFORMATION: Aspergillus fumigatus Major allergen Asp f 1
      epitope

<400> SEQUENCE: 423

Leu Asn Pro Lys Thr Asn Lys Trp Glu Asp Lys Arg Tyr
1               5                   10

<210> SEQ ID NO 424
<211> LENGTH: 10
<212> TYPE: PRT
<213> ORGANISM: Artificial Sequence
<220> FEATURE:
<223> OTHER INFORMATION: Aspergillus fumigatus Major allergen Asp f 2
      epitope

<400> SEQUENCE: 424

Ala His Ile Leu Arg Trp Gly Asn Glu Ser
1               5                   10

<210> SEQ ID NO 425
<211> LENGTH: 20
<212> TYPE: PRT
<213> ORGANISM: Artificial Sequence
<220> FEATURE:
<223> OTHER INFORMATION: Bos taurus major allergen beta-lactoglobulin
      epitope

<400> SEQUENCE: 425

Leu Gln Lys Trp Glu Asn Asp Glu Cys Ala Gln Lys Lys Ile Ile Ala
1               5                   10                  15

Glu Lys Thr Lys
            20

<210> SEQ ID NO 426
<211> LENGTH: 14
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 426

Asp Ala Lys Met Thr Glu Glu Asp Lys Glu Asn Ala Leu Ser
1               5                   10

<210> SEQ ID NO 427
<211> LENGTH: 14
<212> TYPE: PRT
<213> ORGANISM: Artificial Sequence
<220> FEATURE:
<223> OTHER INFORMATION: Felis catus Major allergen I polypeptide chain
      2 precursor epitope

<400> SEQUENCE: 427

Glu Pro Glu Arg Thr Ala Met Lys Lys Ile Gln Asp Cys Tyr
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Felis catus major allergen I, polypeptide
      chain 1 epitope

<400> SEQUENCE: 428

Leu Leu Asp Lys Ile Tyr Thr Ser Pro Leu Cys
1               5                   10

<210> SEQ ID NO 429
<211> LENGTH: 29
<212> TYPE: PRT
<213> ORGANISM: Artificial Sequence
<220> FEATURE:
<223> OTHER INFORMATION: Turbo cornutus major allergen Tur c1 - Turbo
      cornutus epitope

<400> SEQUENCE: 429

Leu Glu Asp Glu Leu Leu Ala Glu Lys Glu Lys Tyr Lys Ala Ile Ser
1               5                   10                  15

Asp Glu Leu Asp Gln Thr Phe Ala Glu Leu Ala Gly Tyr
            20                  25

<210> SEQ ID NO 430
<211> LENGTH: 25
<212> TYPE: PRT
<213> ORGANISM: Artificial Sequence
<220> FEATURE:
<223> OTHER INFORMATION: Dermatophagoides pteronyssinus major house
      dust allergen epitope

<400> SEQUENCE: 430

Leu Ala His Arg Asn Gln Ser Leu Asp Leu Ala Glu Gln Glu Leu Val
1               5                   10                  15

Asp Cys Ala Ser Gln His Gly Cys His
            20                  25

<210> SEQ ID NO 431
<211> LENGTH: 9
<212> TYPE: PRT
<213> ORGANISM: Artificial Sequence
<220> FEATURE:
<223> OTHER INFORMATION: Hevea brasiliensis Major latex allergen Hev b
      5 epitope

<400> SEQUENCE: 431

Ala Pro Pro Ala Ser Glu Gln Glu Thr
1               5

<210> SEQ ID NO 432
<211> LENGTH: 43
<212> TYPE: PRT
<213> ORGANISM: Artificial Sequence
<220> FEATURE:
<223> OTHER INFORMATION: Dermatophagoides pteronyssinus Major mite
      fecal allergen Der p 1 epitope

<400> SEQUENCE: 432

Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Ala Asn Lys Ile Arg Glu
            20                  25                  30

Ala Leu Ala Gln Pro Gln Arg Tyr Cys Arg His
        35                  40

<210> SEQ ID NO 433
<211> LENGTH: 12
<212> TYPE: PRT
<213> ORGANISM: Artificial Sequence
<220> FEATURE:
<223> OTHER INFORMATION: Olea europaea Major pollen allergen epitope

<400> SEQUENCE: 433

Phe Thr Glu Val Gly Tyr Thr Arg Ala Glu Gly Leu
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 434

Asp Gly Asp Asn Leu Phe Pro Lys Val Ala
1               5                   10

<210> SEQ ID NO 435
<211> LENGTH: 11
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 435

Trp Arg Ser Thr Gln Asp Ser Phe Asn Asn Gly
1               5                   10

<210> SEQ ID NO 436
<211> LENGTH: 17
<212> TYPE: PRT
<213> ORGANISM: Artificial Sequence
<220> FEATURE:
<223> OTHER INFORMATION: Corylus avellana Major pollen allergen Cor a 1
      epitope

<400> SEQUENCE: 436

Tyr Val Leu Asp Gly Asp Lys Leu Leu Pro Lys Val Ala Pro Gln Ala
1               5                   10                  15

Leu

```
<210> SEQ ID NO 437
<211> LENGTH: 27
<212> TYPE: PRT
<213> ORGANISM: Artificial Sequence
<220> FEATURE:
<223> OTHER INFORMATION: Holcus lanatus Major pollen allergen Hol l 1
      precursor epitope

<400> SEQUENCE: 437

Ala Lys Ser Thr Trp Tyr Gly Lys Pro Thr Gly Ala Gly Pro Lys Asp
1               5                   10                  15

Asn Gly Gly Ala Cys Gly Tyr Lys Asp Val Asp
            20                  25

<210> SEQ ID NO 438
<211> LENGTH: 12
<212> TYPE: PRT
<213> ORGANISM: Artificial Sequence
<220> FEATURE:
<223> OTHER INFORMATION: Juniperus ashei Major pollen allergen Jun a 1
      precursor epitope

<400> SEQUENCE: 438

Ala Phe Asn Gln Phe Gly Pro Asn Ala Gly Gln Arg
1               5                   10

<210> SEQ ID NO 439
<211> LENGTH: 34
<212> TYPE: PRT
<213> ORGANISM: Artificial Sequence
<220> FEATURE:
<223> OTHER INFORMATION: Olea europaea major pollen allergen Ole e 1
      epitope

<400> SEQUENCE: 439

Ser Gly Arg Lys Asp Cys Asn Glu Ile Pro Thr Glu Gly Trp Val Lys
1               5                   10                  15

Pro Ser Leu Lys Phe Ile Leu Asn Thr Val Asn Gly Thr Thr Arg Thr
            20                  25                  30

Val Asn

<210> SEQ ID NO 440
<211> LENGTH: 9
<212> TYPE: PRT
<213> ORGANISM: Artificial Sequence
<220> FEATURE:
<223> OTHER INFORMATION: Malus x domestica mal d 3 epitope

<400> SEQUENCE: 440

Arg Thr Thr Ala Asp Arg Gln Thr Ala
1               5

<210> SEQ ID NO 441
<211> LENGTH: 16
<212> TYPE: PRT
<213> ORGANISM: Artificial Sequence
<220> FEATURE:
<223> OTHER INFORMATION: Blomia tropicalis Mite allergen Blo t 5 epitope

<400> SEQUENCE: 441

Glu Glu Ala Gln Thr Leu Ser Lys Ile Leu Leu Lys Asp Leu Lys Glu
1               5                   10                  15

<210> SEQ ID NO 442
<211> LENGTH: 5
<212> TYPE: PRT
```

```
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 442

Asp Pro Cys Ile Ile
1               5

<210> SEQ ID NO 443
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 443

Asp Gln Val Asp Val Lys Asp Cys Ala Asn His Glu Ile Lys Lys
1               5                   10                  15

<210> SEQ ID NO 444
<211> LENGTH: 33
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 444

Ala Ala Asn Gln Asp Thr Ala Lys Val Thr Ile Lys Val Leu Ala Lys
1               5                   10                  15

Val Ala Gly Thr Thr Ile Gln Val Pro Gly Leu Glu Thr Asp Gly Cys
            20                  25                  30

Lys

<210> SEQ ID NO 445
<211> LENGTH: 6
<212> TYPE: PRT
<213> ORGANISM: Artificial Sequence
<220> FEATURE:
<223> OTHER INFORMATION: Triticum aestivum monomeric alpha-amylase
      inhibitor epitope

<400> SEQUENCE: 445

Ala Ala Ser Val Pro Glu
1               5

<210> SEQ ID NO 446
<211> LENGTH: 9
<212> TYPE: PRT
<213> ORGANISM: Artificial Sequence
<220> FEATURE:
<223> OTHER INFORMATION: Prunus armeniaca Non-specific lipid-transfer
      protein 1 epitope

<400> SEQUENCE: 446

Val Asn Pro Asn Asn Ala Ala Ala Leu
1               5

<210> SEQ ID NO 447
<211> LENGTH: 15
<212> TYPE: PRT
<213> ORGANISM: Artificial Sequence
<220> FEATURE:
<223> OTHER INFORMATION: Prunus armeniaca Non-specific lipid-transfer
      protein 1 (LTP 1) (Major allergen Pru ar 3) epitope
```

```
<400> SEQUENCE: 447

Leu Ala Arg Thr Thr Pro Asp Arg Arg Thr Ala Cys Asn Cys Leu
1               5                   10                  15

<210> SEQ ID NO 448
<211> LENGTH: 18
<212> TYPE: PRT
<213> ORGANISM: Artificial Sequence
<220> FEATURE:
<223> OTHER INFORMATION: Prunus domestica Non-specific lipid-transfer
      protein 1 (LTP 1) (Major allergen Pru d 3) epitope

<400> SEQUENCE: 448

Leu Ala Arg Thr Thr Ala Asp Arg Arg Ala Ala Cys Asn Cys Leu Lys
1               5                   10                  15

Gln Leu

<210> SEQ ID NO 449
<211> LENGTH: 15
<212> TYPE: PRT
<213> ORGANISM: Artificial Sequence
<220> FEATURE:
<223> OTHER INFORMATION: Malus x domestica Non-specific lipid-transfer
      protein precursor (LTP) (Allergen Mal d 3) epitope

<400> SEQUENCE: 449

Ala Asp Arg Gln Thr Ala Cys Asn Cys Leu Lys Asn Leu Ala Gly
1               5                   10                  15

<210> SEQ ID NO 450
<211> LENGTH: 12
<212> TYPE: PRT
<213> ORGANISM: Artificial Sequence
<220> FEATURE:
<223> OTHER INFORMATION: Olea europaea Ole e 1 protein epitope

<400> SEQUENCE: 450

Glu Asp Val Pro Gln Pro Pro Val Ser Gln Phe His
1               5                   10

<210> SEQ ID NO 451
<211> LENGTH: 25
<212> TYPE: PRT
<213> ORGANISM: Artificial Sequence
<220> FEATURE:
<223> OTHER INFORMATION: Olea europaea Ole e 1.0102 protein epitope

<400> SEQUENCE: 451

Glu Asp Val Pro Gln Pro Pro Val Ser Gln Phe His Ile Gln Gly Gln
1               5                   10                  15

Val Tyr Cys Asp Thr Cys Arg Ala Gly
            20                  25

<210> SEQ ID NO 452
<211> LENGTH: 10
<212> TYPE: PRT
<213> ORGANISM: Artificial Sequence
<220> FEATURE:
<223> OTHER INFORMATION: Triticum aestivum Omega gliadin storage
      protein epitope

<400> SEQUENCE: 452

Gln Gln Pro Gln Gln Ser Phe Pro Gln Gln
1               5                   10
```

```
<210> SEQ ID NO 453
<211> LENGTH: 7
<212> TYPE: PRT
<213> ORGANISM: Artificial Sequence
<220> FEATURE:
<223> OTHER INFORMATION: Triticum aestivum omega-5 gliadin epitope

<400> SEQUENCE: 453

Gln Gln Phe His Gln Gln Gln
1               5

<210> SEQ ID NO 454
<211> LENGTH: 35
<212> TYPE: PRT
<213> ORGANISM: Artificial Sequence
<220> FEATURE:
<223> OTHER INFORMATION: Aspergillus fumigatus Oryzin precursor epitope

<400> SEQUENCE: 454

Ala Ser Asn Thr Ser Pro Ala Ser Ala Pro Asn Ala Leu Thr Val Ala
1               5                   10                  15

Ala Ile Asn Lys Ser Asn Ala Arg Ala Ser Phe Ser Asn Tyr Gly Ser
            20                  25                  30

Val Val Asp
        35

<210> SEQ ID NO 455
<211> LENGTH: 9
<212> TYPE: PRT
<213> ORGANISM: Artificial Sequence
<220> FEATURE:
<223> OTHER INFORMATION: Gallus gallus Ovalbumin epitope

<400> SEQUENCE: 455

Cys Phe Asp Val Phe Lys Glu Leu Lys
1               5

<210> SEQ ID NO 456
<211> LENGTH: 10
<212> TYPE: PRT
<213> ORGANISM: Artificial Sequence
<220> FEATURE:
<223> OTHER INFORMATION: Gallus gallus Ovomucoid epitope

<400> SEQUENCE: 456

Cys Asn Phe Cys Asn Ala Val Val Glu Ser
1               5                   10

<210> SEQ ID NO 457
<211> LENGTH: 14
<212> TYPE: PRT
<213> ORGANISM: Artificial Sequence
<220> FEATURE:
<223> OTHER INFORMATION: Gallus gallus Ovomucoid precursor epitope

<400> SEQUENCE: 457

Ala Glu Val Asp Cys Ser Arg Phe Pro Asn Ala Thr Asp Lys
1               5                   10

<210> SEQ ID NO 458
<211> LENGTH: 10
<212> TYPE: PRT
<213> ORGANISM: Artificial Sequence
<220> FEATURE:
<223> OTHER INFORMATION: Glycine max P34 probable thiol protease
      precursor epitope
```

-continued

<400> SEQUENCE: 458

Ala Ser Trp Asp Trp Arg Lys Lys Gly Val
1               5                   10

<210> SEQ ID NO 459
<211> LENGTH: 10
<212> TYPE: PRT
<213> ORGANISM: Artificial Sequence
<220> FEATURE:
<223> OTHER INFORMATION: Glycine max P34 probable thiol protease
      precursor; Gly m 1 epitope

<400> SEQUENCE: 459

Pro Gln Glu Phe Ser Lys Lys Thr Tyr Gln
1               5                   10

<210> SEQ ID NO 460
<211> LENGTH: 9
<212> TYPE: PRT
<213> ORGANISM: Artificial Sequence
<220> FEATURE:
<223> OTHER INFORMATION: Parietaria judaica Par j epitope

<400> SEQUENCE: 460

Gly Thr Ser Ser Cys Arg Leu Val Pro
1               5

<210> SEQ ID NO 461
<211> LENGTH: 47
<212> TYPE: PRT
<213> ORGANISM: Artificial Sequence
<220> FEATURE:
<223> OTHER INFORMATION: Blomia tropicalis Paramyosin epitope

<400> SEQUENCE: 461

Glu Lys Leu Arg Asp Gln Lys Glu Ala Leu Ala Arg Glu Asn Lys Lys
1               5                   10                  15

Leu Ala Asp Asp Leu Ala Glu Ala Lys Ser Gln Leu Asn Asp Ala His
            20                  25                  30

Arg Arg Ile His Glu Gln Glu Ile Glu Ile Lys Arg Leu Glu Asn
        35                  40                  45

<210> SEQ ID NO 462
<211> LENGTH: 8
<212> TYPE: PRT
<213> ORGANISM: Artificial Sequence
<220> FEATURE:
<223> OTHER INFORMATION: Gadus morhua callarias Parvalbumin beta epitope

<400> SEQUENCE: 462

Ala Ala Glu Ala Ala Cys Phe Lys
1               5

<210> SEQ ID NO 463
<211> LENGTH: 15
<212> TYPE: PRT
<213> ORGANISM: Artificial Sequence
<220> FEATURE:
<223> OTHER INFORMATION: Salmo salar parvalbumin like 1 epitope

<400> SEQUENCE: 463

Ala Asp Ile Lys Thr Ala Leu Glu Ala Arg Lys Ala Ala Asp Thr
1               5                   10                  15

```
<210> SEQ ID NO 464
<211> LENGTH: 12
<212> TYPE: PRT
<213> ORGANISM: Artificial Sequence
<220> FEATURE:
<223> OTHER INFORMATION: Juniperus ashei Pathogenesis-related protein
      precursor epitope

<400> SEQUENCE: 464

Ala Asp Ile Asn Ala Val Cys Pro Ser Glu Leu Lys
1               5                   10

<210> SEQ ID NO 465
<211> LENGTH: 12
<212> TYPE: PRT
<213> ORGANISM: Artificial Sequence
<220> FEATURE:
<223> OTHER INFORMATION: Nicotiana tabacum Pectate lyase epitope

<400> SEQUENCE: 465

Ala Tyr Asn His Phe Gly Lys Arg Leu Asp Gln Arg
1               5                   10

<210> SEQ ID NO 466
<211> LENGTH: 12
<212> TYPE: PRT
<213> ORGANISM: Artificial Sequence
<220> FEATURE:
<223> OTHER INFORMATION: Musa acuminata AAA Group pectate lyase 2
      epitope

<400> SEQUENCE: 466

Ala Phe Asn His Phe Gly Glu Gly Leu Ile Gln Arg
1               5                   10

<210> SEQ ID NO 467
<211> LENGTH: 15
<212> TYPE: PRT
<213> ORGANISM: Artificial Sequence
<220> FEATURE:
<223> OTHER INFORMATION: Farfantepenaeus aztecus Pen a 1 allergen
      epitope

<400> SEQUENCE: 467

Ala Asn Ile Gln Leu Val Glu Lys Asp Lys Ala Leu Ser Asn Ala
1               5                   10                  15

<210> SEQ ID NO 468
<211> LENGTH: 43
<212> TYPE: PRT
<213> ORGANISM: Artificial Sequence
<220> FEATURE:
<223> OTHER INFORMATION: Dermatophagoides pteronyssinus Peptidase 1
      precursor (Major mite fecal allergen Der p 1) (Allergen Der p I)
      epitope

<400> SEQUENCE: 468

Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Val Asn Lys Ile Arg Glu
            20                  25                  30

Ala Leu Ala Gln Thr His Ser Ala Ile Ala Val
            35                  40

<210> SEQ ID NO 469
<211> LENGTH: 45
<212> TYPE: PRT
```

<213> ORGANISM: Artificial Sequence
<220> FEATURE:
<223> OTHER INFORMATION: Apis mellifera Phospholipase A2 precursor
    epitope

<400> SEQUENCE: 469

Leu Ile Asp Thr Lys Cys Tyr Lys Leu Glu His Pro Val Thr Gly Cys
1               5                   10                  15

Gly Glu Arg Thr Glu Gly Arg Cys Leu His Tyr Thr Val Asp Lys Ser
            20                  25                  30

Lys Pro Lys Val Tyr Gln Trp Phe Asp Leu Arg Lys Tyr
        35                  40                  45

<210> SEQ ID NO 470
<211> LENGTH: 14
<212> TYPE: PRT
<213> ORGANISM: Artificial Sequence
<220> FEATURE:
<223> OTHER INFORMATION: Myrmecia pilosula Pilosulin-1 precursor (Major
    allergen Myr p 1) (Myr p I) epitope

<400> SEQUENCE: 470

Lys Glu Ala Ile Pro Met Ala Val Glu Met Ala Lys Ser Gln
1               5                   10

<210> SEQ ID NO 471
<211> LENGTH: 8
<212> TYPE: PRT
<213> ORGANISM: Artificial Sequence
<220> FEATURE:
<223> OTHER INFORMATION: Betula pendula Polcalcin Bet v 4 epitope

<400> SEQUENCE: 471

Phe Gly Arg Ala Asn Arg Gly Leu
1               5

<210> SEQ ID NO 472
<211> LENGTH: 36
<212> TYPE: PRT
<213> ORGANISM: Artificial Sequence
<220> FEATURE:
<223> OTHER INFORMATION: Phleum pratense Polcalcin Phl p 7
    (Calcium-binding pollen allergen Phl p 7) (P7) epitope

<400> SEQUENCE: 472

Ala Asp Asp Met Glu Arg Ile Phe Lys Arg Phe Asp Thr Asn Gly Asp
1               5                   10                  15

Gly Lys Ile Ser Leu Ser Glu Leu Thr Asp Ala Leu Arg Thr Leu Gly
            20                  25                  30

Ser Thr Ser Ala
        35

<210> SEQ ID NO 473
<211> LENGTH: 25
<212> TYPE: PRT
<213> ORGANISM: Artificial Sequence
<220> FEATURE:
<223> OTHER INFORMATION: Lolium perenne pollen allergen epitope

<400> SEQUENCE: 473

Glu Gly Gly Thr Lys Ser Glu Val Glu Asp Val Ile Pro Glu Gly Trp
1               5                   10                  15

Lys Ala Asp Thr Ser Tyr Ser Ala Lys
            20                  25

-continued

<210> SEQ ID NO 474
<211> LENGTH: 12
<212> TYPE: PRT
<213> ORGANISM: Artificial Sequence
<220> FEATURE:
<223> OTHER INFORMATION: Ambrosia artemisiifolia Pollen allergen Amb a
      1.4 epitope

<400> SEQUENCE: 474

Ala Phe Asn Lys Phe Thr Asp Asn Val Asp Gln Arg
1               5                   10

<210> SEQ ID NO 475
<211> LENGTH: 8
<212> TYPE: PRT
<213> ORGANISM: Artificial Sequence
<220> FEATURE:
<223> OTHER INFORMATION: Ambrosia artemisiifolia Pollen allergen Amb a
      2 precursor epitope

<400> SEQUENCE: 475

Met Pro Arg Cys Arg Phe Gly Phe
1               5

<210> SEQ ID NO 476
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 476

Cys Asp Ile Lys Asp Pro Ile Arg Leu Glu Pro Gly Gly Pro Asp
1               5                   10                  15

<210> SEQ ID NO 477
<211> LENGTH: 31
<212> TYPE: PRT
<213> ORGANISM: Artificial Sequence
<220> FEATURE:
<223> OTHER INFORMATION: Betula pendula pollen allergen Bet v 1 epitope

<400> SEQUENCE: 477

Lys Ala Glu Gln Val Lys Ala Ser Lys Glu Met Gly Glu Thr Leu Leu
1               5                   10                  15

Arg Ala Val Glu Ser Tyr Leu Leu Ala His Ser Asp Ala Tyr Asn
            20                  25                  30

<210> SEQ ID NO 478
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 478

Ala Ala Asn Lys Tyr Lys Thr Phe Val Ala Thr Phe Gly Ala Ala Ser
1               5                   10                  15

Asn Lys Ala Phe
            20

<210> SEQ ID NO 479
<211> LENGTH: 25
<212> TYPE: PRT

-continued

```
<213> ORGANISM: Artificial Sequence
<220> FEATURE:
<223> OTHER INFORMATION: Lolium perenne Pollen allergen Lol p 2-A (Lol
      p II-A) epitope

<400> SEQUENCE: 479

Glu Lys Gly Met Arg Asn Val Phe Asp Asp Val Val Pro Ala Asp Phe
1               5                   10                  15

Lys Val Gly Thr Thr Tyr Lys Pro Glu
            20                  25

<210> SEQ ID NO 480
<211> LENGTH: 27
<212> TYPE: PRT
<213> ORGANISM: Artificial Sequence
<220> FEATURE:
<223> OTHER INFORMATION: Lolium perenne Pollen allergen Lol p 3 (Lol p
      III) epitope

<400> SEQUENCE: 480

Lys Gly Gly Met Lys Asn Val Phe Asp Glu Val Ile Pro Thr Ala Phe
1               5                   10                  15

Thr Val Gly Lys Thr Tyr Thr Pro Glu Tyr Asn
            20                  25

<210> SEQ ID NO 481
<211> LENGTH: 12
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 481

Ala Ala Glu Gly Ala Thr Pro Glu Ala Lys Tyr Asp
1               5                   10

<210> SEQ ID NO 482
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 482

Ala Pro Tyr His Phe Asp Leu Ser Gly His Ala Phe Gly Ala Met
1               5                   10                  15

<210> SEQ ID NO 483
<211> LENGTH: 8
<212> TYPE: PRT
<213> ORGANISM: Artificial Sequence
<220> FEATURE:
<223> OTHER INFORMATION: Zea mays pollen allergen Phl p 11 epitope

<400> SEQUENCE: 483

Arg Asp Arg Ala Arg Val Pro Leu
1               5

<210> SEQ ID NO 484
<211> LENGTH: 12
<212> TYPE: PRT
<213> ORGANISM: Artificial Sequence
<220> FEATURE:
<223> OTHER INFORMATION: Phleum pratense pollen allergen Phl pI epitope
```

-continued

<400> SEQUENCE: 484

Ile Pro Lys Val Pro Pro Gly Pro Asn Ile Thr Ala
1               5                   10

<210> SEQ ID NO 485
<211> LENGTH: 20
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 485

Gly Gln Cys Lys Trp Val Asn Gly Arg Glu Ile Cys Asn Asp Arg Asp
1               5                   10                  15

Arg Pro Thr Ala
            20

<210> SEQ ID NO 486
<211> LENGTH: 30
<212> TYPE: PRT
<213> ORGANISM: Artificial Sequence
<220> FEATURE:
<223> OTHER INFORMATION: Parietaria judaica Probable non-specific
      lipid-transfer protein epitope

<400> SEQUENCE: 486

Gln Glu Thr Cys Gly Thr Met Val Arg Ala Leu Met Pro Cys Leu Pro
1               5                   10                  15

Phe Val Gln Gly Lys Glu Lys Glu Pro Ser Lys Gly Cys Cys
            20                  25                  30

<210> SEQ ID NO 487
<211> LENGTH: 10
<212> TYPE: PRT
<213> ORGANISM: Artificial Sequence
<220> FEATURE:
<223> OTHER INFORMATION: Parietaria judaica Probable non-specific
      lipid-transfer protein 2 epitope

<400> SEQUENCE: 487

Ala Glu Val Pro Lys Lys Cys Asp Ile Lys
1               5                   10

<210> SEQ ID NO 488
<211> LENGTH: 30
<212> TYPE: PRT
<213> ORGANISM: Artificial Sequence
<220> FEATURE:
<223> OTHER INFORMATION: Parietaria judaica Probable non-specific
      lipid-transfer protein 2 precursor epitope

<400> SEQUENCE: 488

Glu Ala Cys Gly Lys Val Val Gln Asp Ile Met Pro Cys Leu His Phe
1               5                   10                  15

Val Lys Gly Glu Glu Lys Glu Pro Ser Lys Glu Cys Cys Ser
            20                  25                  30

<210> SEQ ID NO 489
<211> LENGTH: 12
<212> TYPE: PRT
<213> ORGANISM: Artificial Sequence
<220> FEATURE:
<223> OTHER INFORMATION: Solanum lycopersicum Probable pectate lyase
      P59 epitope

```
<400> SEQUENCE: 489

Ala Phe Asn His Phe Gly Lys Arg Leu Ile Gln Arg
1               5                   10

<210> SEQ ID NO 490
<211> LENGTH: 10
<212> TYPE: PRT
<213> ORGANISM: Artificial Sequence
<220> FEATURE:
<223> OTHER INFORMATION: Cucumis melo profilin epitope

<400> SEQUENCE: 490

Ala Phe Arg Leu Glu Glu Ile Ala Ala Ile
1               5                   10

<210> SEQ ID NO 491
<211> LENGTH: 56
<212> TYPE: PRT
<213> ORGANISM: Artificial Sequence
<220> FEATURE:
<223> OTHER INFORMATION: Glycine max Profilin-1 epitope

<400> SEQUENCE: 491

Trp Ala Gln Ser Thr Asp Phe Pro Gln Phe Lys Pro Glu Glu Ile Thr
1               5                   10                  15

Ala Ile Met Asn Asp Phe Asn Glu Pro Gly Ser Leu Ala Pro Thr Gly
            20                  25                  30

Leu Tyr Leu Gly Gly Thr Lys Tyr Met Val Ile Gln Gly Glu Pro Gly
        35                  40                  45

Ala Val Ile Arg Gly Lys Lys Gly
    50                  55

<210> SEQ ID NO 492
<211> LENGTH: 43
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 492

Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp
        35                  40

<210> SEQ ID NO 493
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 493

Gly Lys Cys Gly Val Ser Ile Pro Tyr Lys
1               5                   10

<210> SEQ ID NO 494
<211> LENGTH: 15
<212> TYPE: PRT
<213> ORGANISM: Artificial Sequence
<220> FEATURE:
<223> OTHER INFORMATION: Prunus dulcis prunin 1 precursor epitope
```

<400> SEQUENCE: 494

Glu Glu Ser Gln Gln Ser Ser Gln Gln Gly Arg Gln Gln Glu Gln
1               5                   10                  15

<210> SEQ ID NO 495
<211> LENGTH: 15
<212> TYPE: PRT
<213> ORGANISM: Artificial Sequence
<220> FEATURE:
<223> OTHER INFORMATION: Prunus dulcis prunin 2 precursor epitope

<400> SEQUENCE: 495

Asp Ser Gln Pro Gln Gln Phe Gln Gln Gln Gln Gln Gln Gln Gln
1               5                   10                  15

<210> SEQ ID NO 496
<211> LENGTH: 11
<212> TYPE: PRT
<213> ORGANISM: Artificial Sequence
<220> FEATURE:
<223> OTHER INFORMATION: Hesperocyparis arizonica putative allergen Cup
      a 1 epitope

<400> SEQUENCE: 496

Trp Arg Phe Thr Arg Asp Ala Phe Thr Asn Gly
1               5                   10

<210> SEQ ID NO 497
<211> LENGTH: 10
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 497

Phe Pro Thr Phe Pro Asp Gly His Asp Tyr
1               5                   10

<210> SEQ ID NO 498
<211> LENGTH: 12
<212> TYPE: PRT
<213> ORGANISM: Artificial Sequence
<220> FEATURE:
<223> OTHER INFORMATION: Mangifera indica ripening-related pectate
      lyase epitope

<400> SEQUENCE: 498

Ala Tyr Asn His Phe Gly Glu Gly Leu Ile Gln Arg
1               5                   10

<210> SEQ ID NO 499
<211> LENGTH: 10
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 499

Ala Glu Asp Glu Asp Asn Gln Gln Gly Gln
1               5                   10

<210> SEQ ID NO 500
<211> LENGTH: 15
<212> TYPE: PRT

```
<213> ORGANISM: Artificial Sequence
<220> FEATURE:
<223> OTHER INFORMATION: Juglans regia seed storage protein epitope

<400> SEQUENCE: 500

Asp Asp Asn Gly Leu Glu Glu Thr Ile Cys Thr Leu Arg Leu Arg
1               5                   10                  15

<210> SEQ ID NO 501
<211> LENGTH: 15
<212> TYPE: PRT
<213> ORGANISM: Artificial Sequence
<220> FEATURE:
<223> OTHER INFORMATION: Arachis hypogaea seed storage protein SSP2
      epitope

<400> SEQUENCE: 501

Cys Gly Leu Arg Ala Pro Gln Arg Cys Asp Leu Asp Val Glu Ser
1               5                   10                  15

<210> SEQ ID NO 502
<211> LENGTH: 8
<212> TYPE: PRT
<213> ORGANISM: Artificial Sequence
<220> FEATURE:
<223> OTHER INFORMATION: Gallus gallus serine (or cysteine) proteinase
      inhibitor, clade B (ovalbumin), member 3 epitope

<400> SEQUENCE: 502

Arg Pro Asn Ala Thr Tyr Ser Leu
1               5

<210> SEQ ID NO 503
<211> LENGTH: 8
<212> TYPE: PRT
<213> ORGANISM: Artificial Sequence
<220> FEATURE:
<223> OTHER INFORMATION: Gallus gallus Serum albumin epitope

<400> SEQUENCE: 503

Gln Ser Arg Ala Thr Leu Gly Ile
1               5

<210> SEQ ID NO 504
<211> LENGTH: 17
<212> TYPE: PRT
<213> ORGANISM: Artificial Sequence
<220> FEATURE:
<223> OTHER INFORMATION: Bos taurus Serum albumin precursor epitope

<400> SEQUENCE: 504

Asp Asp Ser Pro Asp Leu Pro Lys Leu Lys Pro Asp Pro Asn Thr Leu
1               5                   10                  15

Cys

<210> SEQ ID NO 505
<211> LENGTH: 10
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 505

Ala Glu Glu Val Glu Glu Glu Arg Leu Lys
1               5                   10
```

```
<210> SEQ ID NO 506
<211> LENGTH: 12
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 506

Asp Ala Leu Thr Leu Arg Thr Ala Thr Asn Ile Trp
1               5                   10

<210> SEQ ID NO 507
<211> LENGTH: 48
<212> TYPE: PRT
<213> ORGANISM: Artificial Sequence
<220> FEATURE:
<223> OTHER INFORMATION: Aspergillus fumigatus Superoxide dismutase
      epitope

<400> SEQUENCE: 507

Tyr Thr Leu Pro Pro Leu Pro Tyr Pro Tyr Asp Ala Leu Gln Pro Tyr
1               5                   10                  15

Ile Ser Gln Gln Ile Met Glu Leu His His Lys Lys His His Gln Thr
            20                  25                  30

Tyr Val Asn Gly Leu Asn Ala Ala Leu Glu Ala Gln Lys Lys Ala Ala
        35                  40                  45

<210> SEQ ID NO 508
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 508

Asp Cys Asn Gly His Gly Thr His Val Ala Gly Thr Val Gly Gly Thr
1               5                   10                  15

Lys Tyr Gly Leu
            20

<210> SEQ ID NO 509
<211> LENGTH: 10
<212> TYPE: PRT
<213> ORGANISM: Artificial Sequence
<220> FEATURE:
<223> OTHER INFORMATION: Triticum aestivum Triticum aestivum proteins
      epitope

<400> SEQUENCE: 509

Leu Pro Gln Gln Gln Ile Pro Gln Gln Pro
1               5                   10

<210> SEQ ID NO 510
<211> LENGTH: 9
<212> TYPE: PRT
<213> ORGANISM: Artificial Sequence
<220> FEATURE:
<223> OTHER INFORMATION: Penaeus tropomyosin epitope

<400> SEQUENCE: 510

Phe Leu Ala Glu Glu Ala Asp Arg Lys
1               5
```

```
<210> SEQ ID NO 511
<211> LENGTH: 20
<212> TYPE: PRT
<213> ORGANISM: Artificial Sequence
<220> FEATURE:
<223> OTHER INFORMATION: Paralichthys olivaceus type 1 collagen alpha 2
      epitope

<400> SEQUENCE: 511

Met Lys Gly Leu Arg Gly His Pro Gly Leu Gln Gly Met Pro Gly Pro
1               5                   10                  15

Ser Gly Pro Ser
            20

<210> SEQ ID NO 512
<211> LENGTH: 10
<212> TYPE: PRT
<213> ORGANISM: Artificial Sequence
<220> FEATURE:
<223> OTHER INFORMATION: Triticum aestivum type 1 non-specific lipid
      transfer protein precursor epitope

<400> SEQUENCE: 512

Ala Arg Gly Thr Pro Leu Lys Cys Gly Val
1               5                   10

<210> SEQ ID NO 513
<211> LENGTH: 18
<212> TYPE: PRT
<213> ORGANISM: Artificial Sequence
<220> FEATURE:
<223> OTHER INFORMATION: Anisakis simplex UA3-recognized allergen
      epitope

<400> SEQUENCE: 513

Met Cys Gln Cys Val Gln Lys Tyr Gly Thr Glu Phe Cys Lys Lys Arg
1               5                   10                  15

Leu Ala

<210> SEQ ID NO 514
<211> LENGTH: 8
<212> TYPE: PRT
<213> ORGANISM: Artificial Sequence
<220> FEATURE:
<223> OTHER INFORMATION: Juglans nigra vicilin seed storage protein
      epitope

<400> SEQUENCE: 514

Ser Phe Glu Asp Gln Gly Arg Arg
1               5

<210> SEQ ID NO 515
<211> LENGTH: 15
<212> TYPE: PRT
<213> ORGANISM: Artificial Sequence
<220> FEATURE:
<223> OTHER INFORMATION: Anacardium occidentale Vicilin-like protein
      epitope

<400> SEQUENCE: 515

Ala Ile Met Gly Pro Pro Thr Lys Phe Ser Phe Ser Leu Phe Leu
1               5                   10                  15

<210> SEQ ID NO 516
<211> LENGTH: 10
<212> TYPE: PRT
<213> ORGANISM: Artificial Sequence
```

```
<220> FEATURE:
<223> OTHER INFORMATION: Juglans regia vicilin-like protein precursor
      epitope

<400> SEQUENCE: 516

Asp Gln Arg Ser Gln Glu Glu Arg Glu Arg
1               5                   10
```

TOLEROGENIC SYNTHETIC NANOCARRIERS FOR ALLERGY THERAPY

RELATED APPLICATIONS

This application is a divisional of U.S. patent application Ser. No. 13/457,977, filed Apr. 27, 2012, now U.S. Pat. No. 9,289,476, which claims the benefit under 35 U.S.C. § 119 of U.S. provisional applications 61/480,946, filed Apr. 29, 2011, 61/513,514, filed Jul. 29, 2011, 61/531,147, filed Sep. 6, 2011, 61/531,153, filed Sep. 6, 2011, 61/531,164, filed Sep. 6, 2011, 61/531,168, filed Sep. 6, 2011, 61/531,175, filed Sep. 6, 2011, 61/531,180, filed Sep. 6, 2011, 61/531,194, filed Sep. 6, 2011, 61/531,204, filed Sep. 6, 2011, 61/531,209, filed Sep. 6, 2011, 61/531,215, filed Sep. 6, 2011, the entire contents of each of which are incorporated herein by reference.

FIELD OF THE INVENTION

This invention relates to synthetic nanocarrier compositions with antigens that comprise MHC Class II-restricted epitopes of an allergen and immunosuppressants, and related methods. The compositions and methods allow for efficient and preferential uptake by APCs to shift the immune response in favor of tolerogenic immune response development specific to the allergen. The compositions and methods provided, therefore, can be used to generate a tolerogenic immune response in a subject that is suffering or is expected to suffer from an allergic response to an allergen.

BACKGROUND OF THE INVENTION

Allergic responses in a subject are generally exaggerated and undesired but may be reduced through the use of immunosuppressant drugs. Conventional immunosuppressant drugs, however, are broad-acting. Additionally, in order to maintain immunosuppression, immunosuppressant drug therapy is generally a life-long proposition. Unfortunately, the use of broad-acting immunosuppressants are associated with a risk of severe side effects, such as tumors, infections, nephrotoxicity and metabolic disorders. Accordingly, new immunosuppressant therapies would be beneficial.

SUMMARY OF THE INVENTION

In one aspect, a composition comprising (i) a first population of synthetic nanocarriers that are coupled to immunosuppressants, and (ii) a second population of synthetic nanocarriers that are coupled to MHC Class II-restricted epitopes of an allergen, wherein the composition comprises substantially no B cell epitopes of the allergen is provided. In another embodiment, the first population of synthetic nanocarriers are also coupled to MHC Class I-restricted epitopes of the allergen.

In one embodiment, the first population and second population are the same population. In another embodiment, the first population and second population are different populations.

In yet another embodiment, the immunosuppressants comprise a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterasse 4 inhibitor, an HDAC inhibitor or a proteasome inhibitor. In still another embodiment, the mTOR inhibitor is rapamycin or an analog thereof.

In a further embodiment, the allergen induces, or is expected to induce, an undesired immune response in a subject. In one embodiment, the undesired immune response is allergen-specific antibody production. In another embodiment, the undesired immune response is allergen specific CD4+ T cell proliferation and/or activity. In still another embodiment, the undesired immune response is allergen-specific B cell proliferation and/or activity. In yet a further embodiment, the allergen comprises an asthma antigen, a hay fever antigen, a hives antigen, an eczema antigen, a plant allergen, an insect sting allergen, an insect allergen, an animal allergen, a fungal allergen, a drug allergen, haptens, small chemicals, a pet allergen, a latex allergen, a mold allergen, a cosmetic allergen or a food allergen. In still a further embodiment, the food allergen comprises a milk allergen, an egg allergen, a nut allergen, a fish allergen, a shellfish allergen, a soy allergen, a legume allergen, a seed allergen or a wheat allergen. In another embodiment, the nut allergen is a peanut allergen or a tree nut allergen. In another embodiment, the plant allergen is a ragweed allergen. In yet another embodiment, the allergen is associated with hay fever or allergic asthma.

In one embodiment, the composition is in an amount effective to reduce the undesired immune response to the allergen when administered to a subject. In another embodiment, the subject has or is at risk of having an allergy. In another embodiment, the allergy is allergic asthma, hay fever, hives, eczema, a plant allergy, a pet allergy, a latex allergy, a mold allergy, a cosmetic allergy, a food allergy, an insect sting allergy, an insect allergy, an animal allergy, a fungal allergy, a drug allergy or an allergy to a hapten or small chemical. In yet another embodiment, the food allergy is a milk allergy, an egg allergy, a nut allergy, a fish allergy, a shellfish allergy, a soy allergy, a legume allergy, a seed allergy or a wheat allergy. In still another embodiment, the nut allergy is a peanut allergy or a tree nut allergy. In yet another embodiment, the allergy is hay fever or a ragweed allergy.

In one embodiment, the load of the immunosuppressants and/or epitopes on average across the first and/or second population of synthetic nanocarriers is between 0.0001% and 50%. In another embodiment, the load of the immunosuppressant and/or epitopes on average across the first and/or second population of synthetic nanocarriers is between 0.1% and 10%.

In a further embodiment, the synthetic nanocarriers of the first population and/or second population comprise lipid nanoparticles, polymeric nanoparticles, metallic nanoparticles, surfactant-based emulsions, dendrimers, buckyballs, nanowires, virus-like particles or peptide or protein particles. In yet a further embodiment, the synthetic nanocarriers of the first population and/or second population comprise lipid nanoparticles. In still a further embodiment, the synthetic nanocarriers of the first population and/or second population comprise liposomes. In another embodiment, the synthetic nanocarriers of the first population and/or second population comprise metallic nanoparticles. In yet another embodiment, the metallic nanoparticles comprise gold nanoparticles. In still another embodiment, the synthetic nanocarriers of the first population and/or second population comprise polymeric nanoparticles. In a further embodiment, the polymeric nanoparticles comprise polymer that is a non-methoxy-terminated, pluronic polymer. In one embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In still another embodiment, the polymeric nanoparticles comprise a polyester and a polyester coupled to a polyether. In a further embodiment, the polyether comprises polyethylene glycol or polypropylene glycol.

In another embodiment, the mean of a particle size distribution obtained using dynamic light scattering of the synthetic nanocarriers of the first and/or second population is a diameter greater than 100 nm. In one embodiment, the diameter is greater than 150 nm. In another embodiment, the diameter is greater than 200 nm. In still another embodiment, the diameter is greater than 250 nm. In yet another embodiment, the diameter is greater than 300 nm.

In yet a further embodiment, the aspect ratio of the synthetic nanocarriers of the first population and/or second population is greater than 1:1, 1:1.2, 1:1.5, 1:2, 1:3, 1:5, 1:7 or 1:10. In another embodiment, the composition further comprises a pharmaceutically acceptable excipient.

In another aspect, a dosage form comprising any of the compositions provided herein is provided.

In yet another aspect, any of the compositions or dosage forms provided can be administered to a subject. In one embodiment, the subject has or is at risk of having an allergy. In another embodiment, the subject has or is at risk of having an undesired immune response against an allergen. In still another embodiment, an undesired immune response to an allergen is reduced in the subject with the composition or dosage form. In one embodiment, the undesired immune response is allergen-specific antibody production. In another embodiment, the undesired immune response is allergen-specific CD4+ T cell proliferation and/or activity. In still another embodiment, the undesired immune response is allergen-specific B cell proliferation and/or activity.

In yet another aspect, a method comprising administering to a subject a composition comprising (i) a first population of synthetic nanocarriers that are coupled to immunosuppressants, and (ii) a second population of synthetic nanocarriers that are coupled to MHC Class II-restricted epitopes of an allergen, wherein the composition comprises substantially no B cell epitopes of the allergen, wherein the composition is in an amount effective to reduce an undesired immune response to the allergen in the subject, and wherein the subject is experiencing or is at risk of experiencing the undesired immune response to the allergen is provided. In still another aspect a method comprising reducing an undesired immune response to an allergen in a subject by administering a composition comprising (i) a first population of synthetic nanocarriers that are coupled to immunosuppressants, and (ii) a second population of synthetic nanocarriers that are coupled to MHC Class II-restricted epitopes of the allergen, wherein the composition comprises substantially no B cell epitopes of the allergen, wherein the composition is in an amount effective to reduce the undesired immune response to the allergen in the subject, and wherein the subject is experiencing or is at risk of experiencing the undesired immune response to the allergen is provided. In a further aspect, a method comprising administering a composition to a subject according to a protocol that was previously shown to reduce an undesired immune response to an allergen in one or more test subjects; wherein the composition comprises (i) a first population of synthetic nanocarriers that are coupled to immunosuppressants, and (ii) a second population of synthetic nanocarriers that are coupled to MHC Class II-restricted epitopes of the allergen, wherein the composition comprises substantially no B cell epitopes of the allergen, wherein the composition is in an amount effective to reduce the undesired immune response to the allergen in the subject, and wherein the subject is experiencing or is at risk of experiencing the undesired immune response to the allergen is provided.

In one embodiment, the first population and second population are the same population. In another embodiment, the first population and second population are different populations.

In yet another embodiment, the method further comprises providing or identifying the subject.

In still another embodiment, the immunosuppressants comprise a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterase 4 inhibitor, an HDAC inhibitor or a proteasome inhibitor. In a further embodiment, the mTOR inhibitor is rapamycin or an analog thereof.

In one embodiment, the allergen induces or is expected to induce an undesired immune response in the subject. In one embodiment, the undesired immune response is allergen-specific antibody production. In another embodiment, the undesired immune response is allergen-specific CD4+ T cell proliferation and/or activity. In still another embodiment, the undesired immune response is allergen-specific B cell proliferation and/or activity. In another embodiment, the allergen comprises an asthma antigen, a hay fever antigen, a hives antigen, an eczema antigen, a plant allergen, an insect sting allergen, an insect allergen, an animal allergen, a fungal allergen, a drug allergen, a pet allergen, a latex allergen, a mold allergen, a cosmetic allergen or a food allergen. In yet another embodiment, the food allergen comprises a milk allergen, an egg allergen, a nut allergen, a fish allergen, a shellfish allergen, a soy allergen, a legume allergen, a seed allergen or a wheat allergen. In still another embodiment, the nut allergen is a peanut allergen or a tree nut allergen. In yet another embodiment, the plant allergen is a ragweed allergen.

In a further embodiment, the first population of synthetic nanocarriers are also coupled to MHC Class I-restricted epitopes of the allergen.

In one embodiment, the load of the immunosuppressants and/or epitopes on average across the first and/or second population of synthetic nanocarriers is between 0.0001% and 50%. In another embodiment, the load of the immunosuppressants and/or epitopes on average across the first and/or second population of synthetic nanocarriers is between 0.1% and 10%.

In a further embodiment, the synthetic nanocarriers of the first population and/or second population comprise lipid nanoparticles, polymeric nanoparticles, metallic nanoparticles, surfactant-based emulsions, dendrimers, buckyballs, nanowires, virus-like particles or peptide or protein particles. In yet a further embodiment, the synthetic nanocarriers of the first population and/or second population comprise lipid nanoparticles. In still a further embodiment, the synthetic nanocarriers of the first population and/or second population comprise liposomes. In another embodiment, the synthetic nanocarriers of the first population and/or second population comprise metallic nanoparticles. In yet another embodiment, the metallic nanoparticles comprise gold nanoparticles. In still another embodiment, the synthetic nanocarriers of the first population and/or second population comprise polymeric nanoparticles. In one embodiment, the polymeric nanoparticles comprise non-methoxy-terminated, pluronic polymer. In one embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In still another embodiment, the polymeric nanoparticles comprise a polyester and a polyester coupled to a polyether. In a further embodiment, the polyether comprises polyethylene glycol or polypropylene glycol.

In another embodiment, the mean of a particle size distribution obtained using dynamic light scattering of the synthetic nanocarriers of the first and/or second population is a diameter greater than 100 nm. In one embodiment, the diameter is greater than 150 nm. In another embodiment, the diameter is greater than 200 nm. In still another embodiment, the diameter is greater than 250 nm. In yet another embodiment, the diameter is greater than 300 nm.

In yet a further embodiment, the aspect ratio of the synthetic nanocarriers of the first population and/or second population is greater than 1:1, 1:1.2, 1:1.5, 1:2, 1:3, 1:5, 1:7 or 1:10.

In one embodiment, one or more maintenance doses of the composition comprising the first population and second population of synthetic nanocarriers is administered to the subject. In another embodiment, the method further comprises assessing the undesired immune response to the allergen in the subject prior to and/or after the administration of the composition comprising the first population and second population of synthetic nanocarriers. In one embodiment, the undesired immune response is allergen-specific antibody production. In another embodiment, the undesired immune response if allergen-specific CD4+ T cell proliferation and/or activity. In still another embodiment, the undesired immune response is allergen-specific B cell proliferation and/or activity.

In one embodiment, the subject has or is at risk of having an allergy. In another embodiment, the allergy is allergic asthma, hay fever, hives, eczema, a plant allergy, an insect sting allergy, an insect allergy, an animal allergy, a fungal allergy, a drug allergy, a pet allergy, a latex allergy, a mold allergy, a cosmetic allergy or a food allergy. In yet another embodiment, the food allergy is a milk allergy, an egg allergy, a nut allergy, a fish allergy, a shellfish allergy, a soy allergy, a legume allergy, a seed allergy or a wheat allergy. In still another embodiment, the nut allergy is a peanut allergy or a tree nut allergy. In another embodiment, the plant allergy is a ragweed allergy.

In a further embodiment, the administering is by intravenous, intraperitoneal, transmucosal, oral, subcutaneous, pulmonary, intranasal, intradermal or intramuscular administration. In yet a further embodiment, the administering is by inhalation or intravenous, subcutaneous or transmucosal administration.

In a further aspect, a method comprising (i) producing a first population of synthetic nanocarriers that are coupled to immunosuppressants, (ii) producing a second population of synthetic nanocarriers that are coupled to MHC Class II-restricted epitopes of an allergen, and (iii) ensuring the second population of synthetic nanocarriers comprise substantially no B cell epitopes of the allergen is provided.

In one embodiment, the first population and second population are the same population. In another embodiment, the first population and second population are different populations.

In yet another embodiment, the method further comprises making a dosage form comprising the first population and second population of synthetic nanocarriers. In still another embodiment, the method further comprises making a composition comprising the first population and second population of synthetic nanocarriers or a dosage form thereof available to a subject for administration.

In another embodiment, the first population and second population of synthetic nanocarriers that are produced are as defined in any of the methods provided herein. In a further embodiment, the method further comprises assessing an undesired immune response to the allergen with a composition comprising the first population and second population of synthetic nanocarriers. In one embodiment, the undesired immune response in a subject is assessed.

In yet a further aspect, a process for producing a composition or dosage form comprising the steps of coupling a first population of synthetic nanocarriers to immunosuppressants; coupling a second population of synthetic nanocarriers to MHC Class II-restricted epitopes of an allergen; and ensuring the second population of synthetic nanocarriers comprise substantially no B cell epitopes of the allergen is provided. In one embodiment, the process comprises the steps of any of the methods provided herein.

In another aspect, a composition or dosage form obtainable by any of the methods or processes provided herein is provided.

In still another aspect, any of the compositions or dosage forms provided herein may be for use in therapy or prophylaxis.

In yet another aspect, any of the compositions or dosage forms provided herein may be for use in a method of reducing an undesired immune response to an allergen in a subject, the treatment or prophylaxis of allergy, or any of the methods provided herein.

In a further aspect, a use of any of the compositions or dosage forms provided herein for the manufacture of a medicament for use in a method of reducing an undesired immune response to an allergen in a subject, the treatment or prophylaxis of allergy, or any of the methods provided herein is provided.

In yet a further aspect, a dosage form comprising any of the compositions provided herein is provided.

In an embodiment of any of the compositions and methods provided herein, antigens that are proteins that comprise the aforementioned epitopes can be coupled to the synthetic nanocarriers. In another embodiment, polypeptides or peptides that comprise the aforementioned epitopes but additional amino acids that flank one or both ends of the epitope(s) can be coupled to the synthetic nanocarriers. In another embodiment, the epitopes themselves are coupled to the synthetic nanocarriers.

DETAILED DESCRIPTION OF THE INVENTION

Figure 1:
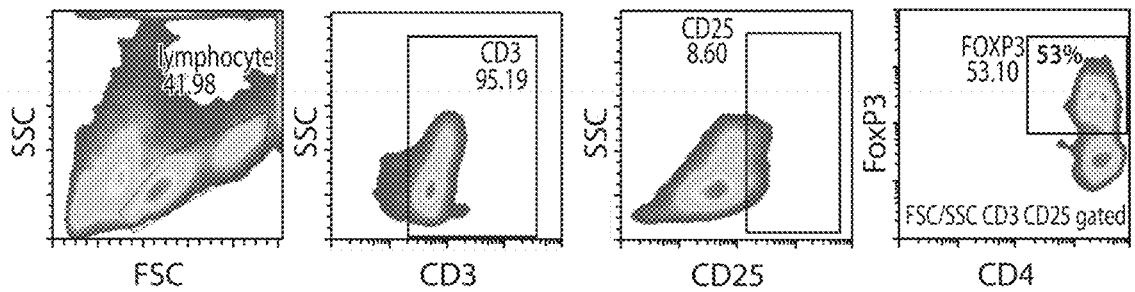
FIG. 1 shows results from a flow cytometric analysis of Treg.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a DNA molecule" includes a mixture of two or more such DNA molecules or a plurality of such DNA molecules, reference to "an immunosuppressant" includes a mixture of two or more such materials or a plurality of immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A. INTRODUCTION

As previously mentioned, current conventional immunosuppressants are broad acting and generally result in an overall systemic down regulation of the immune system. The compositions and methods provided herein allow for more targeted immune effects by, for example, allowing for the targeted delivery to immune cells of interest. Thus, the compositions and methods can achieve immune suppression in a more directed manner. It has been found that delivering immunosuppressants and MHC Class II-restricted epitopes of an allergen more directly to cells of interest, in particular APCs, can result in beneficial tolerogenic immune responses, such as the reduction in antibody production, CD4+ T cell proliferation and/or activity etc., specific to the allergen. Such immune responses can be beneficial in subjects who suffer from allergies. This invention is useful, for example, to promote tolerogenic immune responses in subjects who are experiencing or are at risk of experiencing undesired immune responses to allergens. Such subjects include those who have or are at risk of having an allergy.

The inventors have unexpectedly and surprisingly discovered that the problems and limitations noted above can be overcome by practicing the invention disclosed herein. In particular, the inventors have unexpectedly discovered that it is possible to provide synthetic nanocarrier compositions, and related methods, that induce a tolerogenic immune response to allergens that comprise MHC Class II-restricted epitopes of an allergen. Such compositions can reduce an undesired immune response to the allergen. The compositions described herein include compositions that comprise (i) a first population of synthetic nanocarriers that are coupled to immunosuppressants, and (ii) a second population of synthetic nanocarriers that are coupled to MHC Class II-restricted epitopes of an allergen. In embodiments, MHC Class I-restricted epitopes may also be coupled to the synthetic nanocarriers. In some embodiments, substantially no B cell epitopes of the allergen are coupled and such epitopes may be specifically excluded from the compositions and methods provided herein.

In another aspect, dosage forms of any of the compositions herein are provided. Such dosage forms can be administered to a subject, such as one in need of allergen-specific tolerogenic immune responses. In one embodiment, the subject is one who has had, is having or is expected to have an undesired immune response against an allergen. Such subjects include those that have or are at risk of having an allergy.

In another aspect, any of the compositions provided herein is administered to a subject. The composition may be administered in an amount effective to reduce the generation of an undesired immune response to an allergen. In one embodiment, a composition is administered to a subject according to a protocol that was previously shown to reduce the generation of an undesired immune response to an allergen in one or more subjects.

The compositions may be administered to a subject prior to, concomitantly with or after the exposure of a subject to an allergen. In embodiments, the compositions provided may also be administered as one or more maintenance doses to a subject that has or is at risk of having an allergy. In such embodiments, the compositions provided are administered such that the generation of an undesired immune response is reduced for a certain length of time. Examples of such lengths of time are provided elsewhere herein.

In yet another aspect, a method of (i) producing a first population of synthetic nanocarriers that are coupled to immunosuppressants, and (ii) producing a second population of synthetic nanocarriers that are coupled to MHC Class II-restricted epitopes of an allergen is provided. In embodiments, MHC Class I-restricted epitopes of the allergen may also be coupled to the synthetic nanocarriers. In another embodiment, substantially no B cell epitopes of the allergen are coupled to the synthetic nanocarriers.

The invention will now be described in more detail below.

B. DEFINITIONS

"Administering" or "administration" means providing a material to a subject in a manner that is pharmacologically useful.

"Allergen-specific" refers to any immune response that results from the presence of the allergen, or portion thereof, or that generates molecules that specifically recognize or bind the allergen. For example, where the immune response is allergen-specific antibody production, antibodies are produced that specifically bind the allergen. As another example, where the immune response is allergen-specific B cell or CD4+ T cell proliferation and/or activity, the proliferation and/or activity results from recognition of the allergen, or portion thereof, alone or in complex with MHC molecules, B cells, etc.

"Allergens" are any substances that can cause an undesired (e.g., a Type 1 hypersensitive) immune response (i.e., an allergic response or reaction) in a subject. Allergens include, but are not limited to, plant allergens (e.g., pollen, ragweed allergen), insect allergens, insect sting allergens (e.g., bee sting allergens), animal allergens (e.g., pet allergens, such as animal dander or cat Fel d 1 antigen), latex allergens, mold allergens, fungal allergens, cosmetic allergens, drug allergens, food allergens, dust, insect venom, viruses, bacteria, etc. Food allergens include, but are not limited to milk allergens, egg allergens, nut allergens (e.g., peanut or tree nut allergens, etc. (e.g., walnuts, cashews, etc.)), fish allergens, shellfish allergens, soy allergens, legume allergens, seed allergens and wheat allergens. Insect sting allergens include allergens that are or are associated with bee stings, wasp stings, hornet stings, yellow jacket stings, etc. Insect allergens also include house dust mite allergens (e.g., Der P1 antigen) and cockroach allergens. Drug allergens include allergens that are or are associated with antibiotics, NSAIDs, anaesthetics, etc. Pollen allergens include grass allergens, tree allergens, weed allergens, flower allergens, etc. Subjects that develop or are at risk of developing an undesired immune response to any of the allergens provided herein may be treated with any of the compositions and methods provided herein. Subjects that may be treated with any of the compositions and methods provided also include those who have or are at risk of having an allergy to any of the allergens provided. "Allergens associated with an allergy" are allergens that generate an undesired immune response that results in, or would be expected by a clinician to result in, alone or in combination with other allergens, an allergic response or reaction or a symptom of an allergic response or reaction in a subject. "Type(s) of allergens" means molecules that share the same, or substantially the same, antigenic characteristics in the context of an undesired immune response. In some embodiments, the allergens may be proteins, polypeptides, peptides, lipoproteins or are contained or expressed in cells.

It is intended that MHC Class II-restricted epitopes are preferably coupled to the synthetic nanocarriers as provided herein. The epitopes themselves may be coupled or proteins, polypeptides, peptides, etc. that comprise these epitopes may be coupled to the synthetic nanocarriers. Thus an allergen itself or a portion thereof that comprises MHC Class II-restricted epitopes may be coupled to the synthetic nanocarriers in the compositions provided herein. In some embodiments, MHC Class I-restricted epitopes may also be coupled. Therefore, in some embodiments, the allergen itself or portion thereof comprises both MHC Class II-restricted and MHC Class I-restricted epitopes. The epitopes for use in the compositions and methods provided herein can be presented for recognition by cells of the immune system, such as presented by antigen presenting cells, which include but are not limited to dendritic cells, B cells or macrophages. The epitopes can be presented for recognition by, for example, T cells. Such epitopes may normally be recognized by and trigger an immune response in a T cell via presentation major histocompatability complex molecule (MHC), but in the compositions provided herein the presence of such epitopes in combination with an immunosuppressant can result in tolerogenic immune responses instead. In some embodiments, substantially no B cell epitopes are coupled to the synthetic nanocarriers, such as when the inclusion of the B cell epitopes would exacerbate an undesired immune response and thus, the allergens or portions thereof do not comprise B cell epitopes or do comprise B cell epitopes but such epitopes do not significantly negatively impact the desired immune responses.

An allergen can be coupled to the synthetic nanocarriers in the same form as what a subject is exposed to that causes an undesired immune response but may also be a fragment or derivative thereof. When a fragment or derivative, however, a desired immune response to the form encountered by such a subject is the preferable result with the compositions and methods provided.

An "allergy" also referred to herein as an "allergic condition," is any condition where there is an undesired (e.g., a Type 1 hypersensitive) immune response (i.e., allergic response or reaction) to a substance. Such substances are referred to herein as allergens. Allergies or allergic conditions include, but are not limited to, allergic asthma, hay fever, hives, eczema, plant allergies, bee sting allergies, pet allergies, latex allergies, mold allergies, cosmetic allergies, food allergies, allergic rhinitis or coryza, topic allergic reactions, anaphylaxis, atopic dermatitis, hypersensitivity reactions and other allergic conditions. The allergic reaction may be the result of an immune reaction to any allergen. In some embodiments, the allergy is a food allergy. Food allergies include, but are not limited to, milk allergies, egg allergies, nut allergies, fish allergies, shellfish allergies, soy allergies or wheat allergies.

"Amount effective" in the context of a composition or dosage form for administration to a subject refers to an amount of the composition or dosage form that produces one or more desired immune responses in the subject, for example, the generation of a tolerogenic immune response (e.g, a reduction in the proliferation, activation, induction, recruitment of allergen-specific CD4+ T cells or allergen-specific B cells or a reduction in the production of allergen-specific antibodies). Therefore, in some embodiments, an amount effective is any amount of a composition provided herein that produces one or more of these desired immune responses. This amount can be for in vitro or in vivo purposes. For in vivo purposes, the amount can be one that a clinician would believe may have a clinical benefit for a subject in need of allergen-specific tolerization. Such subjects include those that have or are at risk of having an allergy or an allergic response against an allergen.

Amounts effective can involve only reducing the level of an undesired immune response, although in some embodiments, it involves preventing an undesired immune response altogether. Amounts effective can also involve delaying the occurrence of an undesired immune response. An amount that is effective can also be an amount of a composition provided herein that produces a desired therapeutic endpoint or a desired therapeutic result. Amounts effective, preferably, result in a tolerogenic immune response in a subject to an allergen. The achievement of any of the foregoing can be monitored by routine methods.

In some embodiments of any of the compositions and methods provided, the amount effective is one in which the desired immune response persists in the subject for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of any of the compositions and methods provided, the amount effective is one which produces a measurable desired immune response, for example, a measurable decrease in an immune response (e.g., to a specific allergen), for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the immunosuppressants and/or antigens in the compositions of the invention can range from about 10 µg/kg to about 100,000 µg/kg. In some embodiments, the doses can range from about 0.1 mg/kg to about 100 mg/kg. In still other embodiments, the doses can range from about 0.1 mg/kg to about 25 mg/kg, about 25 mg/kg to about 50 mg/kg, about 50 mg/kg to about 75 mg/kg or about 75 mg/kg to about 100 mg/kg. Alternatively, the dose can be administered based on the number of synthetic nanocarriers that provide the desired amount of immunosuppressants and/or antigens. For example, useful doses include greater than $10^6$, $10^7$, $10^8$, $10^9$ or $10^{10}$ synthetic nanocarriers per dose. Other examples of useful doses include from about $1\times10^6$ to about $1\times10^{10}$, about $1\times10^7$ to about $1\times10^9$ or about $1\times10^8$ to about $1\times10^9$ synthetic nanocarriers per dose.

"Antigen" means a B cell antigen or T cell antigen. Antigens include allergens or fragments or derivatives of allergens that can generate an immune response alone or in conjunction with another agent, carrier, etc.

"Assessing an immune response" refers to any measurement or determination of the level, presence or absence, reduction, increase in, etc. of an immune response in vitro or in vivo. Such measurements or determinations may be performed on one or more samples obtained from a subject. Such assessing can be performed with any of the methods provided herein or otherwise known in the art.

An "at risk" subject is one in which a health practitioner believes has a chance of having a disease, disorder or condition as provided herein or is one a health practitioner believes has a chance of experiencing an undesired immune response as provided herein.

"Average", as used herein, refers to the arithmetic mean unless otherwise noted.

"B cell antigen" means any antigen that triggers an immune response in a B cell (e.g., an antigen that is specifically recognized by a B cell or a receptor thereon). In some embodiments, an antigen that is a T cell antigen is also a B cell antigen. In other embodiments, the T cell antigen is not also a B cell antigen. B cell antigens include, but are not limited to proteins, peptides, small molecules, and carbohydrates. In some embodiments, the B cell antigen comprises a non-protein antigen (i.e., not a protein or peptide antigen). In some embodiments, the B cell antigen is obtained or derived from an allergen.

"Concomitantly" means administering two or more substances to a subject in a manner that is correlated in time, preferably sufficiently correlated in time so as to provide a modulation in an immune response. In embodiments, concomitant administration may occur through administration of two or more substances in the same dosage form. In other embodiments, concomitant administration may encompass administration of two or more substances in different dosage forms, but within a specified period of time, preferably within 1 month, more preferably within 1 week, still more preferably within 1 day, and even more preferably within 1 hour.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of coupling.

"Derived" means prepared from a material or information related to a material but is not "obtained" from the material. Such materials may be substantially modified or processed forms of materials taken directly from a biological material. Such materials also include materials produced from information related to a biological material.

"Dosage form" means a pharmacologically and/or immunologically active material in a medium, carrier, vehicle, or device suitable for administration to a subject.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Epitope", also known as an antigenic determinant, is the part of an antigen that is recognized by the immune system, specifically by, for example, antibodies, B cells, or T cells. As used herein, "MHC Class I-restricted epitopes" are epitopes that are presented to immune cells by MHC class I molecules found on nucleated cells. "MHC Class II-restricted epitopes" are epitopes that are presented to immune cells by MHC class II molecules found on antigen-presenting cells (APCs), for example, on professional antigen-presenting immune cells, such as on macrophages, B cells, and dendritic cells, or on non-hematopoietic cells, such as hepatocytes. "B cell epitopes" are molecular structures that are recognized by antibodies or B cells. In some embodiments, the epitope itself is an antigen.

A number of epitopes are known to those of skill in the art, and exemplary epitopes suitable according to some aspects of this invention include, but are not limited to those listed in the Immune Epitope Database (www.immuneepitope.org, Vita R, Zarebski L, Greenbaum J A, Emami H, Hoof I, Salimi N, Damle R, Sette A, Peters B. The immune epitope database 2.0. Nucleic Acids Res. 2010 January; 38(Database issue):D854-62; the entire contents of which as well as all database entries of IEDB version 2.4, August 2011, and particularly all epitopes disclosed therein, are incorporated herein by reference). Epitopes can also be identified with publicly available algorithms, for example, the algorithms described in Wang P, Sidney J, Kim Y, Sette A, Lund O, Nielsen M, Peters B. 2010. peptide binding predictions for HLA DR, DP and DQ molecules. BMC Bioinformatics 2010, 11:568; Wang P, Sidney J, Dow C, Mothé B, Sette A, Peters B. 2008. A systematic assessment of MHC class II peptide binding predictions and evaluation of a consensus approach. PLoS Comput Biol. 4(4):e1000048; Nielsen M, Lund O. 2009. NN-align. An artificial neural network-based alignment algorithm for MHC class II peptide binding prediction. BMC Bioinformatics. 10:296; Nielsen M, Lundegaard C, Lund O. 2007. Prediction of MHC class II binding affinity using SMM-align, a novel stabilization matrix alignment method. BMC Bioinformatics. 8:238; Bui H H, Sidney J, Peters B, Sathiamurthy M, Sinichi A, Purton K A, Mothé B R, Chisari F V, Watkins D I, Sette A. 2005. Immunogenetics. 57:304-314; Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. Nat Biotechnol. 17(6):555-561; Nielsen M, Lundegaard C, Worning P, Lauemoller S L, Lamberth K, Buus S, Brunak S, Lund O. 2003. Reliable prediction of T-cell epitopes using neural networks with novel sequence representations. Protein Sci 12:1007-1017; Bui H H, Sidney J, Peters B, Sathiamurthy M, Sinichi A, Purton K A, Mothe B R, Chisari F V, Watkins D I, Sette A. 2005. Automated generation and evaluation of specific MHC binding predictive tools: ARB matrix applications. Immunogenetics 57:304-314; Peters B, Sette A. 2005. Generating quantitative models describing the sequence specificity of biological processes with the stabilized matrix method. BMC Bioinformatics 6:132; Chou P Y, Fasman G D. 1978. Prediction of the secondary structure of proteins from their amino acid sequence. Adv Enzymol Relat Areas Mol Biol 47:45-148; Emini E A, Hughes J V, Perlow D S, Boger J. 1985. Induction of hepatitis A virus-neutralizing antibody by a virus-specific synthetic peptide. J Virol 55:836-839; Karplus P A, Schulz G E. 1985. Prediction of chain flexibility in proteins. Naturwissenschaften 72:212-213; Kolaskar A S, Tongaonkar P C. 1990. A semi-empirical method for prediction of antigenic determinants on protein antigens. FEBS Lett 276:172-174; Parker J M, Guo D, Hodges R S. 1986. New hydrophilicity scale derived from high-performance liquid chromatography peptide retention data: correlation of predicted surface residues with antigenicity and X-ray-derived accessible sites. Biochemistry 25:5425-5432; Larsen J E, Lund O, Nielsen M. 2006. Improved method for predicting linear B-cell epitopes. Immunome Res 2:2; Ponomarenko J V, Bourne P E. 2007. Antibody-protein interactions: benchmark datasets and prediction tools evaluation. BMC Struct Biol 7:64; Haste Andersen P, Nielsen M, Lund O. 2006. Prediction of residues in discontinuous B-cell epitopes using protein 3D structures. Protein Sci 15:2558-2567; Ponomarenko J V, Bui H, Li W, Fusseder N, Bourne P E, Sette A, Peters B. 2008. ElliPro: a new structure-based tool for the prediction of antibody epitopes. BMC Bioinformatics 9:514; Nielsen M, Lundegaard C, Blicher T, Peters B, Sette A, Justesen S, Buus S, and Lund O. 2008. PLoS Comput Biol. 4(7)e1000107. Quantitative predictions of peptide binding to any HLA-DR molecule of known sequence: NetMHCIIpan; the entire contents of each of which are incorporated herein by reference for disclosure of methods and algorithms for the identification of epitopes.

Other examples of epitopes as provided herein include any of the allergen-associated MHC Class II-restricted and B cell epitopes as provided as SEQ ID NOs: 1-516. Without wishing to being bound by any particular theory, MHC Class II-restricted epitopes include those set forth in SEQ ID NOs: 1-338 and B cell epitopes include those set forth in SEQ ID NOs: 339-516.

"Generating" means causing an action, such as an immune response (e.g., a tolerogenic immune response) to occur, either directly oneself or indirectly, such as, but not limited to, an unrelated third party that takes an action through reliance on one's words or deeds.

"Identifying" is any action or set of actions that allows a clinician to recognize a subject as one who may benefit from the methods and compositions provided herein. Preferably, the identified subject is one who is in need of a tolerogenic immune response as provided herein. The action or set of actions may be either directly oneself or indirectly, such as, but not limited to, an unrelated third party that takes an action through reliance on one's words or deeds.

"Immunosuppressant" means a compound that causes an APC to have an immunosuppressive (e.g., tolerogenic) effect). An immunosuppressive effect generally refers to the production or expression of cytokines or other factors by the APC that reduces, inhibits or prevents an undesired immune response or that promotes a desired immune response. When the APC results in an immunosuppressive effect on immune cells that recognize an antigen presented by the APC, the immunosuppressive effect is said to be specific to the presented antigen. Such effect is also referred to herein as a tolerogenic effect. Without being bound by any particular theory, it is thought that the immunosuppressive or tolerogenic effect is a result of the immunosuppressant being delivered to the APC, preferably in the presence of an antigen (e.g., an administered antigen or one that is already present in vivo). Accordingly, the immunosuppressant includes compounds that provide a tolerogenic immune response to an antigen that may or may not be provided in the same composition or a different composition. In one embodiment, the immunosuppressant is one that causes an APC to promote a regulatory phenotype in one or more immune effector cells. For example, the regulatory phenotype may be characterized by the inhibition of the production, induction, stimulation or recruitment of allergen-specific CD4+ T cells or B cells, the inhibition of the production of allergen-specific antibodies, the production, induction, stimulation or recruitment of Treg cells (e.g., CD4+ CD25highFoxP3+ Treg cells), etc. This may be the result of the conversion of CD4+ T cells or B cells to a regulatory phenotype. This may also be the result of induction of FoxP3 in other immune cells, such as CD8+ T cells, macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol and triptolide. In embodiments, the immunosuppressant may comprise any of the agents provided herein.

The immunosuppressant can be a compound that directly provides the immunosuppressive (e.g., tolerogenic) effect on APCs or it can be a compound that provides the immunosuppressive (e.g., tolerogenic) effect indirectly (i.e., after being processed in some way after administration). Immunosuppressants, therefore, include prodrug forms of any of the compounds provided herein.

Immunosuppressants also include nucleic acids that encode the peptides, polypeptides or proteins provided herein that result in an immunosuppressive (e.g., tolerogenic) immune response. In embodiments, therefore, the immunosuppressant is a nucleic acid that encodes a peptide, polypeptide or protein that results in an immunosuppressive (e.g., tolerogenic) immune response, and it is the nucleic acid that is coupled to the synthetic nanocarrier.

The nucleic acid may be DNA or RNA, such as mRNA. In embodiments, the inventive compositions comprise a complement, such as a full-length complement, or a degenerate (due to degeneracy of the genetic code) of any of the nucleic acids provided herein. In embodiments, the nucleic acid is an expression vector that can be transcribed when transfected into a cell line. In embodiments, the expression vector may comprise a plasmid, retrovirus, or an adenovirus amongst others. Nucleic acids can be isolated or synthesized using standard molecular biology approaches, for example by using a polymerase chain reaction to produce a nucleic acid fragment, which is then purified and cloned into an expression vector. Additional techniques useful in the practice of this invention may be found in Current Protocols in Molecular Biology 2007 by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor.

In embodiments, the immunosuppressants provided herein are coupled to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and coupled to the one or more polymers. As another example, in one embodiment, where the synthetic nanocarrier is made up of one or more lipids, the immunosuppressant is again in addition and coupled to the one or more lipids. In embodiments, such as where the material of the synthetic nanocarrier also results in an immunosuppressive (e.g., tolerogenic) effect, the immunosuppressant is an element present in addition to the material of the synthetic nanocarrier that results in an immunosuppressive (e.g., tolerogenic) effect.

Other exemplary immunosuppressants include, but are not limited, small molecule drugs, natural products, antibodies (e.g., antibodies against CD20, CD3, CD4), biologics-based drugs, carbohydrate-based drugs, nanoparticles, liposomes, RNAi, antisense nucleic acids, aptamers, methotrexate, NSAIDs; fingolimod; natalizumab; alemtuzumab; anti-CD3; tacrolimus (FK506), etc. Further immunosuppressants, are known to those of skill in the art, and the invention is not limited in this respect.

"Load" of the immunosuppressant or antigen is the amount of the immunosuppressant or antigen coupled to a synthetic nanocarrier based on the total weight of materials in an entire synthetic nanocarrier (weight/weight). Generally, the load is calculated as an average across a population of synthetic nanocarriers. In one embodiment, the load of the immunosuppressant on average across the first population of synthetic nanocarriers is between 0.0001% and 50%. In another embodiment, the load of the antigen on average across the first and/or second population of synthetic nanocarriers is between 0.0001% and 50%. In yet another embodiment, the load of the immunosuppressant and/or antigen is between 0.01% and 20%. In a further embodiment, the load of the immunosuppressant and/or antigen is between 0.1% and 10%. In still a further embodiment, the load of the immunosuppressant and/or antigen is between 1% and 10%. In yet another embodiment, the load of the immunosuppressant and/or the antigen is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% on average across a population of synthetic nanocarriers. In yet a further embodiment, the load of the immunosuppressant and/or the antigen is 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% on average across a population of synthetic nanocarriers. In some embodiments of the above embodiments, the load of the immunosuppressant and/or the antigen is no more than 25% on average across a population of synthetic nanocarriers. In embodiments, the load is calculated as described in the Examples.

In embodiments of any of the compositions and methods provided, the load may be calculated as follows: Approximately 3 mg of synthetic nanocarriers are collected and centrifuged to separate supernatant from synthetic nanocarrier pellet. Acetonitrile is added to the pellet, and the sample is sonicated and centrifuged to remove any insoluble material. The supernatant and pellet are injected on RP-HPLC and absorbance is read at 278 nm. The µg found in the pellet is used to calculate % entrapped (load), µg in supernatant and pellet are used to calculate total µg recovered.

"Maintenance dose" refers to a dose that is administered to a subject, after an initial dose has resulted in an immunosuppressive (e.g., tolerogenic) response in a subject, to sustain a desired immunosuppressive (e.g., tolerogenic) response. A maintenance dose, for example, can be one that maintains the tolerogenic effect achieved after the initial dose, prevents an undesired immune response in the subject, or prevents the subject becoming a subject at risk of experiencing an undesired immune response, including an undesired level of an immune response. In some embodiments, the maintenance dose is one that is sufficient to sustain an appropriate level of a desired immune response.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., diameter) is obtained by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. "Dimension" or "size" or "diameter" of synthetic nanocarriers means the mean of a particle size distribution obtained using dynamic light scattering.

"MHC" refers to major histocompatibility complex, a large genomic region or gene family found in most vertebrates that encodes MHC molecules that display fragments or epitopes of processed proteins on the cell surface. The presentation of MHC:peptide on cell surfaces allows for surveillance by immune cells, usually a T cell. There are two general classes of MHC molecules: Class I and Class II. Generally, Class I MHC molecules are found on nucleated cells and present peptides to cytotoxic T cells. Class II MHC molecules are found on certain immune cells, chiefly macrophages, B cells and dendritic cells, collectively known as professional APCs. The best-known genes in the MHC region are the subset that encodes antigen-presenting proteins on the cell surface. In humans, these genes are referred to as human leukocyte antigen (HLA) genes.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Obtained" means taken directly from a material and used with substantially no modification and/or processing.

"Pharmaceutically acceptable excipient" means a pharmacologically inactive material used together with the recited synthetic nanocarriers to formulate the inventive compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Protocol" refers to any dosing regimen of one or more substances to a subject. A dosing regimen may include the amount, frequency and/or mode of administration. In some embodiments, such a protocol may be used to administer one or more compositions of the invention to one or more test subjects. Immune responses in these test subject can then be assessed to determine whether or not the protocol was effective in reducing an undesired immune response or generating a desired immune response (e.g., the promotion of a tolerogenic effect). Any other therapeutic and/or prophylactic effect may also be assessed instead of or in addition to the aforementioned immune responses. Whether or not a protocol had a desired effect can be determined using any of the methods provided herein or otherwise known in the art. For example, a population of cells may be obtained from a subject to which a composition provided herein has been administered according to a specific protocol in order to determine whether or not specific immune cells, cytokines, antibodies, etc. were reduced, generated, activated, etc. Useful methods for detecting the presence and/or number of immune cells include, but are not limited to, flow cytometric methods (e.g., FACS) and immunohistochemistry methods. Antibodies and other binding agents for specific staining of immune cell markers, are commercially available. Such kits typically include staining reagents for multiple antigens that allow for FACS-based detection, separation and/or quantitation of a desired cell population from a heterogeneous population of cells.

"Providing a subject" is any action or set of actions that causes a clinician to come in contact with a subject and administer a composition provided herein thereto or to perform a method provided herein thereupon. Preferably, the subject is one who is in need of a tolerogenic immune response as provided herein. The action or set of actions may be either directly oneself or indirectly, such as, but not limited to, an unrelated third party that takes an action through reliance on one's words or deeds.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Substantially no B cell epitopes" refers to the absence of B cell epitopes in an amount (by itself, within the context of the allergen, in conjunction with a carrier or in conjunction with an inventive composition) that stimulates substantial activation of a B cell response. In embodiments, a composition with substantially no B cell epitopes does not contain a measurable amount of B cell epitopes of an allergen. In other embodiments, such a composition may comprise a measurable amount of B cell epitopes of an allergen but said amount is not effective to generate a measurable B cell immune response (by itself, within the context of the antigen, in conjunction with a carrier, or in conjunction with an inventive composition), such as allergen-specific antibody production or allergen-specific B cell proliferation and/or activity, or is not effective to generate a significant measurable B cell immune response (by itself, within the context of the antigen, in conjunction with a carrier or in conjunction with an inventive composition). In some embodiments, a significant measurable B cell immune response is one that produces or would be expected to produce an adverse clinical result in a subject. In other embodiments, a significant measurable B cell immune response is one that is greater than the level of the same type of immune response (e.g., allergen-specific antibody production or allergen-specific B cell proliferation and/or activity) produced by a control antigen (e.g., one known not to comprise B cell epitopes of the allergen or to stimulate B cell immune responses). In some embodiments, a significant measurable B cell immune response, such as a measurement of antibody titers (e.g., by ELISA) is 2-fold, 3-fold, 4-fold, 5-fold, 6-fold, 7-fold, 8-fold, 9-fold, 10-fold, 15-fold, 20-fold or more greater than the same type of response produced by a control (e.g., a control antigen). In other embodiments, a composition with substantially no B cell epitopes is one that produces little to no allergen-specific antibody titers (by itself, within the context of the antigen, in conjunction with a carrier or in conjunction with an inventive composition). Such compositions include those that produce an antibody titer (as an EC50 value) of less than 500, 400, 300, 200, 100, 50, 40, 30, 20 or 10. In other embodiments, a significant measurable B cell immune response, is a measurement of the number or proliferation of B cells that is 10%, 25%, 50%, 100%, 2-fold, 3-fold, 4-fold, 5-fold, 6-fold, 7-fold, 8-fold, 9-fold, 10-fold, 15-fold, 20-fold or more greater that the same type of response produced by a control. Other methods for measuring B cell responses are known to those of ordinary skill in the art.

In embodiments, to ensure that a composition comprises substantially no B cell epitopes, antigens are selected such that they do not comprise B cell epitopes for coupling to the synthetic nanocarriers as provided herein. In other embodiments, to ensure that a composition comprises substantially no B cell epitopes of an allergen, the synthetic nanocarriers coupled to the epitopes are produced and tested for B cell immune responses (e.g., B cell proliferation and/or activity, allergen-specific antibody production). Compositions that exhibit the desired properties may then be selected.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, inventive synthetic nanocarriers do not comprise chitosan. In other embodiments, inventive synthetic nanocarriers are not lipid-based nanoparticles. In further embodiments, inventive synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), or (11) apoptotic cells, apoptotic bodies or the synthetic or semisynthetic mimics disclosed in U.S. Publication 2002/0086049. In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"T cell antigen" means a CD4+ T-cell antigen or CD8+ cell antigen. "CD4+ T-cell antigen" means any antigen that is recognized by and triggers an immune response in a CD4+ T-cell e.g., an antigen that is specifically recognized by a T-cell receptor on a CD4+ T cell via presentation of the antigen or portion thereof bound to a Class II major histocompatability complex molecule (MHC). "CD8+ T cell antigen" means any antigen that is recognized by and triggers an immune response in a CD8+ T-cell e.g., an antigen that is specifically recognized by a T-cell receptor on a CD8+ T cell via presentation of the antigen or portion thereof bound to a Class I major histocompatability complex molecule (MHC). In some embodiments, an antigen that is a T cell antigen is also a B cell antigen. In other embodiments, the T cell antigen is not also a B cell antigen. T cell antigens generally are proteins or peptides.

"Tolerogenic immune response" means any immune response that can lead to immune suppression specific to an antigen or a cell, tissue, organ, etc. that expresses such an antigen. Such immune responses include any reduction, delay or inhibition in an undesired immune response specific to the antigen or cell, tissue, organ, etc. that expresses such antigen. Such immune responses also include any stimulation, production, induction, promotion or recruitment in a desired immune response specific to the antigen or cell, tissue, organ, etc. that expresses such antigen. Tolerogenic immune responses, therefore, include the absence of or reduction in an undesired immune response to an antigen that can be mediated by antigen reactive cells as well as the presence or promotion of suppressive cells. Tolerogenic immune responses as provided herein include immunological tolerance. To "generate a tolerogenic immune response" refers to the generation of any of the foregoing immune responses specific to an antigen or cell, tissue, organ, etc. that expresses such antigen. The tolerogenic immune response can be the result of MHC Class I-restricted presentation and/or MHC Class II-restricted presentation and/or B cell presentation and/or presentation by CD1d, etc.

Tolerogenic immune responses include any reduction, delay or inhibition in CD4+ T cell, CD8+ T cell or B cell proliferation and/or activity. Tolerogenic immune responses also include a reduction in antigen-specific antibody production. Tolerogenic immune responses can also include any response that leads to the stimulation, induction, production or recruitment of regulatory cells, such as CD4+ Treg cells, CD8+ Treg cells, Breg cells, etc. In some embodiments, the tolerogenic immune response, is one that results in the conversion to a regulatory phenotype characterized by the production, induction, stimulation or recruitment of regulatory cells.

Tolerogenic immune responses also include any response that leads to the stimulation, production or recruitment of CD4+ Treg cells and/or CD8+ Treg cells. CD4+ Treg cells can express the transcription factor FoxP3 and inhibit inflammatory responses and auto-immune inflammatory diseases (Human regulatory T cells in autoimmune diseases. Cvetanovich G L, Hafler D A. Curr Opin Immunol. 2010 December; 22(6):753-60. Regulatory T cells and autoimmunity. Vila J, Isaacs J D, Anderson A E. Curr Opin Hematol. 2009 July; 16(4):274-9). Such cells also suppress T-cell help to B-cells and induce tolerance to both self and foreign antigens (Therapeutic approaches to allergy and autoimmunity based on FoxP3+ regulatory T-cell activation and expansion. Miyara M, Wing K, Sakaguchi S. J Allergy Clin Immunol. 2009 April; 123(4):749-55). CD4+ Treg cells recognize antigen when presented by Class II proteins on APCs. CD8+ Treg cells, which recognize antigen presented by Class I (and Qa-1), can also suppress T-cell help to B-cells and result in activation of antigen-specific suppression inducing tolerance to both self and foreign antigens. Disruption of the interaction of Qa-1 with CD8+ Treg cells has been shown to dysregulate immune responses and results in the development of auto-antibody formation and an auto-immune lethal systemic-lupus-erythematosus (Kim et al., Nature. 2010 Sep. 16, 467 (7313): 328-32). CD8+ Treg cells have also been shown to inhibit models of autoimmune inflammatory diseases including rheumatoid arthritis and colitis (CD4+CD25+ regulatory T cells in autoimmune arthritis. Oh S, Rankin A L, Caton A J. Immunol Rev. 2010 January; 233(1):97-111. Regulatory T cells in inflammatory bowel disease. Boden E K, Snapper S B. Curr Opin Gastroenterol. 2008 November; 24(6):733-41). In some embodiments, the compositions provided can effectively result in both types of responses (CD4+ Treg and CD8+ Treg). In other embodiments, FoxP3 can be induced in other immune cells, such as macrophages, iNKT cells, etc., and the compositions provided herein can result in one or more of these responses as well.

Tolerogenic immune responses also include, but are not limited to, the induction of regulatory cytokines, such as Treg cytokines; induction of inhibitory cytokines; the inhibition of inflammatory cytokines (e.g., IL-4, IL-1b, IL-5, TNF-α, IL-6, GM-CSF, IFN-γ, IL-2, IL-9, IL-12, IL-17, IL-18, IL-21, IL-22, IL-23, M-CSF, C reactive protein, acute phase protein, chemokines (e.g., MCP-1, RANTES, MIP-1α, MIP-1β, MIG, ITAC or IP-10), the production of anti-inflammatory cytokines (e.g., IL-4, IL-13, IL-10, etc.), chemokines (e.g., CCL-2, CXCL8), proteases (e.g., MMP-3, MMP-9), leukotrienes (e.g., CysLT-1, CysLT-2), prostaglandins (e.g., PGE2) or histamines; the inhibition of polarization to a Th17, Th1 or Th2 immune response; the inhibition of effector cell-specific cytokines: Th17 (e.g., IL-17, IL-25), Th1 (IFN-γ), Th2 (e.g., IL-4, IL-13); the inhibition of Th1-, Th2- or TH17-specific transcription factors; the inhibition of proliferation of effector T cells; the induction of apoptosis of effector T cells; the induction of tolerogenic dendritic cell-specific genes, the induction of FoxP3 expression, the inhibition of IgE induction or IgE-mediated immune responses; the inhibition of antibody responses (e.g., antigen-specific antibody production); the inhibition of T helper cell response; the production of TGF-β and/or IL-10; the inhibition of effector function of autoantibodies (e.g., inhibition in the depletion of cells, cell or tissue damage or complement activation); etc.

Any of the foregoing may be measured in vivo in one or more animal models or may be measured in vitro. One of ordinary skill in the art is familiar with such in vivo or in vitro measurements. Undesired immune responses or tolerogenic immune responses can be monitored using, for example, methods of assessing immune cell number and/or function, tetramer analysis, ELISPOT, flow cytometry-based analysis of cytokine expression, cytokine secretion, cytokine expression profiling, gene expression profiling, protein expression profiling, analysis of cell surface markers, PCR-based detection of immune cell receptor gene usage (see T. Clay et al., "Assays for Monitoring Cellular Immune Response to Active Immunotherapy of Cancer" Clinical Cancer Research 7:1127-1135 (2001)), etc. Undesired immune responses or tolerogenic immune responses may also be monitored using, for example, methods of assessing protein levels in plasma or serum, immune cell proliferation and/or functional assays, etc. In some embodiments, tolerogenic immune responses can be monitored by assessing the induction of FoxP3. In addition, specific methods are described in more detail in the Examples.

Preferably, tolerogenic immune responses lead to the inhibition of the development, progression or pathology of the diseases, disorders or conditions described herein. Whether or not the inventive compositions can lead to the inhibition of the development, progression or pathology of the diseases, disorders or conditions described herein can be measured with animal models of such diseases, disorders or conditions. In some embodiments, the reduction of an undesired immune response or generation of a tolerogenic immune response may be assessed by determining clinical endpoints, clinical efficacy, clinical symptoms, disease biomarkers and/or clinical scores. Undesired immune responses or tolerogenic immune responses can also be assessed with diagnostic tests to assess the presence or absence of a disease, disorder or condition as provided herein. In embodiments, methods for monitoring or assessing undesired immune (e.g., allergic) responses include assessing an immune response in a subject by skin reactivity and/or allergen-specific antibody production.

In some embodiments, monitoring or assessing the generation of an undesired immune response or a tolerogenic immune response in a subject can be prior to the administration of a composition of synthetic nanocarriers provided herein and/or prior to exposure to an allergen. In other embodiments, assessing the generation of an undesired immune response or tolerogenic immune response can be after administration of a composition of synthetic nanocarriers provided herein and/or and after exposure to an allergen. In some embodiments, the assessment is done after administration of the composition of synthetic nanocarriers, but prior to exposure to an allergen. In other embodiments, the assessment is done after exposure to an allergen, but prior to administration of the composition. In still other embodiments, the assessment is performed prior to both the administration of the synthetic nanocarriers and exposure to an allergen, while in yet other embodiments the assessment is performed after both the administration of synthetic nanocarriers and the exposure to an allergen. In further embodiments, the assessment is performed both prior to and after the administration of the synthetic nanocarriers and/or exposure to the allergen. In still other embodiments, the assessment is performed more than once on the subject to determine that a desirable immune state is maintained in the subject, such as a subject that has or is at risk of having an allergy.

An antibody response can be assessed by determining one or more antibody titers. "Antibody titer" means a measurable level of antibody production. Methods for measuring antibody titers are known in the art and include Enzyme-linked Immunosorbent Assay (ELISA). In embodiments, the antibody response can be quantitated, for example, as the number of antibodies, concentration of antibodies or titer. The values can be absolute or they can be relative. Assays for quantifying an antibody response include antibody capture assays, enzyme-linked immunosorbent assays (ELISAs), inhibition liquid phase absorption assays (ILPAAs), rocket immunoelectrophoresis (RIE) assays and line immunoelectrophoresis (LIE) assays. When an antibody response is compared to another antibody response the same type of quantitative value (e.g., titer) and method of measurement (e.g., ELISA) is preferably used to make the comparison.

An ELISA method for measuring an antibody titer, for example, a typical sandwich ELISA, may consist of the following steps (i) preparing an ELISA-plate coating material such that the antibody target of interest is coupled to a substrate polymer or other suitable material (ii) preparing the coating material in an aqueous solution (such as PBS) and delivering the coating material solution to the wells of a multiwell plate for overnight deposition of the coating onto the multiwell plate (iii) thoroughly washing the multiwell plate with wash buffer (such as 0.05% Tween-20 in PBS) to remove excess coating material (iv) blocking the plate for nonspecific binding by applying a diluent solution (such as 10% fetal bovine serum in PBS), (v) washing the blocking/diluent solution from the plate with wash buffer (vi) diluting the serum sample(s) containing antibodies and appropriate standards (positive controls) with diluent as required to obtain a concentration that suitably saturates the ELISA response (vii) serially diluting the plasma samples on the multiwell plate such to cover a range of concentrations suitable for generating an ELISA response curve (viii) incubating the plate to provide for antibody-target binding (ix) washing the plate with wash buffer to remove antibodies not bound to antigen (x) adding an appropriate concentration of a secondary detection antibody in same diluent such as a biotin-coupled detection antibody capable of binding the primary antibody (xi) incubating the plate with the applied detection antibody, followed by washing with wash buffer (xii) adding an enzyme such as streptavidin-HRP (horse radish peroxidase) that will bind to biotin found on biotinylated antibodies and incubating (xiii) washing the multiwell plate (xiv) adding substrate(s) (such as TMB solution) to the plate (xv) applying a stop solution (such as 2N sulfuric acid) when color development is complete (xvi) reading optical density of the plate wells at a specific wavelength for the substrate (450 nm with subtraction of readings at 570 nm) (xvi) applying a suitable multiparameter curve fit to the data and defining half-maximal effective concentration (EC50) as the concentration on the curve at which half the maximum OD value for the plate standards is achieved.

"Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include antigen-specific antibody production, antigen-specific B cell proliferation and/or activity or antigen-specific CD4+ T cell proliferation and/or activity.

C. INVENTIVE COMPOSITIONS

Provided herein are tolerogenic synthetic nanocarrier compositions comprising immunosuppressants and MHC Class II-restricted epitopes of an allergen and related methods. Such compositions and methods are useful for reducing the generation of undesired immune responses (e.g., undesired B cell or CD4+ T cell proliferation and/or activity, undesired antibody production, etc.) and promoting the generation of tolerogenic immune responses that are specific to the allergen. The compositions can be administered to subjects in which a tolerogenic immune response to an allergen is desired. Such subjects include those that have been, are being or will be exposed to an allergen. Such subjects include those that have experienced, are experiencing or are expected to experience an undesired immune (e.g., allergic) response to any of the allergens described herein. Such subjects also include those that have or are at risk of having an allergy to any of the allergens described herein.

As mentioned above, the synthetic nanocarriers are designed to comprise immunosuppressants and, in some embodiments, MHC Class II-restricted epitopes of an allergen against which a tolerogenic effect is desired. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the inventive synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a nonmethoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that does not comprise of pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, various elements of the synthetic nanocarriers can be coupled with the polymer.

The immunosuppressants and/or antigens can be coupled to the synthetic nanocarriers by any of a number of methods. Generally, the coupling can be a result of bonding between the immunosuppressants and/or antigens and the synthetic nanocarriers. This bonding can result in the immunosuppressants and/or antigens being attached to the surface of the synthetic nanocarrierss and/or contained within (encapsulated) the synthetic nanocarriers. In some embodiments, however, the immunosuppressants and/or antigens are encapsulated by the synthetic nanocarriers as a result of the structure of the synthetic nanocarriers rather than bonding to the synthetic nanocarriers. In preferable embodiments, the synthetic nanocarriers comprise a polymer as provided herein, and the immunosuppressants and/or antigens are coupled to the polymer.

When coupling occurs as a result of bonding between the immunosuppressants and/or antigens and synthetic nanocarriers, the coupling may occur via a coupling moiety. A coupling moiety can be any moiety through which an immunosuppressant and/or antigen is bonded to a synthetic nanocarrier. Such moieties include covalent bonds, such as an amide bond or ester bond, as well as separate molecules that bond (covalently or non-covalently) the immunosuppressant and/or antigen to the synthetic nanocarrier. Such molecules include linkers or polymers or a unit thereof. For example, the coupling moiety can comprise a charged polymer to which an immunosuppressant and/or antigen electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant or antigen can be covalently associated with one or more polymers of the polymeric matrix. In some embodiments, covalent association is mediated by a linker. In some embodiments, a component can be noncovalently associated with one or more polymers of the polymeric matrix. For example, in some embodiments a component can be encapsulated within, surrounded by, and/or dispersed throughout the polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly (glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-copolymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β- hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly (sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g., coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly [α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the inventive synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

Compositions according to the invention comprise synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, inventive synthetic nanocarriers are suspended in sterile saline solution for injection together with a preservative.

In embodiments, when preparing synthetic nanocarriers as carriers, methods for coupling components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to couple the components to the synthetic nanocarriers through the use of these surface groups rather than attaching the components to a polymer and then using this polymer conjugate in the construction of synthetic nanocarriers.

In certain embodiments, the coupling can be a covalent linker. In embodiments, peptides according to the invention can be covalently coupled to the external surface via a 1,2,3-triazole linker formed by the 1,3-dipolar cycloaddition reaction of azido groups on the surface of the nanocarrier with antigen or immunosuppressant containing an alkyne group or by the 1,3-dipolar cycloaddition reaction of alkynes on the surface of the nanocarrier with antigens or immunosuppressants containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component with the carboxylic acid group of a second component. The amide bond in the linker can be made using any of the conventional amide bond forming reactions with suitably protected amino acids and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group and another containing thiol/mercaptan groups with a component containing activated thiol group.

A triazole linker, specifically a 1,2,3-triazole of the form

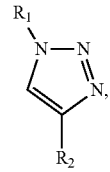

wherein R1 and R2 may be any chemical entities, is made by the 1,3-dipolar cycloaddition reaction of an azide attached to a first component such as the nanocarrier with a terminal alkyne attached to a second component such as the immunosuppressant antigen. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently couples the component to the particle through the 1,4-disubstituted 1,2,3-triazole linker.

A thioether linker is made by the formation of a sulfur-carbon (thioether) bond in the form, for instance, of R1-S—R2. Thioether can be made by either alkylation of a thiol/mercaptan (—SH) group on one component with an alkylating group such as halide or epoxide on a second component. Thioether linkers can also be formed by Michael addition of a thiol/mercaptan group on one component to an electron-deficient alkene group on a second component containing a maleimide group or vinyl sulfone group as the Michael acceptor. In another way, thioether linkers can be prepared by the radical thiol-ene reaction of a thiol/mercaptan group on one component with an alkene group on a second component.

A hydrazone linker is made by the reaction of a hydrazide group on one component with an aldehyde/ketone group on the second component.

A hydrazide linker is formed by the reaction of a hydrazine group on one component with a carboxylic acid group on the second component. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component.

An urea or thiourea linker is prepared by the reaction of an amine group on one component with an isocyanate or thioisocyanate group on the second component.

An amidine linker is prepared by the reaction of an amine group on one component with an imidoester group on the second component.

An amine linker is made by the alkylation reaction of an amine group on one component with an alkylating group such as halide, epoxide, or sulfonate ester group on the second component. Alternatively, an amine linker can also be made by reductive amination of an amine group on one component with an aldehyde or ketone group on the second component with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For example, a negative charged antigen or immunosuppressant can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatible groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that capable of coupling two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on NC to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be coupled by adsorption to a pre-formed synthetic nanocarrier or it can be coupled by encapsulation during the formation of the synthetic nanocarrier.

Any immunosuppressant as provided herein can be coupled to the synthetic nanocarrier. Immunosuppressants include, but are not limited to, statins; mTOR inhibitors, such as rapamycin or a rapamycin analog; TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, tripolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g, follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl) 1H-imidazole), SB-239063 (trans-1-(4hydroxycyclohexyl)-4-(fluorophenyl)-5-(2-methoxy-pyrimidin-4-yl) imidazole), SB-220025 (5-(2amino-4-pyrimidinyl)-4-(4-fluorophenyl)-1-(4-piperidinyl)imidazole)), and ARRY-797.

Examples of NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfiram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, sodium orthovanadate.

In some embodiments, antigens as described herein are also coupled to synthetic nanocarriers. In some embodiments, the antigens are coupled to the same or different synthetic nanocarriers as to which the immunosuppressants are coupled. In other embodiments, the antigens are not coupled to any synthetic nanocarriers.

In some embodiments, a component, such as an antigen or immunosuppressant, may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein may be isolated and can be included in the compositions in isolated form.

D. METHODS OF MAKING AND USING THE INVENTIVE COMPOSITIONS AND RELATED METHODS

Synthetic nanocarriers may be prepared using a wide variety of methods known in the art. For example, synthetic nanocarriers can be formed by methods as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements (i.e., components) of the inventive synthetic nanocarriers (such as moieties of which an immunofeature surface is comprised, targeting moieties, polymeric matrices, antigens, immunosuppressants and the like) may be coupled to the overall synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to components directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, ππ stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an inventive synthetic nanocarrier. In embodiments, encapsulation and/or absorption is a form of coupling. In embodiments, the inventive synthetic nanocarriers can be combined with an antigen by admixing in the same vehicle or delivery system.

Populations of synthetic nanocarriers may be combined to form pharmaceutical dosage forms according to the present invention using traditional pharmaceutical mixing methods. These include liquid-liquid mixing in which two or more suspensions, each containing one or more subsets of nanocarriers, are directly combined or are brought together via one or more vessels containing diluent. As synthetic nanocarriers may also be produced or stored in a powder form, dry powder-powder mixing could be performed as could the resuspension of two or more powders in a common media. Depending on the properties of the nanocarriers and their interaction potentials, there may be advantages conferred to one or another route of mixing.

Typical inventive compositions that comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention comprise inventive synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, inventive synthetic nanocarriers are suspended in sterile saline solution for injection together with a preservative.

It is to be understood that the compositions of the invention can be made in any suitable manner, and the invention is in no way limited to compositions that can be produced using the methods described herein. Selection of an appropriate method may require attention to the properties of the particular moieties being associated.

In some embodiments, inventive synthetic nanocarriers are manufactured under sterile conditions or are terminally sterilized. This can ensure that resulting compositions are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, inventive synthetic nanocarriers may be lyophilized and stored in suspension or as lyophilized powder depending on the formulation strategy for extended periods without losing activity.

The compositions of the invention can be administered by a variety of routes, including but not limited to subcutaneous, intranasal, oral, intravenous, intraperitoneal, intramuscular, transmucosal, transmucosal, sublingual, rectal, ophthalmic, pulmonary, intradermal, transdermal, transcutaneous or intradermal or by a combination of these routes. Routes of administration also include administration by inhalation or pulmonary aerosol. Techniques for preparing aerosol delivery systems are well known to those of skill in the art (see, for example, Sciarra and Cutie, "Aerosols," in Remington's Pharmaceutical Sciences, 18th edition, 1990, pp. 1694-1712; incorporated by reference).

The compositions of the invention can be administered in effective amounts, such as the effective amounts described elsewhere herein. Doses of dosage forms contain varying amounts of populations of synthetic nanocarriers and/or varying amounts of antigens and/or immunosuppressants, according to the invention. The amount of synthetic nanocarriers and/or antigens and/or immunosuppressants present in the inventive dosage forms can be varied according to the nature of the antigens and/or immunosuppressants, the therapeutic benefit to be accomplished, and other such parameters. In embodiments, dose ranging studies can be conducted to establish optimal therapeutic amount of the population of synthetic nanocarriers and the amount of antigens and/or immunosuppressants to be present in the dosage form. In embodiments, the synthetic nanocarriers and/or the antigens and/or immunosuppressants are present in the dosage form in an amount effective to generate a tolerogenic immune response to the antigens upon administration to a subject. It may be possible to determine amounts of the antigens and/or immunosuppressants effective to generate a tolerogenic immune response using conventional dose ranging studies and techniques in subjects. Inventive dosage forms may be administered at a variety of frequencies. In a preferred embodiment, at least one administration of the dosage form is sufficient to generate a pharmacologically relevant response. In more preferred embodiments, at least two administrations, at least three administrations, or at least four administrations, of the dosage form are utilized to ensure a pharmacologically relevant response.

Prophylactic administration of the inventive compositions can be initiated prior to the onset of disease, disorder or condition or therapeutic administration can be initiated after a disorder, disorder or condition is established.

In some embodiments, administration of synthetic nanocarriers is undertaken e.g., prior to exposure to an allergen. In exemplary embodiments, synthetic nanocarriers are administered at one or more times including, but not limited to, 30, 25, 20, 15, 14, 13, 12, 11, 10, 9, 8, 7, 6, 5, 4, 3, 2, 1, or 0 days prior to exposure to an allergen. In addition or alternatively, synthetic nanocarriers can be administered to a subject following exposure to an allergen. In exemplary embodiments, synthetic nanocarriers are administered at one or more times including, but not limited to, 1, 2, 3, 4, 5, 6, 7, 8, 9, 10, 11, 12, 13, 14, 15, 20, 25, 30, etc. days following exposure to an allergen.

In some embodiments, a maintenance dose (e.g., of a synthetic nanocarrier composition provided herein) is administered to a subject after an initial administration has resulted in a tolerogenic response in the subject, for example to maintain the tolerogenic effect achieved after the initial dose, to prevent an undesired immune reaction in the subject, or to prevent the subject becoming a subject at risk of experiencing an undesired immune response or an undesired level of an immune response. In some embodiments, the maintenance dose is the same dose as the initial dose the subject received. In some embodiments, the maintenance dose is a lower dose than the initial dose. For example, in some embodiments, the maintenance dose is about ¾, about ⅔, about ½, about ⅓, about ¼, about ⅛, about 1/10, about 1/20, about 1/25, about 1/50, about 1/100, about 1/1,000, about 1/10,000, about 1/100,000, or about 1/1,000,000 (weight/weight) of the initial dose.

The compositions and methods described herein can be used to induce or enhance a tolerogenic immune response and/or to suppress, modulate, direct or redirect an undesired immune response for the purpose of immune suppression. The compositions and methods described herein can be used for the generation of a tolerogenic immune response in a subject that has been, is being or will be exposed to an allergen.

EXAMPLES

Example 1

Immune Response of Synthetic Nanocarriers with Coupled Rapamycin with and without Ovalbumin Peptide (323-339)

Materials

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). Polyvinyl alcohol (85-89% hydrolyzed) was purchased from EMD Chemicals (Product Number 1.41350.1001).

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Rapamycin @ 50 mg/mL in methylene chloride. The solution was prepared by dissolving rapamycin in pure methylene chloride.

Solution 3: PLGA @ 100 mg/mL in methylene chloride. The solution was prepared by dissolving PLGA in pure methylene chloride.

Solution 4: Polyvinyl alcohol @ 50 mg/mL in 100 mM pH 8 phosphate buffer.

Method for Preparing Synthetic Nanocarrier Containing Rapamycin and Ovalbumin (323-339)

A primary water-in-oil emulsion was prepared first. W1/O1 was prepared by combining solution 1 (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amounts of peptide and rapamycin in the synthetic nanocarriers were determined by HPLC analysis. The total dry-synthetic nanocarrier mass per mL of suspension was determined by a gravimetric method.

Method for Synthetic Nanocarrier Containing Rapamycin

A primary water-in-oil emulsion was prepared first. W1/O1 was prepared by combining 0.13 M hydrochloric acid solution (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250. The (W1/O1/W2) emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amount of rapamycin in the synthetic nanocarrier was determined by HPLC analysis. The total dry-synthetic nanocarrier mass per mL of suspension was determined by a gravimetric method.

Method for Measuring Rapamycin Load

Approximately 3 mg of synthetic nanocarriers were collected and centrifuged to separate supernatant from synthetic nanocarrier pellet. Acetonitrile was added to the pellet, and the sample was sonicated and centrifuged to remove any insoluble material. The supernatant and pellet were injected on RP-HPLC and absorbance was read at 278 nm. The µg found in the pellet were used to calculate % entrapped (load), µg in supernatant and pellet were used to calculate total µg recovered.

Method for Measuring Ovalbumin (323-339) Load

Approximately 3 mg of synthetic nanocarriers were collected and centrifuged to separate supernatant from synthetic nanocarrier pellet. Trifluoroethanol was added to the pellet and the sample was sonicated to dissolve the polymer, 0.2% trifluoroacetic acid was added and sample was sonicated and then centrifuged to remove any insoluble material. The supernatant and pellet were injected on RP-HPLC and absorbance was read at 215 nm. The µg found in the pellet were used to calculate % entrapped (load), µg in supernatant and pellet were used to calculate total µg recovered.

Antigen-Specific Tolerogenic Dendritic Cells (Tdc) Activity on Treg Cell Development The assay included the use of OTII mice which have a transgenic T-cell receptor specific for an immune-dominant ovalbumin (323-339). In order to create antigen-specific tDCs, CD11c+ splenocytes were isolated, and the ovalbumin (323-339) peptide added in vitro at 1 µg/ml or no antigen. Soluble or nanocarrier-encapsulated rapamycin was then added to the DCs for 2 hours which were then washed extensively to remove free rapamycin from the culture. Purified responder CD4+CD25− cells were isolated from OTII mice and added to tDC at a 10:1 T to DC ratio. The mixture of tDC and OTII T-cells were then cultured for 4-5 days, and the frequency of Treg cells (CD4+ CD25highFoxP3+) were analyzed by flow cytometry as shown in FIG. 1. Regions were selected based on isotype controls.

Example 2

Mesoporous Silica Nanoparticles with Coupled Ibuprofen (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Ibuprofen is loaded by suspending the particles in a solution of sodium ibuprofen (1 mg/L) for 72 h. Free ibuprofen is then washed from the particles by centrifugation and redispersing in water.

Example 3

Liposomes Containing Cyclosporine A (Prophetic)

The liposomes are formed using thin film hydration. 1,2-Dipalmitoyl-sn-glycero-3-phosphocholine (DPPC) (32 µmol), cholesterol (32 µmol), and cyclosporin A (6.4 µmol) are dissolved in pure chloroform (3 mL). This lipid solution is added to a 50 mL round-bottom flask, and the solvent is evaporated on a rotary evaporator at a temperature of 60° C. The flask is then flushed with nitrogen gas to remove remaining solvent. Phosphate buffered saline (2 mL) and five glass beads are added to the flask, and the lipid film is hydrated by shaking at 60° C. for 1 h to form a suspension. The suspension is transferred to a small pressure tube and sonicated at 60° C. for four cycles of 30 s pulses with a 30 s delay between each pulse. The suspension is then left undisturbed at room temperature for 2 h to allow for complete hydration. The liposomes are washed by centrifugation followed by resuspension in fresh phosphate buffered saline.

Example 4

Polymeric Nanocarrier Containing Polymer-Rapamycin Conjugate (Prophetic)

Preparation of PLGA-Rapamycin Conjugate:

PLGA polymer with acid end group (7525 DLG1A, acid number 0.46 mmol/g, Lakeshore Biomaterials; 5 g, 2.3 mmol, 1.0 eq) is dissolved in 30 mL of dichloromethane (DCM). N,N-Dicyclohexylcarbodimide (1.2 eq, 2.8 mmol, 0.57 g) is added followed by rapamycin (1.0 eq, 2.3 mmol, 2.1 g) and 4-dimethylaminopyridine (DMAP) (2.0 eq, 4.6 mmol, 0.56 g). The mixture is stirred at rt for 2 days. The mixture is then filtered to remove insoluble dicyclohexylurea. The filtrate is concentrated to ca. 10 mL in volume and added to 100 mL of isopropyl alcohol (IPA) to precipitate out the PLGA-rapamycin conjugate. The IPA layer is removed and the polymer is then washed with 50 mL of IPA and 50 mL of methyl t-butyl ether (MTBE). The polymer is then dried under vacuum at 35 C for 2 days to give PLGA-rapamycin as a white solid (ca. 6.5 g).

Preparation of nanocarrier containing PLGA-rapamycin conjugate and ovalbumin peptide (323-339):

Nanocarrier containing PLGA-rapamycin is prepared according to the procedure described in Example 1 as follows:

Solutions for nanocarrier formation are prepared as follows:

Solution 1: Ovalbumin peptide 323-339 @ 20 mg/mL in dilute hydrochloric acid aqueous solution. The solution is prepared by dissolving ovalbumin peptide in 0.13 M hydrochloric acid solution at room temperature. Solution 2: PLGA-rapamycin @ 100 mg/mL in methylene chloride. The solution is prepared by dissolving PLGA-rapamycin in pure methylene chloride. Solution 3: PLA-PEG @ 100 mg/mL in methylene chloride. The solution is prepared by dissolving PLA-PEG in pure methylene chloride. Solution 4: Polyvinyl alcohol @ 50 mg/mL in 100 mM pH 8 phosphate buffer.

A primary water-in-oil emulsion is prepared first. W1/O1 is prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) is then prepared by combining solution 4 (3.0 mL) with the primary W1/O1 emulsion, vortexing for 10 s, and sonicating at 30% amplitude for 60 seconds using the Branson Digital Sonifier 250. The W1/O1/W2 emulsion is added to a beaker containing 70 mM pH 8 phosphate buffer solution (30 mL) and stirred at room temperature for 2 hours to allow the methylene chloride to evaporate and for the nanocarriers to form. A portion of the nanocarriers is washed by transferring the nanocarrier suspension to a centrifuge tube and centrifuging at 75,600×g and 4° C. for 35 min, removing the supernatant, and re-suspending the pellet in phosphate buffered saline. The washing procedure is repeated, and the pellet is re-suspended in phosphate buffered saline for a final nanocarrier dispersion of about 10 mg/mL.

Example 5

Preparation of Gold Nanocarriers (AuNCs) Containing Rapamycin (Prophetic)

Preparation of HS-PEG-Rapamycin:

A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Formation of Gold NCs (AuNCs):

An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 µm membrane filter to give the AuNCs solution. The AuNCs are characterized using visible spectroscopy and transmission electron microscopy. The AuNCs are ca. 20 nm diameter capped by citrate with peak absorption at 520 nm.

AuNCs Conjugate with HS-PEG-Rapamycin:

A solution of 150 µl of HS-PEG-rapamycin (10 µM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC-S-PEG-rapamycin is then pellet washed with 1×PBS buffer. The purified Gold-PEG-rapamycin nanocarriers are then resuspend in suitable buffer for further analysis and bioassays.

Example 6

Mesoporous Silica-Gold Core-Shell Nanocarriers Containing Ovalbumin (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Thiolated Ovalbumin (made by treating Ovalbumin with 2-iminothiolane hydrochloride) is loaded by suspending the particles in a solution of thiolated Ovalbumin (1 mg/L) for 72 h. The particles is then pellet washed with 1×PBS (pH 7.4) to remove free protein. The resulting silica-gold core-shell nanocarriers containing Ovalbumin are then re-suspended in 1×PBS for further analysis and assays.

Example 7

Liposomes Containing Rapamycin and Ovalbumin (Prophetic)

The liposomes are formed by thin film hydration. 1,2-Dipalmitoyl-sn-glycero-3-phosphocholine (DPPC) (32 μmol), cholesterol (32 μmol), and rapamycin (6.4 μmol) are dissolved in pure chloroform (3 mL). This lipid solution is added to a 10 mL glass tube and the solvent is removed under nitrogen gas stream and desiccated for 6 hr. under vacuum. Multilamellar vesicles are obtained by hydration of the film with 2.0 ml of 25 mM MOPS buffer pH 8.5, containing excess amount of Ovalbumin. The tube is vortexed until the lipid film is peeled of from the tube surface. To break the multilamellar vesicles into monolamellar, ten cycles of freezing (liquid nitrogen) and thawing (30° C. water bath) are applied. The sample is then diluted to 1 ml in 25 mM MOPS buffer pH 8.5. Size of the resulting liposome is homogenized by extrusion by passing the sample 10 fold through a 200 nm pore polycarbonate filters. The resulting liposomes are then used for further analysis and bioassays.

Example 8

Polymeric Nanocarriers Composed of Modified Polyamino Acid with Surface Conjugated Ovalbumin (Prophetic)

Step-1. Preparation of Poly(γ-glutamic acid) (γ-PGA) modified with L-phenylalanine ethyl ester (L-PAE): 4.7 unit mmol of γ-PGA (Mn=300 kD) is dissolved in 0.3 N—NaHCO3 aqueous solution (50 mL). L-PAE (4.7 mmol) and EDC·HCl (4.7 mmol) are added to the solution and stirred for 30 min at 4 C. The solution is then maintained at room temperature with stirring for 24 h. Low-molecular-weight chemicals are removed by dialysis using dialysis membrane with MWCO 50 kD. The resulting γ-PGA-graft-L-PAE is obtained by freeze-drying.

Step-2. Preparation of nanoparticles from γ-PGA-graft-L-PAE polymer: Nanoparticles composed of γ-PGA-graft-L-PAE are prepared by a precipitation and dialysis method. γ-PGA-graft-L-PAE (20 mg) was dissolved in 2 ml of DMSO followed by addition of 2 mL of water to form a translucent solution. The solution is then dialyzed against distilled water using cellulose membrane tubing (50,000 MWCO) to form the nanoparticles and to remove the organic solvents for 72 h at room temperature. The distilled water is exchanged at intervals of 12 h. The resulting nanoparticle solution (10 mg/mL in water) is then used for antigen conjugation.

Step-3. Ovalbumin conjugation to γ-PGA nanoparticles: Surface carboxylic acid groups of the γ-PGA nanoparticles (10 mg/ml) are first activated by EDC and NHS (10 mg/mL each in phosphate buffer, pH 5.8) for 2 h at ambient temperature. After pellet washing to remove excess EDC/NHS, the activated nanoparticles are mixed with 1 mL of Ovalbumin (10 mg/ml) in phosphate-buffered saline (PBS, pH 7.4) and the mixture is incubated at 4-8 C for 24 h. The resulting Ovalbumin conjugated γ-PGA nanoparticles are washed twice with PBS and resuspended at 5 mg/mL in PBS for further analysis and bioassays.

Example 9

Erythropoietin (EPO)-Encapsulated γ-PGA Nanoparticles (Prophetic)

To prepare the EPO-encapsulated γ-PGA nanoparticles, 0.25-4 mg of EPO is dissolved in 1 mL of PBS (pH 7.4) and 1 mL of the γ-PGA-graft-L-PAE (10 mg/mL in DMSO) is added to the EPO solution. The resulting solution is centrifuged at 14,000×g for 15 min and repeatedly rinsed with PBS. The resulting EPO-encapsulated γ-PGA nanoparticles are then resuspended in PBS (5 mg/mL) for further analysis and bioassay.

Example 10

Preparation of Gold Nanocarriers (AuNCs) Containing Ovalbumin (Prophetic)

Step-1. Formation of Gold NCs (AuNCs): An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 μm membrane filter to give the AuNCs solution. The AuNCs are characterized using visible spectroscopy and transmission electron microscopy. The AuNCs are ca. 20 nm diameter capped by citrate with peak absorption at 520 nm.

Step-2. Conjugation of Ovalbumin to AuNCs: A solution of 150 μl of thiolated Ovalbumin (10 μM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with Ovalbumin on the surface is then purified by centrifuge at 12,000 g for 30 minutes. The supernatant is decanted and the pellet containing AuNC-Ovalbumin is then pellet washed with 1×PBS buffer. The purified Gold-Ovalbumin nanocarriers are then resuspend in suitable buffer for further analysis and bioassays.

Example 11

Evaluating Tolerogenic Immune Response to Der P1 Antigen In Vivo (Prophetic)

Balb/c mice are immunized with a Der P1 antigen in incomplete Freunds adjuvant to induce CD4+ T-cell proliferation, the level of which is assessed. Subsequently, a composition of the invention comprising MHC Class II-restricted epitopes of Der P1 antigen and an immunosuppressant is administered subcutaneously in a dose-dependent manner. The same mice are then again exposed to the Der P1 antigen, and the level of CD4+ T cell proliferation is again assessed. Changes in the CD4+ T cell population are then monitored with a reduction in CD4+ T cell proliferation upon subsequent challenge with the Der P1 antigen indicating a tolerogenic immune response.

Example 12

Evaluating Tolerogenic Immune Responses with Synthetic Nanocarriers Comprising Immunosuppressant and APC Presentable Antigen In Vivo Materials and Methods of Synthetic Nanocarrier Production
Nanocarrier 1

Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Rapamycin @ 50 mg/mL in methylene chloride. The solution was prepared by dissolving rapamycin in pure methylene chloride.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

An oil-in-water emulsion was used to prepare the nanocarriers. The O/W emulsion was prepared by combining solution 1 (0.2 mL), solution 2 (0.75 mL), solution 3 (0.25 mL), and solution 4 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of rapamycin in the nanocarrier was determined by HPLC analysis. The total dry-nanocarrier mass per mL of suspension was determined by a gravimetric method.

| Nanocarrier ID | Effective Diameter (nm) | Rapamycin Content (% w/w) |
| --- | --- | --- |
| Nanocarrier 1 | 215 | 9.5 |

Nanocarrier 2

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The (W1/O1/W2) emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of peptide in the nanocarrier was determined by HPLC analysis. The total dry-nanocarrier mass per mL of suspension was determined by a gravimetric method.

| Nanocarrier ID | Effective Diameter (nm) | Peptide Content (% w/w) |
| --- | --- | --- |
| Nanocarrier 2 | 234 | 2.1 |

Nanocarrier 3

Simvastatin was purchased from LKT Laboratories, Inc. (2233 University Avenue West, St. Paul, Minn. 55114; Product Catalogue #S3449). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Simvastatin @ 50 mg/mL in methylene chloride. The solution was prepared by dissolving simvastatin in pure methylene chloride.

Solution 2: PLGA @ 100 mg/mL in methylene chloride. The solution was prepared by dissolving PLGA in pure methylene chloride.

Solution 3: PLA-PEG @ 100 mg/mL in methylene chloride. The solution was prepared by dissolving PLA-PEG in pure methylene chloride.

Solution 4: Polyvinyl alcohol @ 50 mg/mL in 100 mM pH 8 phosphate buffer.

An oil-in-water emulsion was used to prepare the nanocarriers. The O/W emulsion was prepared by combining solution 1 (0.15 mL), solution 2 (0.75 mL), solution 3 (0.25 mL), and solution 4 (3 mL) in a small pressure tube and sonicating at 30% amplitude for 60 seconds using a Branson Digital Sonifier 250. The O/W emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers was washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of simvastatin in the nanocarrier was determined by HPLC analysis. The total dry-nanocarrier mass per mL of suspension was determined by a gravimetric method.

| Nanocarrier ID | Effective Diameter (nm) | Simvastatin Content (% w/w) |
|---|---|---|
| Nanocarrier 3 | 196 | 8.0 |

Nanocarrier 4

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Rapamycin @ 50 mg/mL in methylene chloride. The solution was prepared by dissolving rapamycin in pure methylene chloride.

Solution 3: PLGA @ 100 mg/mL in methylene chloride. The solution was prepared by dissolving PLGA in pure methylene chloride.

Solution 4: PLA-PEG @ 100 mg/mL in methylene chloride. The solution was prepared by dissolving PLA-PEG in pure methylene chloride.

Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The (W1/O1/W2) emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and rapamycin in the nanocarrier were determined by HPLC analysis. The total dry-nanocarrier mass per mL of suspension was determined by a gravimetric method.

| Nanocarrier ID | Effective Diameter (nm) | Rapamycin Content (% w/w) | Peptide Content (% w/w) |
|---|---|---|---|
| 4 | 227 | 9.0 | 2.5 |

Nanocarrier 5

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Simvastatin was purchased from LKT Laboratories, Inc. (2233 University Avenue West, St. Paul, Minn. 55114; Product Catalogue #S3449). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Simvastatin @ 50 mg/mL in methylene chloride. The solution was prepared by dissolving simvastatin in pure methylene chloride.

Solution 3: PLGA @ 100 mg/mL in methylene chloride. The solution was prepared by dissolving PLGA in pure methylene chloride.

Solution 4: PLA-PEG @ 100 mg/mL in methylene chloride. The solution was prepared by dissolving PLA-PEG in pure methylene chloride.

Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.15 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and simvastatin in the nanocarrier were determined by HPLC analysis. The total dry-nanocarrier mass per mL of suspension was determined by a gravimetric method.

| Nanocarrier ID | Effective Diameter (nm) | Simvastatin Content (% w/w) | Peptide Content (% w/w) |
|---|---|---|---|
| Nanocarrier 5 | 226 | 2.7 | 1.9 |

In Vivo Administration 1

Spleens from B6.Cg-Tg(TcraTcrb)425Cbn/J (OTII) and C57BL/6 (B6) mice were harvested, mechanically dissociated and filtered separately through a 70 µM sieve to yield a single-cell suspension. Purified $CD4^+CD25-$ cells were then extracted in a 2-step process. Using a Miltenyi Biotec AutoMACS magnetic cell sorter spleen cells were first labeled with $CD4^+$ T-cell isolation kit II and the unlabeled fraction was depleted of $CD25^+$ cells with CD25 depletion kit. The purified B6 cells were stained with an intracellular dye, Carboxyfluorescein Succinimidyl Ester (CFSE), before being admixed at equal concentrations with the purified OTII cells. They were then injected intravenously (i.v.) into B6.SJL-Ptprc$^a$/BoyAi (CD45.1) recipient mice.

The next day the recipient CD45.1 mice were treated with targeted tolerogenic synthetic vaccine particles (t²SVP). They were loaded with combinations of ovalbumin peptide (323-339) (OVA$^{323-339}$), Rapamycin (Rapa) and/or Simvastatin (Simva) and were administered subcutaneously (s.c.).

The injection constitutes a tolerogenic treatment and was followed by 4 more injections each spaced 2 weeks apart. After the treatment schedule was completed the recipient CD45.1 animals were killed and their spleens and popliteal lymph nodes were harvested, mechanically dissociated and filtered separately through a 70 µM sieve to yield a single-cell suspension. The spleen cells were depleted of red blood cells (RBCs) by incubation with RBC lysis buffer (Stem Cell Technologies) and cell counts were performed on both the spleens and lymph nodes.

Spleen or lymph node cells were cultured in CM (complete media) supplemented with 10 U/ml IL-2, restimulated with OPII at 0.3×10$^6$ cells/well in 96-well round bottom (RB) plates and incubated at 37° C., 5% $CO_2$. Cells were split at Day 2 and harvested on Day 5. Supernatants were collected and frozen while cells were stained for phenotypic analysis by flow cytometry. The cells were analyzed on a Becton Dickinson FacsCanto flow cytometer.

In Vivo Administration 2

Spleens from B6.Cg-Tg(TcraTcrb)425Cbn/J (OTII) and C57BL/6 (B6) mice were harvested, mechanically dissociated and filtered separately through a 70 µM sieve to yield a single-cell suspension. Purified $CD4^+CD25-$ cells were then extracted in a 2-step process using a Miltenyi Biotec AutoMACS magnetic cell sorter. Spleen cells were labeled using Miltenyi's $CD4^+$ T-cell isolation kit II. The unlabeled CD4+ T-cell fraction was then depleted of $CD25^+$ cells with CD25 depletion kit. The purified CD4 cells from B6 mice were then stained with an intracellular dye, Carboxyfluorescein Succinimidyl Ester (CFSE), before being admixed at equal concentrations with the purified OTII cells. They were then injected intravenously (i.v.) into B6.SJL-Ptprc$^a$/BoyAi (CD45.1) recipient mice.

The next day the recipient CD45.1 mice were treated with targeted tolerogenic synthetic vaccine particles. They comprised combinations of ovalbumin peptide (323-339) (OVA$^{323-339}$), Rapamycin (Rapa) and Simvastatin (Simva) and were administered subcutaneously (s.c.) or intravenously (i.v.).

After the treatment schedule was completed the recipient CD45.1 animals were killed and their spleens and popliteal lymph nodes were harvested, mechanically dissociated and filtered separately through a 70 µM sieve to yield a single-cell suspension. The spleen cells were depleted of red blood cells (RBCs) by incorporation with RBC lysis buffer (Stem Cell Technologies) and cell counts were performed on both the spleens and lymph nodes.

Spleen or lymph node cells were cultured in CM supplemented with 10 U/ml IL-2, restimulated with 1 µM OPII at 0.3×10$^6$ cells/well in 96-well round bottom (RB) plates and incubated at 37° C., 5% $CO_2$. Cells were split at Day 2 and harvested on Day 5. Supernatants were collected and frozen while cells were stained for phenotypic analysis by flow cytometry. The cells were analyzed on a Becton Dickinson FacsCanto flow cytometer.

Results

Figure 2:
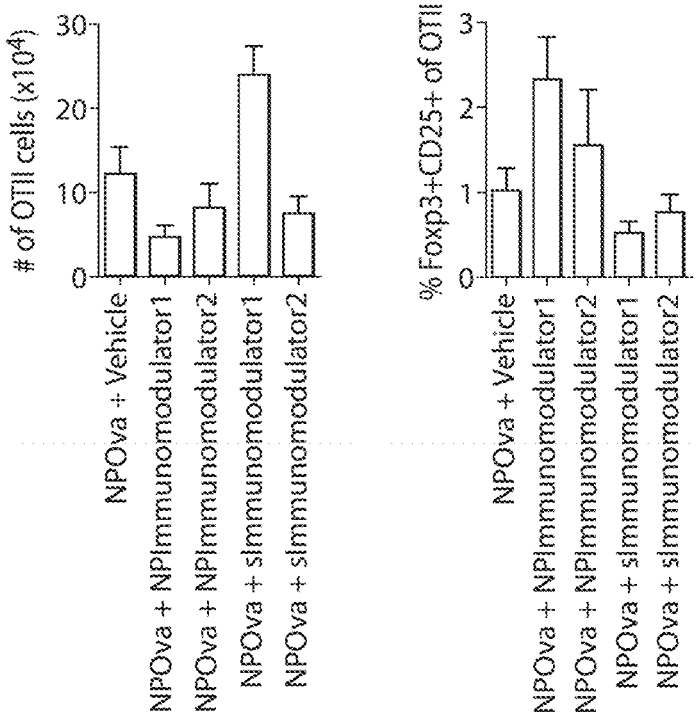
FIG. 2 shows an effect on the number of antigen-specific effector T cells with synthetic nanocarriers of the invention comprising immunosuppressant (rapamycin or simvastatin) (after a single injection).
Figure 3:
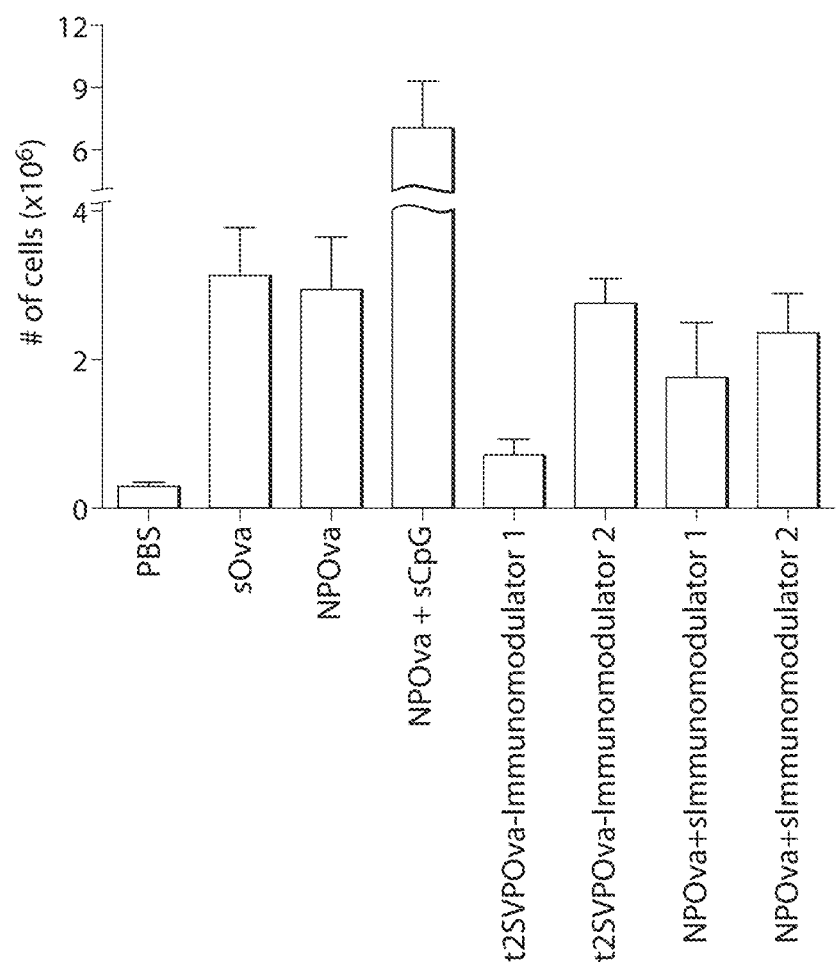
FIG. 3 shows a decrease in the number of popliteal lymph node cells with synthetic nanocarriers of the invention comprising immunosuppressant (rapamycin or simvastatin) (after multiple injections).

The results are shown in FIGS. 2 and 3 (Immunomodulator 1: rapamycin; immunomodulator 2: simvastatin). The figures shows in vivo effects and demonstrates that antigen-specific expansion of effector immune cells is reduced with synthetic nanocarriers comprising antigen and immunosuppressants as compared to antigen alone or synthetic nanocarriers comprising antigen with and without an immunostimulatory molecule.

Example 13

Assessing the Effects of Nanocarriers with Antigens and Immunosuppressants on Immune Responses Materials and Methods Nanocarrier 1

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: PLGA @ 100 mg/mL in methylene chloride. The solution was prepared by dissolving PLGA in pure methylene chloride. Solution 3: PLA-PEG @ 100 mg/mL in methylene chloride. The solution was prepared by dissolving PLA-PEG in pure methylene chloride. Solution 4: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250. The (W1/O1/W2) emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of peptide in the nanocarrier was determined by HPLC analysis. The total dry-nanocarrier mass per mL of suspension was determined by a gravimetric method.

| Nanocarrier ID | Effective Diameter (nm) | Peptide Content (% w/w) |
|---|---|---|
| 1 | 234 | 2.1 |

Nanocarrier 2

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue #R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows:

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: Rapamycin @ 50 mg/mL in methylene chloride. The solution was prepared by dissolving rapamycin in pure methylene chloride. Solution 3: PLGA @ 100 mg/mL in methylene chloride. The solution was prepared by dissolving PLGA in pure methylene chloride. Solution 4: PLA-PEG @ 100 mg/mL in methylene chloride. The solution was prepared by dissolving PLA-PEG in pure methylene chloride. Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250. The (W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and rapamycin in the nanocarrier were determined by HPLC analysis. The total dry-nanocarrier mass per mL of suspension was determined by a gravimetric method.

| Nanocarrier ID | Effective Diameter (nm) | Rapamycin Content (% w/w) | Peptide Content (% w/w) |
|---|---|---|---|
| 2 | 227 | 9.0 | 2.5 |

Immunization

Animals received immunization every 2 weeks at the same time they received the treatment. Each of these groups was split into subgroups to test the capacity of different treatments to modify the Ig titers induced. A control subgroup did not receive tolerogenic treatment. Two subgroups received nanocarrier carrying just OVA$_{323-339}$ peptide or in combination with rapamycin.

Immunization was administered via the following routes (values are per animal): 20 µl/limb of OVA+CpG (12.5 µg OVA+10 µg CpG), both hind limbs s.c. Tolerogenic treatments were administered via the following route (values are per animal): 200 µl nanocarriers were provided at 100 µm/ml of OVA$_{323-339}$ content.

Measurement of IgG

The level of IgG antibodies were measured. This level is indicative of immunoglobulins in general, including IgEs, which are of particular relevance in allergy. Blocker Casein in PBS (Thermo Fisher, Catalog #37528) was used as diluent. 0.05% Tween-20 in PBS was used as wash buffer, prepared by adding 10 ml of Tween-20 ((Sigma, Catalog #P9416-100 mL) to 2 liters of a 10×PBS stock (PBS: OmniPur® 10×PBS Liquid Concentrate, 4 L, EMD Chemicals, Catalog #6505) and 18 Liters of deionized water. OVA protein at a stock concentration of 5 mg/ml was used as a coating material. A 1:1000 dilution to 5 µg/ml was used as a working concentration. Each well of the assay plates was coated with 100 µl diluted OVA per well, plates were sealed with sealing film (VWR catalog #60941-120), and incubated overnight at 4° C. Costar9017 96-well Flat bottom plates were used as assay plates, Costar9017.

Low-binding polypropylene 96-well plate or tubes were used as set-up plates, in which samples were prepared before being transferred to the assay plate. The setup plates did not contain any antigen and, therefore, serum antibodies did not bind to the plate during the setup of the samples. Setup plates were used for sample preparation to minimize binding that might occur during preparation or pipetting of samples if an antigen-coated plate was used to prepare the samples. Before preparing samples in the setup plate, wells were covered with diluent to block any non-specific binding and the plate was sealed and incubated at 4° C. overnight.

Assay plates were washed three times with wash buffer, and wash buffer was completely aspirated out of the wells after the last wash. After washing, 300 µl diluent were added to each well of assay plate(s) to block non-specific binding and plates were incubated at least 2 hours at room temperature. Serum samples were prepared in the setup plate at appropriate starting dilutions. Starting dilutions were sometimes also prepared in 1.5 ml tubes using diluent. Appropriate starting dilutions were determined based on previous data, where available. Where no previous data was available, the lowest starting dilution was 1:40. Once diluted, 200 µl of the starting dilution of the serum sample was transferred from the appropriate well of the setup plate.

An exemplary setup plate layout is described as follows: Columns 2 and 11 contained anti-Ovabumin monoclonal IgG2b isotype (AbCam, ab17291) standard, diluted to 1 µg/mL (1:4000 dilution). Columns 3-10 contained serum samples (at appropriate dilutions). Columns 1 and 12 were not used for samples or standards to avoid any bias of measurements due to edge effect. Instead, columns 1 and 12 contained 200 µl diluent. Normal mouse serum diluted 1:40 was used as a negative control. Anti-mouse IgG2a diluted 1:500 from 0.5 mg/mL stock (BD Bioscience) was used as an isotype control.

Once all samples were prepared in the setup plate, the plate was sealed and stored at 4° C. until blocking of the assay plates was complete. Assay plates were washed three times with wash buffer, and wash buffer was completely aspirated after the last wash. After washing, 100 µL of diluent was added to all wells in rows B-H of the assay plates. A 12-channel pipet was used to transfer samples from the setup plate to the assay plate. Samples were mixed prior to transfer by pipetting 150 µl of diluted serum up and down 3 times. After mixing, 150 µl of each sample was transferred from the setup plate and added to row A of the respective assay plate.

Once the starting dilutions of each sample were transferred from the setup plate to row A of the assay plate, serial dilutions were pipetted on the assay plate as follows: 50 µl of each serum sample was removed from row A using 12-channel pipet and mixed with the 100 µl of diluent previously added to each well of row B. This step was repeated down the entire plate. After pipetting the dilution of the final row, 50 µl of fluid was removed from the wells in the final row and discarded, resulting in a final volume of 100 µl in every well of the assay plate. Once sample dilutions were prepared in the assay plates, the plates were incubated at room temperature for at least 2 hours.

After the incubation, plates were washed three times with wash buffer. Detection antibody (Goat anti-mouse anti-IgG, HRP conjugated, AbCam ab98717) was diluted 1:1500 (0.33 µg/mL) in diluent and 100 µl of the diluted antibody was added to each well. Plates were incubated for 1 hour at room temperature and then washed three times with wash buffer, with each washing step including a soak time of at least 30 seconds.

After washing, detection substrate was added to the wells. Equal parts of substrate A and substrate B (BD Biosciences TMB Substrate Reagent Set, catalog #555214) were combined immediately before addition to the assay plates, and 100 µl of the mixed substrate solution were added to each well and incubated for 10 minutes in the dark. The reaction was stopped by adding 50 µl of stop solution (2N $H_2SO_4$) to each well after the 10 minute period. The optical density (OD) of the wells was assessed immediately after adding the stop solution on a plate reader at 450 nm with subtraction at 570 nm. Data analysis was performed using Molecular Device's software SoftMax Pro v5.4. In some cases, a four-parameter logistic curve-fit graph was prepared with the dilution on the x-axis (log scale) and the OD value on the y-axis (linear scale), and the half maximum value (EC50) for each sample was determined. The plate template at the top of the layout was adjusted to reflect the dilution of each sample (1 per column).

Determination of % OVA+ Dividing B Cells

Ovalbumin+ B-cell division was assessed by flow cytometry. Splenocytes from experimental animals were stained with Cell Tracker Orange (CTO), a thiol-reactive fluorescent probe suitable for long-term cell labeling, and cultured in complete media at 37 C, 5% $CO_2$ with Ovalbumin protein or peptide for 3 days. On day 3 the cells were washed, blocked with anti-CD16/32 antibody and then stained with conjugated antibodies specific to B220 and CD19. Alexa 647 conjugated ovalbumin protein was also incubated with the cells to label Ovalbumin specific BCRs. Those splenocytes that were CD19+ B220+ OVA-Alexa647+ were assessed for proliferation by comparing the differential CTO staining. Those that were CTO low were labeled as proliferating Ovalbumin+ B-cells and were compared to the CTO high Ovalbumin+ B-cells to quantify the percentages.

Results

Figure 4:
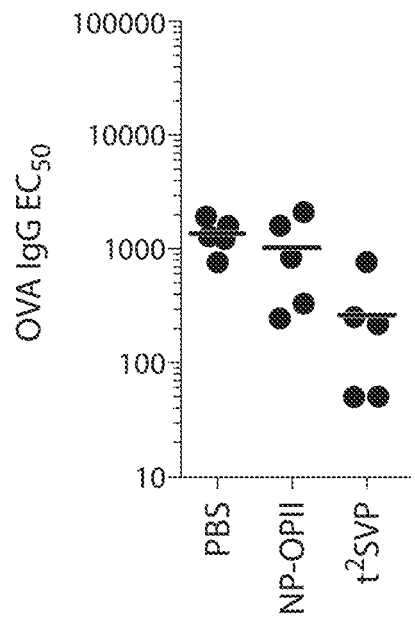
FIG. 4 shows a reduction in antigen-specific IgG levels with the administration of synthetic nanocarriers comprising ova peptide and the immunosuppressant rapamycin.
Figure 5:
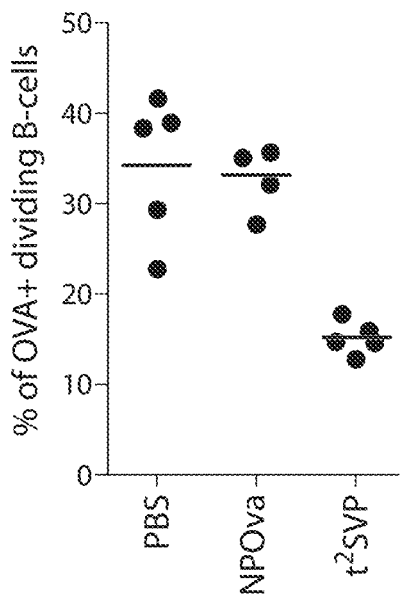
FIG. 5 demonstrates a reduction in the number of antigen-specific B cells with synthetic nanocarriers comprising ova peptide and the immunosuppressant rapamycin.

FIG. 4 shows a reduction in antigen-specific IgG levels with the administration of synthetic nanocarriers comprising ova peptide and the immunosuppressant rapamycin. The level of IgG antibodies is reflective of antibody production in general including the production of IgE antibodies, which are of particular relevance in allergy and allergic reactions. FIG. 5 also demonstrates a reduction, but in the number of antigen-specific B cells with the synthetic nanocarriers. These results demonstrate the reduction in undesired immune responses relevant to allergy and allergic responses with synthetic nanocarriers coupled to ova peptide (comprising an MHC Class II-restricted epitope) and immunosuppressant.

Example 14

Assessing the Effects of Nanocarriers with Antigens and Immunosuppressants on Allergic Asthma Nanocarriers Nanocarriers were prepared according to methods provided above (Example 13).

Immunization

The nanocarriers were thawed and equilibrated. Initial dilutions constituted a 10× stock solution, and were further diluted to a concentration of 100 µg/ml in $OVA_{323-339}$, or a 1× solution. This 1× solution was used for injections at 200 µl per i.v. injection. Animals were immunized with OVA protein (OVA) and treated with $OVA_{323-339}$ peptide to assess the capacity of nanocarriers to control the allergic response in absence of B cell antigens. Immunization routes were as follows: 10 µg of OVA+4 mg Alum i.p. in 400 µl per each Balb/C immunologically naïve female mouse. Experimental groups consisted of 5 animals each. Spleen cells were restimulated with antigen using CFSE or CTO to determine the amount of Ag-specific proliferation.

Levels of Specific Types of Immune Cells

FCS files were analyzed using FlowJo software. 7AAD positive cells (a nuclear dye that label dead cells) positive cells were excluded and cell morphologies dependent on expression of CD4, CD8, Gr-1, F4/80, B220, TCRb and CD11b were quantified.

Gating strategy for T-cell subsets→7AAD– F4/80– GR-1– TCRb+CD4+/–CD8+/–

Gating strategy for B-cell subsets→7AAD– B220+ TCRb–

Gating strategy for Eosinophils→7AAD– F4/80– Gr-1+ TCRb– CD11b+Gr-1+

Determination of % Dividing CD4+ T Cells

The frequency of Ovalbumin reactive $CD4^+$ T cells was calculated by way of flow cytometry. Splenocytes from experimental animals were stained with CFSE, a thiol-reactive Fluorescent Probe suitable for long-term cell labeling, and cultured in complete media at 37 C, 5% $CO_2$ with Ovalbumin protein for 3 days. On day 3 the cells were washed, blocked with anti-CD16/32 antibody and then stained with conjugated antibodies specific to TCR CD4 and CD8a. Splenocytes that were TCR+CD4 or TCR+CD8a+ were assessed for proliferation by comparing the differential CFSE staining.

Measurement of IgE Antibodies

IgE antibodies were measured using a Mouse OVA-IgE ELISA kit provided by MDBioproducts (Cat #M036005) consistent with the manufacturer's instructions.

Results

Figure 6:
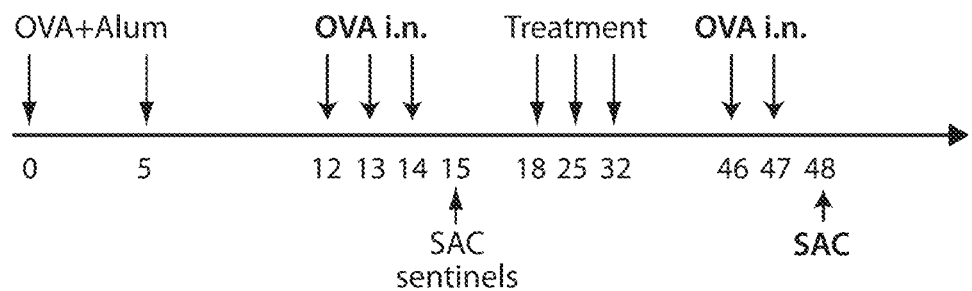
FIG. 6 demonstrates an overall reduction in the number of various immune cells in lavage samples from asthma model animal subjects treated with synthetic nanocarriers comprising ova peptide and immunosuppressant.
Figure 6:
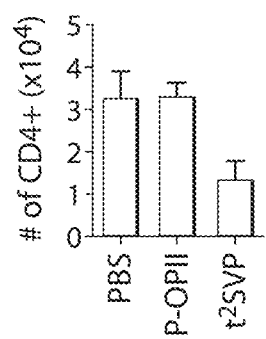
Figure 7:
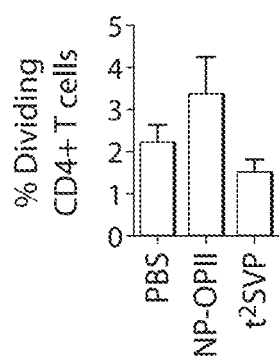
FIG. 7 demonstrates a reduction in the percentage of dividing CD4+ T cells as a result of treatment with synthetic nanocarriers comprising ova peptide and the immunosuppressant rapamycin in asthma model animal subjects.
Figure 8:
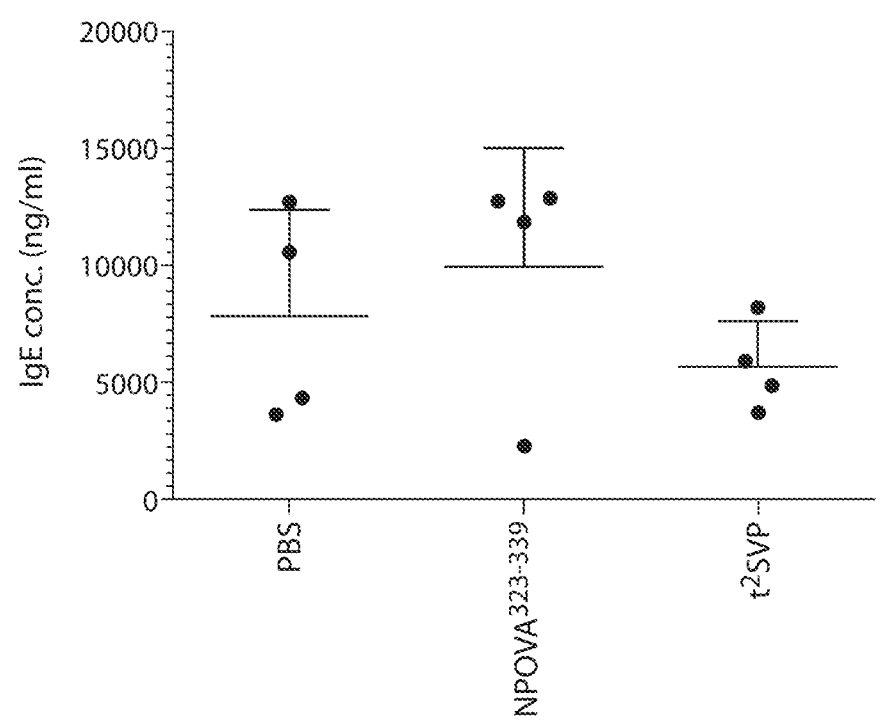
FIG. 8 demonstrates a reduction in the production of antigen-specific IgE antibodies.

FIGS. 6 and 7 demonstrate the effectiveness of the nanocarriers in an animal model for allergic asthma. Specifically, FIG. 6 demonstrates an overall reduction in the number of various immune cells in lavage samples from asthma model animal subjects treated with synthetic nanocarriers comprising $OVA_{323-339}$ (an MHC Class II-restricted epitope) and immunosuppressant. FIG. 7 demonstrates a reduction in the percentage of dividing CD4+ T cells as a result of the same treatment. FIG. 8 demonstrates a reduction in the production of antigen-specific IgE antibodies.

What is claimed is:

1. A method comprising administering to a subject, a composition comprising:
   (i) a first population of polymeric synthetic nanocarriers that are coupled to rapamycin or a rapamycin analog and
   (ii) a second population of polymeric synthetic nanocarriers that are coupled to MHC Class II-restricted epitopes of an allergen,
   wherein at least 75% of the polymeric synthetic nanocarriers of the first population of synthetic nanocarriers have a minimum dimension, obtained using dynamic light scattering, that is greater than 110 nm, and a maximum dimension, obtained using dynamic light scattering, that is equal to or less than 500 nm, and
   wherein the composition comprises substantially no B cell epitopes of the allergen, and wherein the load of the rapamycin or a rapamycin analog on average across the first population of synthetic nanocarriers is at least 2% but no more than 25% (weight/weight).

2. A method comprising:
   administering to a subject a composition comprising:
   (i) a first population of polymeric synthetic nanocarriers that are coupled to rapamycin or a rapamycin analog, and
   (ii) a second population of polymeric synthetic nanocarriers that are coupled to MHC Class II-restricted epitopes of an allergen,
   wherein at least 75% of the polymeric synthetic nanocarriers of the first population of synthetic nanocarriers have a minimum dimension, obtained using dynamic light scattering, that is greater than 110 nm, and a maximum dimension, obtained using dynamic light scattering, that is equal to or less than 500 nm, and
   wherein the composition comprises substantially no B cell epitopes of the allergen, wherein the load of the rapamycin or a rapamycin analog on average across the first population of synthetic nanocarriers is at least 2% but no more than 25% (weight/weight), wherein the composition is in an amount effective to reduce an undesired immune response to the allergen in the subject, and wherein the subject is experiencing or is at risk of experiencing the undesired immune response to the allergen.

3. A method comprising:
   reducing an undesired immune response to an allergen in a subject by administering a composition comprising:
   (i) a first population of polymeric synthetic nanocarriers that are coupled to rapamycin or a rapamycin analog, and
   (ii) a second population of polymeric synthetic nanocarriers that are coupled to MHC Class II-restricted epitopes of the allergen,
   wherein at least 75% of the polymeric synthetic nanocarriers of the first population of synthetic nanocarriers have a minimum dimension, obtained using dynamic light scattering, that is greater than 110 nm, and a maximum dimension, obtained using dynamic light scattering, that is equal to or less than 500 nm, and
   wherein the composition comprises substantially no B cell epitopes of the allergen, wherein the load of the rapamycin or a rapamycin analog on average across the first population of synthetic nanocarriers is at least 2% but no more than 25% (weight/weight), wherein the composition is in an amount effective to reduce the undesired immune response to the allergen in the subject, and wherein the subject is experiencing or is at risk of experiencing the undesired immune response to the allergen.

4. A method comprising:
   administering a composition to a subject according to a protocol that was previously shown to reduce an undesired immune response to an allergen in one or more test subjects;
   wherein the composition comprises:
   (i) a first population of polymeric synthetic nanocarriers that are coupled to rapamycin or a rapamycin analog, and
   (ii) a second population of polymeric synthetic nanocarriers that are coupled to MHC Class II-restricted epitopes of the allergen,
   wherein at least 75% of the polymeric synthetic nanocarriers of the first population of synthetic nanocarriers have a minimum dimension, obtained using dynamic light scattering, that is greater than 110 nm, and a maximum dimension, obtained using dynamic light scattering, that is equal to or less than 500 nm, and
   wherein the composition comprises substantially no B cell epitopes of the allergen, wherein the load of the rapamycin or a rapamycin analog on average across the first population of synthetic nanocarriers is at least 2% but no more than 25% (weight/weight), wherein the composition is in an amount effective to reduce the undesired immune response to the allergen in the subject, and wherein the subject is experiencing or is at risk of experiencing the undesired immune response to the allergen.

5. The method of claim 1, wherein the allergen induces allergen-specific antibody production and/or allergen-specific CD4+ T cell proliferation and/or activity in the subject.

6. The method of claim 2, wherein the undesired immune response is allergen-specific antibody production and/or allergen-specific CD4+ T cell proliferation and/or activity.

7. The method of claim 3, wherein the undesired immune response is allergen-specific antibody production and/or allergen-specific CD4+ T cell proliferation and/or activity.

8. The method of claim 4, wherein the undesired immune response is allergen-specific antibody production and/or allergen-specific CD4+ T cell proliferation and/or activity.

9. The method of claim 1, wherein the allergen comprises an asthma antigen, a hay fever antigen, a hives antigen, an eczema antigen, a plant allergen, an insect sting allergen, an insect allergen, an animal allergen, a fungal allergen, a drug allergen, a pet allergen, a latex allergen, a mold allergen, a cosmetic allergen or a food allergen.

10. The method of claim 2, wherein the allergen comprises an asthma antigen, a hay fever antigen, a hives antigen, an eczema antigen, a plant allergen, an insect sting allergen, an insect allergen, an animal allergen, a fungal allergen, a drug allergen, a pet allergen, a latex allergen, a mold allergen, a cosmetic allergen or a food allergen.

11. The method of claim 3, wherein the allergen comprises an asthma antigen, a hay fever antigen, a hives antigen, an eczema antigen, a plant allergen, an insect sting allergen, an insect allergen, an animal allergen, a fungal allergen, a drug allergen, a pet allergen, a latex allergen, a mold allergen, a cosmetic allergen or a food allergen.

12. The method of claim 4, wherein the allergen comprises an asthma antigen, a hay fever antigen, a hives antigen, an eczema antigen, a plant allergen, an insect sting allergen, an insect allergen, an animal allergen, a fungal allergen, a drug allergen, a pet allergen, a latex allergen, a mold allergen, a cosmetic allergen or a food allergen.

13. The method of claim 1, wherein the polymeric synthetic nanocarriers comprise a polyester, a polyester coupled to a polyether, polyamino acid, polycarbonate, polyacetal, polyketal, polysaccharide, polyethyloxazoline or polyethyleneimine.

14. The method of claim 13, wherein the polyester comprises a poly(lactic acid), poly(glycolic acid), poly(lactic-co-glycolic acid) or polycaprolactone.

15. The method of claim 13, wherein the polymeric synthetic nanocarriers comprise a polyester and a polyester coupled to a polyether.

16. The method of claim 13, wherein the polyether comprises polyethylene glycol or polypropylene glycol.

17. The method of claim 1, wherein the aspect ratio of the maximum to minimum dimension of the synthetic nanocarriers of the first population or second population is greater than 1:1, 1:1.2, 1:1.5, 1:2, 1:3, 1:5, 1:7 or 1:10.

18. The method of claim 1, wherein at least 80%, at least 90%, or at least 95% of the first and/or second population of synthetic nanocarriers have a minimum dimension or maximum dimension that falls within 5%, 10%, or 20% of the mean diameter of the synthetic nanocarriers.

* * * * *